United States Patent [19]

Guthrie et al.

[11] Patent Number: 4,927,826
[45] Date of Patent: May 22, 1990

[54] CYCLOPROYLPROPENAMIDES USEFUL AS PLATELET ACTIVING FACTOR (PAF) ANTAGONISTS

[75] Inventors: Robert W. Guthrie, Saddle Brook; Richard W. Kierstead; Jefferson W. Tilley, both of North Caldwell, all of N.J.

[73] Assignee: Hoffman-La Roche Inc., Nutley, N.J.

[21] Appl. No.: 238,224

[22] Filed: Aug. 30, 1988

Related U.S. Application Data

[62] Division of Ser. No. 72,390, Jul. 10, 1987, Pat. No. 4,786,646.

[51] Int. Cl.$^5$ .................. C07D 239/42; C07D 403/12; A61K 31/505
[52] U.S. Cl. .................................. 514/256; 514/269; 514/274; 514/275; 544/296; 544/298; 544/316; 544/319; 544/322; 544/327; 544/329; 544/332; 544/334; 544/335
[58] Field of Search ............... 544/334, 335, 296, 298, 544/316, 319, 322, 327, 329, 332; 514/256

[56] References Cited

U.S. PATENT DOCUMENTS

| | | | |
|---|---|---|---|
| 3,072,649 | 2/1963 | Semb et al. | 546/309 |
| 4,493,726 | 1/1986 | Burdoska et al. | 71/87 |
| 4,542,145 | 9/1985 | Wright, Jr. et al. | 514/383 |
| 4,568,685 | 2/1986 | Wright, Jr. et al. | 514/383 |
| 4,568,687 | 2/1946 | Wright, Jr. et al. | 514/399 |

FOREIGN PATENT DOCUMENTS

| | | |
|---|---|---|
| 61-044869 | 3/1986 | Japan . |
| 61-044870 | 3/1986 | Japan . |
| 62-012757 | 1/1987 | Japan . |

OTHER PUBLICATIONS

"Amide Derivatives and 5-Lipoxygenase Inhibitors Containing Them as an Active Ingredient", Wakabayashi, Toshio CA 104:168177c.
"Preparation of Benzenealkenamides & Antiallergic Agents Containing Them", Takai, Makoto; CA 107:154084v.
"Unsaturated Fatty Acid Piperazides and Analogs", Hotoda, Katusmi CA 105:226649s.
Japanese 82-21, 370 C.A. 97:6167j.
Jpanese 82-18, 973, C.A. 96:178,218x.

Primary Examiner—Richard A. Schwartz
Assistant Examiner—Richard Sharpe

Attorney, Agent, or Firm—George M. Gould; Bernard S. Leon; William G. Isgro

[57] ABSTRACT

The invention relates to compounds of the formula

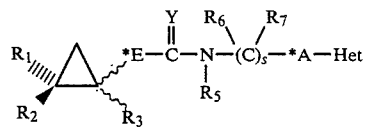

Y is O or S, *A is paraphenylene or *—$(CH_2)_n$—$(X)_m$—$(CH_2)_r$—, X is O, S or —CH=CH—, n or r, independently, are integers from 0 to 3, s is an integer from 0 to 1, m is an integer from 0 to 1, provided that when m is 1, n+s must be at least 2, $R_1$ and $R_2$, independently, are hydrogen, lower alkyl, cycloalkyl, lower alkenyl. Het or aryl, *E is

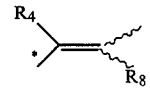

or —$(CH_2)_k$— wherein k is an integer fro 0 to 4. $R_3$, $R_4$ and $R_8$ are independently hydrogen or lower alkyl, $R_5$ and $R_6$, independently are hydrogen or lower alkyl, $R_7$ is hydrogen, lower alkyl, cycloalkyl, Het-lower alkyl or aryl, Het is a monocyclic 5- or 6-membered hetero aromatic or a bicyclic heteroaromatic radical containing one or two hetero atoms selected from nitrogen, oxygen and sulfur, which radical may be substituted by lower alkyl, halogen or aryl, and the asterisk denotes the point of attachment, and their enantiomers, diastereomers and racemic mixtures thereof, as well as when *E is

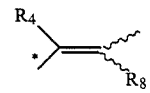

their geometric isomers and pharmaceutically acceptable acid addition salts thereof.

The compounds of formula 1 exhibit activity as paltelet activiating factor (PAF) antagonists and are, therefore, useful in disease states characterized by excess platelet activating factor or for the prevention and treatment of cardiovascular diseases, pulmonary diseases, immunological disorders, inflammatory diseases, dermatological disorders, shock or transplant rejection.

18 Claims, No Drawings

CYCLOPROYLPROPENAMIDES USEFUL AS PLATELET ACTIVING FACTOR (PAF) ANTAGONISTS

This is a division of application Ser. No. 72,390 filed July 10, 1987 now U.S. No. 4,786,646.

BRIEF SUMMARY OF THE INVENTION

The invention relates to compounds of the formula

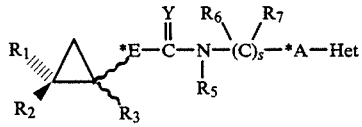

Y is O or S, *A is paraphenylene or *—$(CH_2)_n$—$(X)_m$—$(CH_2)_r$—, X is O, S or —CH=CH—, n or r, independently, are integers from 0 to 3, s is an integer from 0 to 1, m is an integer from 0 to 1, provided that when m is 1, n+s must be at least 2, $R_1$ and $R_2$, independently, are hydrogen, lower alkyl, cycloalkyl, lower alkenyl, Het or aryl, *E is

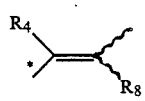

or —$(CH_2)_k$— wherein k is an integer from 0 to 4, $R_3$, $R_4$ and $R_8$ are independently hydrogen or lower alkyl, $R_5$ and $r_6$, independently are hydrogen or lower alkyl, $R_7$ is hydrogen, lower alkyl, cycloalkyl, Het-lower alkyl or aryl, Het is a monocyclic 5- or 6-membered hetero aromatic or a bicyclic heteroaromatic radical containing one or two hetero atoms selected from nitrogen, oxygen and sulfur, which radical may be substituted by lower alkyl, halogen or aryl, and the asterisk denotes the point of attachment, and their enantiomers, diastereomers and racemic mixtures thereof, as well as when *E is

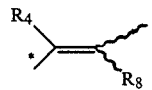

their geometric isomers, and pharmaceutically acceptable acid addition salts thereof.

The compounds of formula I exhibit activity as platelet activating factor (PAF) antagonists and are, therefore, useful in disease states characterized by excess platelet activating factor or for the prevention and treatment of cardiovascular diseases, pulmonary diseases, immunological disorders, inflammatory diseases, dermatological disorders, shock or transplant rejection.

DETAILED DESCRIPTION OF THE INVENTION

The invention relates to compounds of the formula

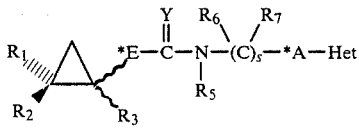

Y is O or S, *A is paraphenylene or *—$(CH_2)_n$—$(X)_m$—$(CH_2)_r$—, X is O, S or —CH=CH—, n or r, independently, are integers from 0 to 3, s is an integer from 0 to 1, m is an integer from 0 to 1, provided that when m is 1, n+s must be at least 2, $R_1$ and $R_2$, independently, are hydrogen, lower alkyl, cycloalkyl, lower alkenyl, Het or aryl, *E is

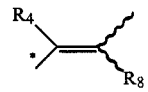

or —$(CH_2)_k$— wherein k is an integer from 0 to 4, $R_3$, $R_4$ and $R_8$ are independently hydrogen or lower alkyl, $R_5$ and $R_6$, independently are hydrogen or lower alkyl, $R_7$ is hydrogen, lower alkyl, cycloalkyl, Het-lower alkyl or aryl, Het is a monocyclic 5- or 6-membered hetero aromatic or a bicyclic heteroaromatic radical containing one or two hetero atoms selected from nitrogen, oxygen and sulfur, which radical may be substituted by lower alkyl, halogen or aryl, and the asterisk denotes the point of attachment, and their enantiomers, diastereomers and racemic mixtures thereof, as well as when *E is

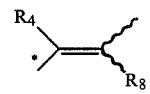

their geometric isomers, and pharmaceutically acceptable acid addition salts thereof.

As used herein, the term "alkyl" preferably denotes "lower alkyl", which denotes a straight or branched chain saturated hydrocarbon containing 1 to 7 carbon atoms, for example, methyl, ethyl, propyl, isopropyl, butyl, t-butyl, neopentyl, heptyl, and the like. The term "cycloalkyl" denotes a cyclic alkyl group of 3 to 6 carbon atoms, for example, cyclopropyl, cyclohexyl, and the like. The term "lower alkoxy" denotes an alkyl ether group which the alkyl group is as described above, for example, methoxy, ethoxy, propoxy, pentoxy and the like. The term "lower alkenyl" denotes a straight or branched chain unsaturated hydrocarbon containing 3 to 7 carbon atoms, for example, propenyl, butenyl and the like.

The term "halogen" denotes all the halogens, i.e., bromine, chlorine, fluorine, and iodine. The term "aryl" preferably denotes naphthalenyl, phenyl or phenyl or naphthalenyl mono-, di or trisubstituted by halogen, trifluoromethyl, lower alkyl, phenyl, lower alkoxy or nitro.

The term "Het" denotes a monocyclic 5- or 6-membered heteroaromatic or a bicyclic heteroaromatic radical containing one or two hetero atoms, selected from nitrogen, oxygen and sulfur, which radical may be substituted by lower alkyl, halogen or phenyl, for example, pyridinyl, quinolinyl, isoquinolyl, imidazolinyl, indolyl, benzimidazolinyl, thienyl, furyl, pyrimidinyl, oxazolinyl and the like.

The compounds of formula I can exist as enantiomers, diastereomers or racemic mixture. More specifically, the compounds of formula I have 1 to 3 asymmetric centers and therefor in addition to existing as enantiomers, they can exist as diastereomers. When *E is

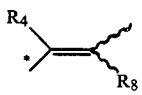

then the compounds of formula I can also exist as geometric isomers.

Examples of such compounds are:

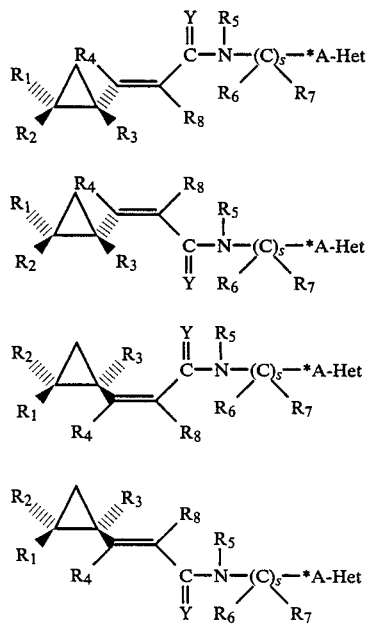

The invention encompasses all the isomers and mixtures thereof.

A preferred group of compounds of formula I are those wherein $R_1$ and $R_2$ are lower alkyl or aryl, $R_3$, $R_4$ and $R_8$ independently are hydrogen or lower alkyl, $R_5$ and $R_7$ are hydrogen, $R_6$ is hydrogen, lower alkyl or cycloalkyl, *A is $-(CH_2)_n-(X)_m-(CH_2)_r$ wherein $n+r=2$ to 6, $m=0$, Het is a monocyclic 5 or 6 membered heteroaromatic ring containing one or two heteroatoms selected from nitrogen, oxygen and sulfur, y is oxygen or sulfur, S is 1.

A more preferred group of formula I are those wherein $R_1$ is lower alkyl or aryl, $R_2$ is aryl, $R_3$, $R_4$ and $R_8$ are independently hydrogen or lower alkyl, *A is *—$(CH_2)_n$—X—$(CH_2)_r$ wherein $n+r=3$, $m=0$, Het is pyridinyl, or pyrimidinyl unsubstituted or substituted with lower alkyl, $R_5$ and $R_7$ are hydrogen, $R_6$ is hydrogen, lower alkyl or cyclopropyl, y is oxygen, s is 1, *E is

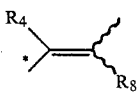

A most preferred group of compounds of formula I are those where $R_1$ and $R_2$ are phenyl with up to 3-substituents selected from halogen, or lower alkoxy, $R_3$, $R_4$, $R_5$, $R_7$ and $R_8$ are hydrogen, $R_6$ is hydrogen or lower alkyl, Het is 3-pyridinyl or 2-methyl-3-pyridinyl, *E is

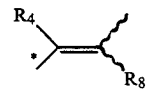

Preferred compounds of the invention are:

[S-(E)]-3-(2,2-diphenylcyclopropyl)-N-[4-(3-pyridinyl)butyl]-2-propenamide;
[R-(Z)]-3-(2,2-diphenylcyclopropyl)-N-[4-(3-pyridinyl)butyl]-2-propenamide;
[S-(E)]-3-[2,2-bis(3-fluorophenyl)cyclopropyl]-N-[4-(3-pyridinyl)butyl]-2-propenamide;
[S,R*-(E)]-3-[2,2-bis(3-fluorphenyl)cyclopropyl]-N-[1-methyl-4-(3-pyridinyl)butyl]-2-propenamide;
[1(R,S),2(R,S)-(E)]-3-[[2-(3-methoxyphenyl)-2-phenyl]-cyclopropyl]-N-[4-(3-pyridinyl)butyl]-2-propenamide;
[R,S-(E)]-3-(2,2-diphenylcyclopropyl)-N-[4-(3-pyridinyl)butyl]-2-propenethioamide.

Exemplary compounds of formula I of the invention are:

[S,R*-(E)]-3-(2,2-diphenylcyclopropyl)-N-[1-methyl-4-(3-pyridinyl)butyl]-2-propenamide;
[S-(E)-3-(2,2-diphenylcyclopropyl)-N-[4-(2-methyl-3-pyridinyl)butyl]-2-propenamide;
[S-(E)]-3-(2,2-diphenylcyclopropyl)-N-[4-(6-methyl-3-pyridinyl)butyl]-2-propenamide;
[S-(E)]-3-(2,2-diphenylcyclopropyl)-N-[5-(2-pyridinyl)pentyl]-2-propenamide;
[S-(E)]-3-(2,2-diphenylcyclopropyl)-N-[3-(4-pyridinyl)propyl]-2-propenamide;
[S-(E)]-3-(2,2-diphenylcyclopropyl)-N-[4-(3-furyl)butyl]-2-propenamide;
[S,R*-(E)]-3-(2,2-diphenylcyclopropyl)-N-[1-methyl-4-(3-furyl)butyl]-2-propenamide;
[S,-(E)]-3-(2,2-diphenylcyclopropyl)-N-[4-(3-thienyl)butyl]-2-propenamide;
[S,R*-(E)]-3-(2,2-diphenylcyclopropyl)-N-[1-methyl-4-(3-thienyl)butyl]-2-propenamide;
[S-(E)]-3-(2,2-diphenylcyclopropyl)-N-[4-(1,3-thiazol-2-yl)butyl]-2-propenamide;
[S,R*-(E)]-3-(2,2-diphenylcyclopropyl)-N-[1-ethyl-4-(1,3-thiazol-2-yl)butyl]-2-propenamide;
[S-(E)]-3-(2,2-diphenylcyclopropyl)-N-[4-(5-pyrimidinyl)butyl]-2-propenamide;
[S,R*-(E)]-3-(2,2-diphenylcyclopropyl)-N-[1-methyl-4-(5-pyrimidinyl)butyl]-2-propenamide;
[S-(E)]-3-(2,2-diphenylcyclopropyl)-N-[4-(2-imidazolyl)butyl]-2-propenamide;
[S,R*-(E)]-3-(2,2-diphenylcyclopropyl)-N-[1-methyl-4-(2-imidazolyl)butyl]-2-propenamide;
[S-(E)]-3-(2,2-diphenylcyclopropyl)-N-[4-(2H-pyrrol-3-yl)butyl]-2-propenamide;
[S,R*-(E)]-3-(2,2-diphenylcyclopropyl)-N-[1-methyl-4-(2H-pyrrol-3-yl)butyl]-2-propenamide;
[S-(E)]-3-(2,2-diphenylcyclopropyl)-N-[4-(3-pyridazinyl)butyl]-2-propenamide;
[S,R*-(E)]-3-(2,2-diphenylcyclopropyl)-N-[1-methyl-4-(5-pyridazinyl)butyl]-2-propenamide;
[S-(E)]-N-[4-(2H:chromen-3-yl)butyl]-3-(2,2-diphenylcyclopropyl)-2-propenamide;
[S,R*-(E)]-3-(2,2-diphenylcyclopropyl)-N-[1-methyl-4-(2H-chromen-3-yl)butyl]-2-propenamide;
[S-(E)]-3-(2,2-diphenylcyclopropyl)-N-[4-(3-pyridinyl)phenyl]-2-propenamide;
[S-(E)]-3-(2,2-diphenylcyclopropyl)-N-[(E)-4-(3-pyridinyl)-3-butenyl]-2-propenamide;

(S)-2,2-diphenyl-N-[4-(3-pyridinyl)butyl]cyclopropanecarboxamide;
(R)-2,2-diphenyl-N-[4-(3-pyridinyl)butyl]cyclopropanecarboxamide;
(S,R*)-2,2-diphenyl-N-[1-methyl-4-(3-pyridinyl)butyl]cyclopropanecarboxamide;
(S)-2,2-bis(3-fluorophenyl)-N-[4-(3-pyridinyl)butyl]cyclopropanecarboxamide;
(S)-2,2-bis(4-fluorophenyl)-N-[4-(3-pyridinyl)butyl]cyclopropanecarboxamide;
(S)-2,2-bis(3-methoxyphenyl)-N-[4-(3-pyridinyl)butyl]cyclopropanecarboxamide;
(S)-2,2-bis(4-methoxyphenyl)-N-[4-(3-pyridinyl)butyl]cyclopropanecarboxamide;
(S)-2,2-bis(3,4-dimethoxyphenyl)-N-[4-(3-pyridinyl)butyl]cyclopropanecarboxamide;
(S)-2,2-bis(3-chlorophenyl)-N-[4-(3-pyridinyl)butyl]cyclopropanecarboxamide;
(S)-2,2-bis[3-(trifluoromethyl)phenyl]-N-[4-(3-pyridinyl)butyl]-cyclopropanecarboxamide;
(S)-2,2-bis[3-(methylthio)phenyl]-N-[4-(3-pyridinyl)butyl]cyclopropanecarboxamide;
(S)-2,2-bis(3-methylphenyl)-N-[4-(3-pyridinyl)butyl]cyclopropanecarboxamide;
(S)-2,2-diphenyl-N-[4-(3-pyridinyl)butyl]cyclopropaneacetamide;
(R)-2,2-diphenyl-N-[4-(3-pyridinyl)butyl]cyclopropaneacetamide;
(S,R*)-2,2-diphenyl-N-[1-methyl-4-(3-pyridinyl)butyl]cyclopropaneacetamide;
(S)-2,2-bis(3-fluorophenyl)-N-[4-(3-pyridinyl)butyl]cyclopropaneacetamide;
(S)-2,2-bis(4-fluorophenyl)-N-[4-(3-pyridinyl)butyl]cyclopropaneacetamide;
(S)-2,2-bis(3-methoxyphenyl)-N:[3-pyridinyl)butyl]cyclopropaneacetamide;
(S)-2,2-bis(4-methoxyphenyl)-N-[4-(3-pyridinyl)butyl]cyclopropaneacetamide;
(S)-2,2-bis(3,4-dimethoxyphenyl)-N-[4-(3-pyridinyl)butyl]cyclopropaneacetamide;
(S)-2,2-bis(3-chlorophenyl)-N-[4-(3-pyridinyl)butyl]cyclopropaneacetamide;
(S)-2,2-bis[3-fluorophenyl)-N-[4-(3-pyridinyl)butyl]cyclopropanepropanamide;
(S)-2,2-bis(3-methoxyphenyl)-N-[4-(3-pyridinyl)butyl]cyclopropanepropanamide;
(S)-2,2-bis(3-fluorophenyl)-N-[4-(3-pyridinyl)butyl]cyclopropanebutanamide;
[S,R*-(E)]-3-[2,2-bis(3-fluorophenyl)cyclopropyl]-N-[1-methyl-4-(3-pyridinyl)butyl]-2-propenamide;
[S-(E)]-3-[2,2-bis(3-fluorophenyl)cyclopropyl]-N-[4-(2-methyl-3-pyridinyl)butyl]-2-propenamide;
[S-(E)]-3-[2,2-bis(3-fluorophenyl)cyclopropyl]-N-[4-(6-methyl-3-pyridinyl)butyl]-2-propenamide;
[S-(E)]-3-[2,2-bis(3-fluorophenyl)cyclopropyl]-N-[5-(2-pyridinyl)pentyl]-2-propenamide;
[S-(E)]-3-[2,2-bis(3-fluorophenyl)cyclopropyl]-N-[3-(4-pyridinyl)propyl]-2-propenamide;
[S-(E)]-3-[2,2-bis(3-fluorophenyl)cyclopropyl]-N-[4-(3-furyl)butyl]-2-propenamide;
[S,R*-(E)]-3-[2,2-bis(3-fluorophenyl)cyclopropyl]-N-[1-methyl-4-(3-furyl)butyl]-2-propenamide;
[S,-(E)]-3-[2,2-bis(3-fluorophenyl)cyclopropyl]-N-[4-(3-thienyl)butyl]-2-propenamide;
[S,R*-(E)]-3-[2,2-bis(3-fluorophenyl)cyclopropyl]-N-[1-methyl-4-(3-thienyl)butyl]-2-propenamide;
[S-(E)]-3-[2,2-bis(3-fluorophenyl)cyclopropyl]-N-[4-(1,3-thiazol-2-yl)butyl]-2-propenamide;
[S,R*-(E)]-3-[2,2-bis(3-fluorophenyl)cyclopropyl]-N-[1-ethyl-4-(1,3-thiazol-2-yl)butyl]-2-propenamide;
[S-(E)]-3-[2,2-bis(3-fluorophenyl)cyclopropyl]-N-[4-(5-pyrimidinyl)butyl]-2-propenamide;
[S,R*-(E)]-3-[2,2-bis(3-fluorophenyl)cyclopropyl]-N-[1-methyl-4-(5-pyrimidinyl)butyl]-2-propenamide;
[S-(E)]-N-[4-(2-imidazolyl)butyl]-3-[2,2-bis(3-fluorophenyl)cyclopropyl]-2-propenamide;
[S,R*-(E)]-3-[2,2-bis(3-fluorophenyl)cyclopropyl]-N-[1-methyl-4-(2-imidazolyl)butyl]-2-propenamide;
[S-(E)]-3-[2,2-bis(3-fluorophenyl)cyclopropyl]-N-[4-(2H-pyrrol-3-yl)butyl]-2-propenamide;
[S,R*-(E)]-3-[2,2-bis(3-fluorophenyl)cyclopropyl]-N-[1-methyl-4-(2H-pyrrol-3-yl)butyl]-2-propenamide;
[S-(E)]-3-[2,2-bis(3-fluorophenyl)cyclopropyl]-N-[4-(3-pyridazinyl)butyl]-2-propenamide;
[S,R*-(E)]-3-[2,2-bis(3-fluorophenyl)cyclopropyl]-N-[1-methyl-4-(5-pyridazinyl)butyl]-2-propenamide;
[S-(E)]-N-[4-(2H-chromen-3-yl)butyl]-3-[2,2-bis(3-fluorophenyl)cyclopropyl]-2-propenamide;
[S,R*-(E)]-3-[2,2-bis(3-fluorophenyl)cyclopropyl]-N-[1-methyl-4-(2H-chromen-3-yl)butyl]-2-propenamide;
[S-(E)]-3-[2,2-bis(3-fluorophenyl)cyclopropyl]-N-[4-(3-pyridinyl)phenyl]-2-propenamide;
[S-(E)-3-[2,2-bis(3-fluorophenyl)cyclopropyl]-N-[(E)-4-(3-pyridinyl)-3-butenyl]-2-propenamide;
[S,R*-(E)]-3-[2,2-bis(4-fluorophenyl)cyclopropyl]-N-[1-methyl-4-(3-pyridinyl)butyl]-2-propenamide;
[S-(E)]-3-[2,2-bis(4-fluorophenyl)cyclopropyl]-N-[4-(2-methyl-3-pyridinyl)butyl]-2-propenamide;
[S-(E)]-3-[2,2-bis(4-fluorophenyl)cyclopropyl]-N-[4-(6-methyl-3-pyridinyl)butyl]-2-propenamide;
[S-(E)]-3-[2,2-bis(4-fluorophenyl)cyclopropyl]-N-[5-(2-pyridinyl)pentyl]-2-propenamide;
[S-(E)]-3-[2,2-bis(4-fluorophenyl)cyclopropyl]-N-[3-(4-pyridinyl)propyl]-2-propenamide;
[S-(E)]-3-[2,2-bis(4-fluorophenyl)cyclopropyl]-N-[4-(3-furyl)butyl]-2-propenamide;
[S,R*-(E)]-3-[2,2-bis(4-fluorophenyl)cyclopropyl]-N-[1-methyl-4-(3-furyl)butyl]-2-propenamide;
[S,-(E)]-3-[2,2-bis(4-fluorophenyl)cyclopropyl]-N-[4-(3-thienyl)butyl]-2-propenamide;
[S,R*-(E)]-3-[2,2-bis(4-fluorophenyl)cyclopropyl]-N-[1-methyl-4-(3-thienyl)butyl]-2-propenamide;
[S-(E)]-3-[2,2-bis(4-fluorophenyl)cyclopropyl]-N-[4-(1,3-thiazol-2-yl)butyl]-2-propenamide;
[S,R*-(E)]-3-[2,2-bis(4-fluorophenyl)cyclopropyl]-N-[1-ethyl-4-(1,3-thiazol-2-yl)butyl]-2-propenamide;
[S-(E)]-3-[2,2-bis(4-fluorophenyl)cyclopropyl]-N-[4-(5-pyrimidinyl)butyl]-2-propenamide;
[S,R*-(E)]-3-[2,2-bis(4-fluorophenyl)cyclopropyl]-N-[1-methyl-4-(5-pyrimidinyl)butyl]-2-propenamide;
[S-(E)]-N-[4-(2-imidazolyl)butyl]-3-[2,2-bis(4-fluorophenyl)cyclopropyl]-2-propenamide;
[S,R*-(E)]-3-[2,2-bis(4-fluorophenyl)cyclopropyl]-N-[1-methyl-4-(2-imidazolyl)butyl]-2-propenamide;
[S-(E)]-3-[2,2-bis(4-fluorophenyl)cyclopropyl]-N-[4-(2H-pyrrol-3-yl)butyl]-2-propenamide;
[S,R*-(E)]-3-[2,2-bis(4-fluorophenyl)cyclopropyl]-N-[1-methyl-4-(2H-pyrrol-3-yl)butyl]-2-propenamide;
[S-(E)]-3-[2,2-bis(4-fluorophenyl)cyclopropyl]-N-[4-(3-pyridazinyl)butyl]-2-propenamide;
[S,R*-(E)]-3-[2,2-bis(4-fluorophenyl)cyclopropyl]-N-[1-methyl-4-(5-pyridazinyl)butyl]-2-propenamide;
[S-(E)]-N-[4-(2H-chromen-3-yl)butyl]-3-[2,2-bis(4-fluorophenyl)cyclopropyl]-2-propenamide;

[S,R*-(E)]-3-[2,2-bis(4-fluorophenyl)cyclopropyl]-N-[1-methyl-4-(2H-chromen-3-yl)butyl]-2-propenamide;

[S-(E)]-3-[2,2-bis(4-fluorophenyl)cyclopropyl]-N-[4-(3-pyridinyl)phenyl]-2-propenamide;

[S-(E)]-3-[2,2-bis(4-fluorophenyl)cyclopropyl]-N-[(E)-4-(3-pyridinyl)-3-butenyl]-2-propenamide;

[S,R*-(E)]-3-[2,2-bis(3-methoxyphenyl)cyclopropyl]-N-[1-methyl-4-(3-pyridinyl)butyl]-2-propenamide;

[S-(E)-3-[2,2-bis(3-methoxyphenyl)cyclopropyl]-N-[4-(2-methyl-3-pyridinyl)butyl]-2-propenamide;

[S-(E)]-3-[2,2-bis(3-methoxyphenyl)cyclopropyl]-N-[4-(6-methyl-3-pyridinyl)butyl]-B 2-propenamide;

[S-(E)]-3-[2,2-bis(3-methoxyphenyl)cyclopropyl]-N-[5-(2-pyridinyl)pentyl]-2-propenamide;

[S-(E)]-3-[2,2-bis(3-methoxyphenyl)cyclopropyl]-N-[3-(4-pyridinyl)propyl]-2-propenamide;

[S-(E)]-N-[4-(3-furyl)butyl]-3-[2,2-bis(3-methoxyphenyl)cyclopropyl]-2-propenamide;

[S,R*-(E)]-3-[2,2-bis(3-methoxyphenyl)cyclopropyl]-N-[1-methyl-4-(3-furyl)butyl]-2-propenamide;

[S,-(E)]-3-[2,2-bis(3-methoxyphenyl)cyclopropyl]-N-[4-(3-thienyl)butyl]-2-propenamide;

[S,R*-(E)]-3-[2,2-bis(3-methoxyphenyl)cyclopropyl]-N-[1-methyl-4-(3-thienyl)butyl]-2-propenamide;

[S-(E)]-3-[2,2-bis(3-methoxyphenyl)cyclopropyl]-N-[4-(1,3-thiazol-2-yl)butyl]-2-propenamide;

[S,R*-(E)]-3-[2,2-bis(3-methoxyphenyl)cyclopropyl]-N-[1-methyl-4-(1,3-thiazol-2-yl)butyl]-2-propenamide;

[S-(E)]-3-[2,2-bis(3-methoxyphenyl)cyclopropyl]-N-[4-(5-pyrimidinyl)butyl]-2-propenamide;

[S,R*-(E)]-3-[2,2-bis(3-methoxyphenyl)cyclopropyl]-N-[1-methyl-4-(5-pyrimidinyl)butyl]-2-propenamide;

[S-(E)]-N-[4-(2-imidazolyl)butyl]-3-[2,2-bis(3-methoxyphenyl)cyclopropyl]-2-propenamide;

[S,R*-(E)]-3-[2,2-bis(3-methoxyphenyl)cyclopropyl]-N-[1-methyl-4-(2-imidazolyl)butyl]-2-propenamide;

[S-(E)]-3-[2,2-bis(3-methoxyphenyl)cyclopropyl]-N-[4-(2H-pyrrol-3-yl)butyl]-2-propenamide;

[S,R*-(E)]-3-[2,2-bis(3-methoxyphenyl)cyclopropyl]-N-[1-methyl-4-(2H-pyrrol-3-yl)butyl]-2-propenamide;

[S-(E)]-3-[2,2-bis(3-methoxyphenyl)cyclopropyl]-N-[4-(3-pyridazinyl)butyl]-2-propenamide;

[S,R*-(E)]-3-[2,2-bis(3-methoxyphenyl)cyclopropyl]-N-[1-methyl-4-(5-pyridazinyl)butyl]-2-propenamide;

[S-(E)]-N-[4-(2H-chromen-3-yl)butyl]-3-[2,2-bis(3-methoxyphenyl)cyclopropyl]-2-propenamide;

[S,R*-(E)]-3-[2,2-bis(3-methoxyphenyl)cyclopropyl]-N-[1-methyl-4-(2H-chromen-3-yl)butyl]-2-propenamide;

[S-(E)]-3-[2,2-bis(3-methoxyphenyl)cyclopropyl]-N-[4-(3-pyridinyl)phenyl]-2-propenamide;

[S-(E)]-3-[2,2-bis(3-methoxyphenyl)cyclopropyl]-N-[(E)-4-(3-pyridinyl)-3-butenyl]-2-propenamide;

[S-(E)]-[[2,2-bis(4-methoxyphenyl)cyclopropyl]-N-[4-(2-methyl-3-pyridinyl)butyl]-2-propenamide;

[S-(E)]-3-[2,2-bis(4-methoxyphenyl)cyclopropyl]-N-[4-(6-methyl-3-pyridinyl)butyl]-2-propenamide;

[S-(E)]-3-[2,2-bis(4-methoxyphenyl)cyclopropyl]-N-[5-(2-pyridinyl)pentyl]-2-propenamide;

[S-(E)]-3-[2,2-bis(4-methoxyphenyl)cyclopropyl]-N-[3-(4-pyridinyl)propyl]-2-propenamide;

[S-(E)]-N-[4-(3-furyl)butyl]-3-[2,2-bis(4-methoxyphenyl)cyclopropyl]-2-propenamide;

[S-(E)]-3-[2,2-bis(4-methoxyphenyl)cyclopropyl]-N-[4-(3-thienyl)butyl]-2-propenamide;

[S-(E)]-3-[2,2-bis(4-methoxyphenyl)cyclopropyl]-N-[4-(1,3-thiazol-2-yl)butyl]-2-propenamide;

[S-(E)]-3-[2,2-bis(4-methoxyphenyl)cyclopropyl]-N-[4-(5-pyrimidinyl)butyl]-2-propenamide;

[S-(E)]-N-[4-(2-imidazolyl)butyl]-3-[2,2-bis(4-methoxyphenyl)cyclopropyl]-2-propenamide;

[S-(E)]-3-[2,2-bis(4-methoxyphenyl)cyclopropyl]-N-[4-(2H-pyrrol-3-yl)butyl]-2-propenamide;

[S-(E)]-3-[2,2-bis(4-methoxyphenyl)cyclopropyl]-N-[4-(3-pyridazinyl)butyl]-2-propenamide;

[S-(E)]-N-[4-(2H-chromen-3-yl)butyl]-3-[2,2-bis(4-methoxyphenyl)cyclopropyl]-2-propenamide;

[S-(E)]-3-[2,2-bis(4-methoxyphenyl)cyclopropyl]-N-[4-(3-pyridinyl)phenyl]-2-propenamide;

[S-(E)]-3-[2,2-bis(4-methoxyphenyl)cyclopropyl]-N-[(E)-4-(3-pyridinyl)-3-butenyl]-2-propenamide;

[1S,2S-(E)]-3-[[2-(3-methoxyphenyl)-2-phenyl]cyclopropyl]-N-[4-(3-pyridinyl)butyl]-2-propenamide;

[1S,2S-(E)]-3-[[2-(3-methoxyphenyl)-2-phenyl]cyclopropyl]-N-[4-(3-thienyl)butyl]-2-propenamide;

[1S,2S-(E)]-3-[[2-(3-methoxyphenyl)-2-phenyl]cyclopropyl]-N-[4-(1,3-thiazol-2-yl)butyl]-2-propenamide;

[1S,2S-(E)]-3-[[2-(3-methoxyphenyl)-2-phenyl]cyclopropyl]-N-[4-(5-pyrimidinyl)butyl]-2-propenamide;

[1S,2S-(E)]-N-[4-(2-imidazolyl)butyl]-3-[[2-(3-methoxyphenyl)-2-phenyl]cyclopropyl]-2-propenamide;

[1S,2S-(E)]-3-[[2-(3-methoxyphenyl)-2-phenyl]cyclopropyl]-N-[4-(2H-pyrrol-3-yl)butyl]-2-propenamide;

[1S,2S-(E)]-3-[[2-(3-methoxyphenyl)-2-methyl]cyclopropyl]-N-[4-(3-pyridinyl)phenyl]-2-propenamide;

[1S,2S-(E)]-3-[[2-ethyl-2-(3-methoxyphenyl)]cyclopropyl]-N-[4-(3-pyridinyl)phenyl]-2-propenamide;

[1S,2S-(E)]-3-[[2-(3-methoxyphenyl)-2-propyl]cyclopropyl]-N-[4-(3-pyridinyl)phenyl]-2-propenamide;

[1S,2S-(E)]-3-[[2-(3-methoxyphenyl)-2-(2-thienyl)]cyclopropyl]-N-[4-(3-pyridinyl)phenyl]-2-propenamide;

[1S,2S-(E)]-3-[[2-butyl-2-phenyl)]cyclopropyl]-N-[4-(3-pyridinyl)butyl]-2-propenamide;

[1S,2S-(E)]-3-[[2-butyl-2-(4-methoxyphenyl)]cyclopropyl]-N-[4-(3-pyridinyl)butyl]-2-propenamide;

[1S,2S-(E)]-3-[[2-butyl-2-(3-fluorophenyl)]cyclopropyl]-N-[4-(3-pyridinyl)butyl]-2-propenamide;

[1R,2S-(Z)]-3-[[2-(3-fluorophenyl)-2-phenyl]cyclopropyl]-N-[4-(3-pyridinyl)butyl]-2-propenamide;

[1S,2S-(E)]-3-[[2-(3-fluorophenyl)-2-pentyl]cyclopropyl]-N-[4-(3-pyridinyl)butyl]-2-propenamide;

[1S,2R-(E)]-3-[[2-(3-fluorophenyl)-2-pentyl]cyclopropyl]-N-[4-(3-pyridinyl)butyl]-2-propenamide;

[1R,2S-(Z)]-3-[[2-(3-fluorophenyl)-2-pentyl]cyclopropyl]-N-[4-(3-pyridinyl)butyl]-2-propenamide;

[1R,2R-(Z)]-3-[[2-(3-fluorophenyl)-2-pentyl]cyclopropyl]-N-[4-(3-pyridinyl)butyl]-2-propenamide;

[1S,2S-(E)]-3-[[2-(3-fluorophenyl)-2-hexyl]cyclopropyl]-N-[4-(3-pyridinyl)butyl]-2-propenamide;

[1S,2S-(E)]-3-[[2-(3-fluorophenyl)-2-heptyl]cyclopropyl]-N-[4-(3-pyridinyl)butyl]-2-propenamide;

[1S,2S-(E)]-3-[[2-(3-fluorophenyl)-2-pentyl]cyclopropyl]-N-[4-(3-pyridinyl)butyl]-2-propenamide;

[1S,2S-(E)]-3-[[2-(4-fluorophenyl)-2-pentyl]cyclopropyl]-N-[4-(3-pyridinyl)butyl]-2-propenamide;

[1S,2S-(E)]-3-[[2-(3-methoxyphenyl)-2-pentyl]cyclopropyl]-N-[4-(3-pyridinyl)butyl]-2-propenamide;

[1S,2S-(E)]-3-[[2-(3-fluorophenyl)-2-pentyl]cyclopropyl]-N-[4-(3-pyridinyl)butyl]-2-propenethioamide;

[1S,2S-(E)]-3-[[2-pentyl-(3-pyridinyl)]cyclopropyl]-N-[4-(3-pyridinyl)butyl]-2-propenamide;

[1S,2S-(E)]-3-[[2-cyclohexyl-2-pentyl)cyclopropyl]-N-[4-(3-pyridinyl)butyl]-2-propenamide;
[1S,2S-(E)]-3-[[2-pentyl-2-(3-thienyl)]cyclopropyl]-N-[4-(3-pyridinyl)butyl]-2-propenamide;
(1S,2S)-3-[2-(3-fluorophenyl)-2-pentyl]-N-[4-(3-pyridinyl)butyl]cyclopropanecarboxamide;
(1S,2S)-3-[2-(3-fluorophenyl)-2-pentyl]-N-[4-(3-pyridinyl)butyl]-2-cyclopropaneacetamide;
(1S,2S)-3-[2-(3-fluorophenyl)-2-pentyl]-N-[4-(3-pyridinyl)butyl]cyclopropanepropanamide;
(1S,2S)-3-[2-(4-fluorophenyl)-2-pentyl]-N-[4-(3-pyridinyl)butyl]cyclopropanepropanamide;
(1S,2S)-3-[2-(3-methoxyphenyl)-2-pentyl]-N-[4-(3-pyridinyl)butyl]cyclopropanepropanamide;
(1S,2S)-3-[2-(3-fluorophenyl)-2-pentyl]-N-[4-(3-pyridinyl)butyl]cyclopropanepropanthioamide;
(1S,2S)-3-[2-(3-fluorophenyl)-2-cyclopentyl]-N-[4-(3-pyridinyl)butyl]cyclopropanepropanamide;
(1S,2)-3-[2-(3-fluorophenyl)-2-cyclohexyl]-N-[4-(3-pyridinyl)butyl]cyclopropanepropanamide;
(1S,2S)-3-[2-(3-fluorophenyl)-2-pentyl]-N-[4-(3-pyridinyl)butyl]cyclopropanebutanamide.

The compounds of formula I can be prepared as hereinafter described in Reaction Schemes I–XIII.

Reaction Scheme I

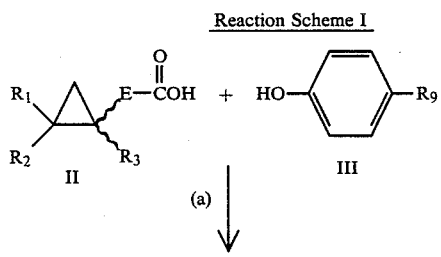

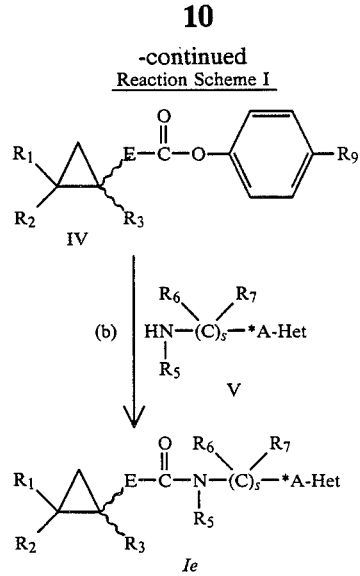

wherein $R_1$, $R_2$, $R_3$, $R_5$, $R_6$, $R_7$, *A, E, Het and s, are as previously described and $R_9$ is hydrogen, halogen, lower alkyloxy, lower alkyl, trihaloalkyl or nitro.

In Reaction Scheme I, step (a), a carboxylic acid of formula II which includes as appropriate, all enantiomeric or diastereomeric and/or geometric isomers and mixtures thereof is reacted with a phenol of formula III in the presence of a condensing agent, preferably dicyclohexylcarbodiimide, in an inert solvent such as dichloromethane, diethyl ether, dimethylformamide at a temperature of from −80° C. to room temperature. The resulting compounds of formula IV can be isolated utilizing conventional methods, for example, crystallization, chromatography or the like.

In step (b), an "activated" ester of formula IV is reacted with an amine of formula V, which includes the (R)- and (S)-enantiomers and racemic mixtures thereof, in an inert solvent, preferably tetrahydrofuran and diethyl ether, at a temperature of from −80° C. to 100° C. The process is advantageously carried out wherein $R_9$ is nitro. The resulting compound of formula Ie can be isolated utilizing conventional means, for example, crystallization, chromatography or the like.

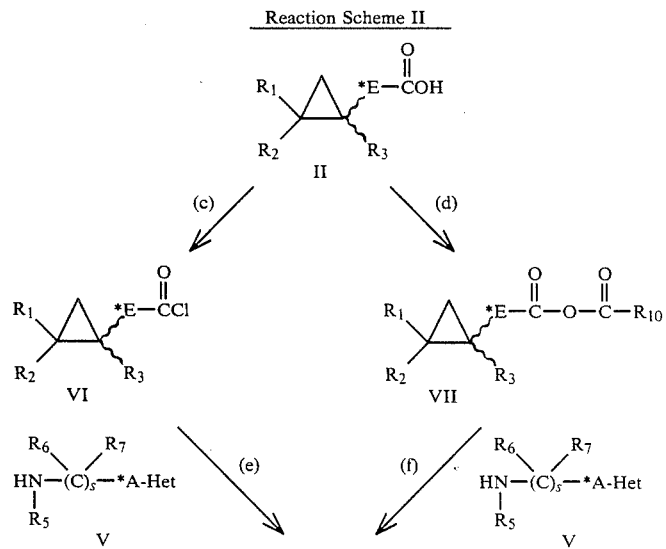

Reaction Scheme II

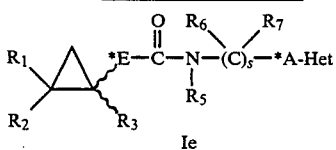

wherein $R_1$, $R_2$, $R_3$, $R_5$, $R_6$, $R_7$, *A, *E, Het and s are as previously described and $R_{10}$ is lower alkyl.

In Reaction Scheme II, step (c), a carboxylic acid of formula II which includes as appropriate, all enantiomeric or diastereomeric and/or geometric isomers and mixtures thereof, is treated with an acyl halide forming reagent, preferably oxalyl chloride or thionyl chloride, in an inert solvent, preferably dichloromethane or toluene at a temperature of from −80° C. to room temperature. The resulting corresponding compound of formula VI can be isolated by evaporation of the reaction solvent and then, as in step (e), are treated with an amine of structure V which includes the (R)-and (S)-enantiomers and racemic mixtures thereof, in the presence of a tertiary amine, preferably triethylamine, in an inert solvent such as dichloromethane or toluene at a temperature of from −80° C. to room temperature. The resulting compound of formula Ie can be isolated utilizing conventional methods such as crystallization or chromatography or the like.

In step (d), a carboxylic acid of formula II, which includes as appropriate, all enantiomeric or diastereomeric and/or geometric isomers and mixtures thereof, is treated with an alkyl chloroformate in the presence of a tertiary amine, preferably triethylamine, in an inert solvent, preferably diethyl ether or tetrahydrofurane at a temperature of from −20° C. to 10° C. The resulting mixed anhydride of formula VII is treated in situ as in step (f) with an amine of formula V which includes the (R)- and (S)-enantiomers and racemic mixtures thereof at a temperature of from −20° C. to room temperature. The resulting compound of formula Ie can be isolated utilizing conventional methods such as crystallization and chromatography or the like.

Reaction Scheme III

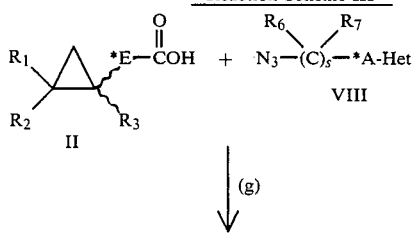

-continued
Reaction Scheme III

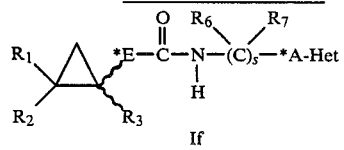

wherein $R_1$, $R_2$, $R_3$, $R_6$, $R_7$, *A, *E, Het and s are as previously described.

In Reaction Scheme III, step (g), a carboxylic acid of formula II which includes as appropriate, all enantiomeric or diastereomeric and/or geometric isomers and mixtures thereof, is reacted with an azide of formula VIII in the presence of a trialkyl or triarylphosphine in an inert solvent, preferably toluene at a temperature of from room temperature to 100° C. The resulting desired compound of formula If can be isolated utilizing conventional methods such as crystallization, chromatography or the like.

Reaction Scheme IV

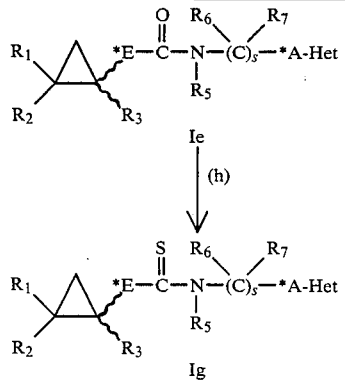

wherein $R_1$, $R_2$, $R_3$, $R_5$, $R_6$, $R_7$, *A, *E, Het and s are as previously described.

In Reaction Scheme IV, steph (h), a carboxamide of formula Ie, which includes as appropriate, all enantiomeric or diastereomeric and/or geometric isomers is reacted with phosphorous pentasulfide in a inert solvent, such as benzene, toluene or dichloromethane, optionally in the presence of a tertiary amine base such as triethylamine at temperatures of from 0° C. to 100° C. The resulting compound of formula Ig can be isolated utilizing conventional methods such as crystallization, chromatography and the like.

Reaction Scheme V

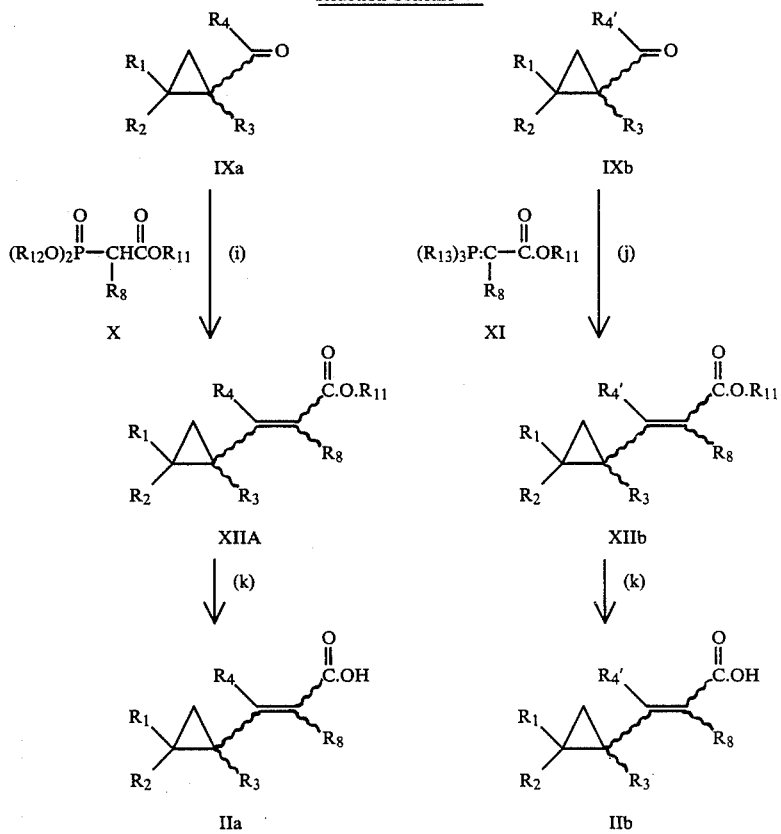

wherein $R_1$, $R_2$, $R_3$, $R_4$ and $R_8$ are as previously described, $R_4$, is hydrogen, $R_{11}$ and $R_{12}$ are lower alkyl, $R_{13}$ is alkyl, cycloalkyl or aryl.

In Reaction Scheme V, step (i), a phosphonoacetate triester of formula X is converted to its corresponding carbanion utilizing a strong base, preferably sodium hydride or sodium amide, in an inert solvent, preferably dimethylsulfoxide, dimethylformamide or tetrahydrofuran at temperatures of from 0° C. to 80° C., and then is reacted in situ with a carbonyl derivative of formula IXa, which includes as appropriate all enantiomeric or diastereoisomeric forms and mixtures thereof. The resulting compound of formula XIIa, may be a mixture of geometric isomers, can be separated, if necessary, utilizing conventional methods such as crystallization, chromatography or the like.

In step (j), a carboxaldehyde of formula IXb which includes as appropriate all enantiomeric or diastereoisomeric forms and mixtures thereof is reacted with (carboxalkoxyalkylidene)triarylphosphorane in an appropriate solvent at a temperature of from −20° C. to 50° C. Use of an aprotic solvent, preferably dichloromethane, carbon tetrachloride or dimethylformamide leads to an isomer ratio of >10:1 in favor of the (E)-isomer around the newly formed double bond. When a protic solvent is used as reaction solvent, preferably methanol or ethanol, a higher proportion of the (Z)-isomer is formed (E:Z; 3:2). The resulting compound of formula XIIb may be separated, if necessary, into the (E)- and (Z)-isomers by conventional methods such as crystallization, chromatography or the like.

In step (k), the carboxylic acid esters of formula XIIa or b are reacted with an excess of an alkali metal hydroxide in a solvent mixture preferably methanol-water or ethanol-water at a temperature of from room temperature to 85° C. The resulting compound of formula IIa or b is isolated by conventional methods such as chromatography or the like.

Compounds of formula XIIa or XIIb may have one or two chiral centers and one site of geometrical isomerism. Accordingly, from one to four racemic forms of XIIa or XIIb can exist. When either XIIa or XIIb is produced in more than one racemic form, in step (i) or (j), it is advantageous to separate the various racemic forms prior to step (k) by conventional methods, most often, chromatography. In this way, the carboxylic acids IIa or IIb, obtained from step (k) are pure racemates, which then may be resolved into their pure enaniomeric or diastereomeric forms by conventional methods, for example conversion to the salts of optically pure chiral amines such as cinchonidine, alpha-methyl-p-nitrobenzylamine and the like. The pure diastereoisomeric salts are obtained by fractional crystallization from an appropriate solvent, for example, a lower alkanol. The enaniomerically or diastereoisomerically pure acids may be recovered from their salts by conventional methods, for example, by extraction from an aqueous, acid solution.

REACTION SCHEME VI

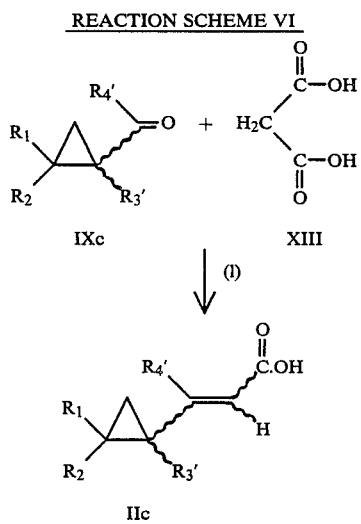

Wherein $R_1$ and $R_2$ are as previously described and $R_3$, and $R_4$, are hydrogen.

In Reaction Scheme VI, step (l), a carboxaldehyde of formula IXc, which includes as appropriate, all enantiomeric or diastereoisomeric isomers or racemic mixtures thereof, is reacted with malonic acid in a aprotic basic solvent, preferably pyridine and optionally in the presence of a catalytic amount of a secondary amine base such as pyrrolidine at temperatures of from room temperature to reflux temperature. The resulting compounds of formula IIc can be isolated utilizing conventional methods such as crystallization, chromatography and the like.

REACTION SCHEME VII

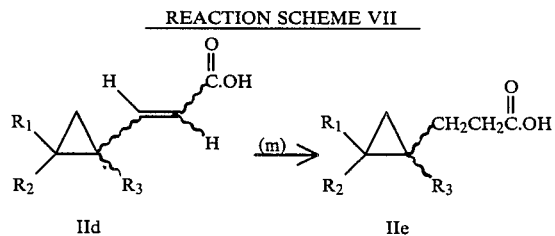

Wherein $R_1$, $R_2$ and $R_3$ are as previously described.

In Reaction Scheme VII, a carboxylic acid of formula IId, which includes as appropriate, all enantiomeric or diastereoisomeric forms and/or geometric isomers, or mixtures thereof, is hydrogenated over a suitable catalyst, for example, palladium on carbon, platinum oxide or Raney nickel, in a suitable solvent, for example, a lower alkanol, at a hydrogen pressure of from one to five atmospheres until the theoretical amount of hydrogen is taken up to give a compound of formula IIe.

REACTION SCHEME VIII

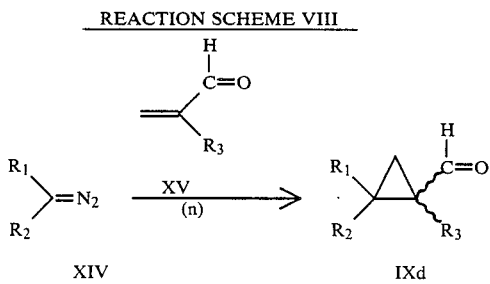

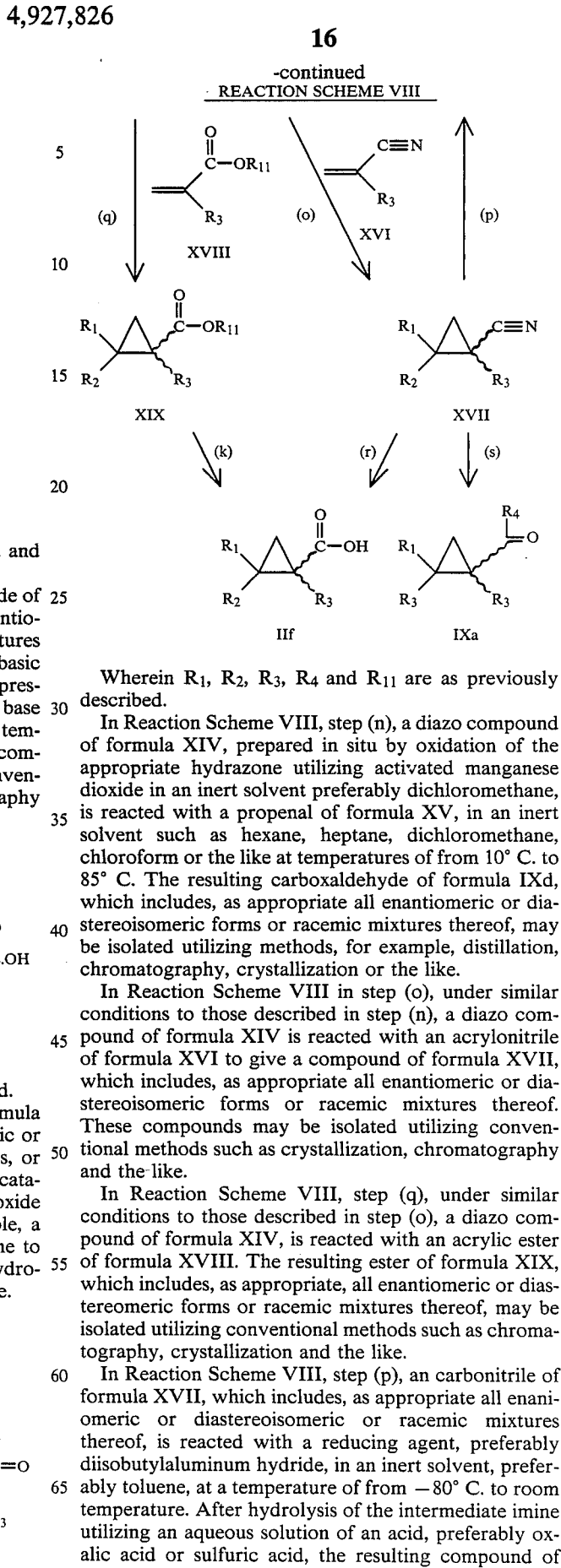

Wherein $R_1$, $R_2$, $R_3$, $R_4$ and $R_{11}$ are as previously described.

In Reaction Scheme VIII, step (n), a diazo compound of formula XIV, prepared in situ by oxidation of the appropriate hydrazone utilizing activated manganese dioxide in an inert solvent preferably dichloromethane, is reacted with a propenal of formula XV, in an inert solvent such as hexane, heptane, dichloromethane, chloroform or the like at temperatures of from 10° C. to 85° C. The resulting carboxaldehyde of formula IXd, which includes, as appropriate all enantiomeric or diastereoisomeric forms or racemic mixtures thereof, may be isolated utilizing methods, for example, distillation, chromatography, crystallization or the like.

In Reaction Scheme VIII in step (o), under similar conditions to those described in step (n), a diazo compound of formula XIV is reacted with an acrylonitrile of formula XVI to give a compound of formula XVII, which includes, as appropriate all enantiomeric or diastereoisomeric forms or racemic mixtures thereof. These compounds may be isolated utilizing conventional methods such as crystallization, chromatography and the like.

In Reaction Scheme VIII, step (q), under similar conditions to those described in step (o), a diazo compound of formula XIV, is reacted with an acrylic ester of formula XVIII. The resulting ester of formula XIX, which includes, as appropriate, all enantiomeric or diastereomeric forms or racemic mixtures thereof, may be isolated utilizing conventional methods such as chromatography, crystallization and the like.

In Reaction Scheme VIII, step (p), an carbonitrile of formula XVII, which includes, as appropriate all enantiomeric or diastereoisomeric or racemic mixtures thereof, is reacted with a reducing agent, preferably diisobutylaluminum hydride, in an inert solvent, preferably toluene, at a temperature of from −80° C. to room temperature. After hydrolysis of the intermediate imine utilizing an aqueous solution of an acid, preferably oxalic acid or sulfuric acid, the resulting compound of formula IXd, which includes all enantiomeric or diastereoisomeric forms or racemic mixtures thereof, may be isolated utilizing conventional methods, such as crystallization, chromatography, distillation and the like.

In Reaction Scheme VIII, step (s), a carbonitrile of formula XVII, which includes, as appropriate, all enantiomeric or diastereoisomeric forms or racemic mixtures thereof, is reacted with an alkyl or aryl magnesium halide, in an inert solvent preferably diethyl ether or tetrahydrofuran at a temperature of from −80° C. to reflux temperature. After hydrolysis of the intermediate imine, utilizing an aqueous solution of an acid, preferably oxalic acid or sulfuric acid, the resulting compound of formula IXa, which includes, as appropriate all enantiomeric or diastereoisomeric or racemic mixtures thereof, can be isolated utilizing conventional methods such as distillation, crystallization, chromatography and the like.

In Reaction Scheme VIII, step (r), a carbonitrile of formula XVII, which includes, as appropriate, all enaniomeric or diastereoisomeric or racemic mixtures thereof, is hydrolyzed to a compound of formula IIf, by treatment with an excess of an alkali metal hydroxide, such as sodium hydroxide or potassium hydroxide, in a water-lower alkanol solvent mixture at a temperature of from 50° C. to reflux. The compounds of formula IIf, which include, as appropriate, all enantiomeric or diastereoisomeric or racemic mixtures thereof, may be isolated utilizing conventional methods such as, crystallization, chromatography and the like.

In this Reaction Scheme, step (k) is the same step (k) as described in Reaction Scheme V, to give a compound of formula IIf. These compounds, which include all enantiomeric or diastereoisomeric forms or racemic mixtures thereof, may be isolated utilizing conventional methods such as crystallization, chromatography and the like.

In Reaction Scheme VIII, the compounds IX, XIX and XVII may have one or two chiral centers and accordingly one or two racemic forms of these compounds can exist. When these compounds are produced according to the methods outlined in Reaction Scheme VIII, and when $R_1$ is different from $R_2$, two racemic pairs are formed. It is advantageous to separate the two racemic forms of IX, XIX or XVII prior to their further transformations to the carboxylic acids of formula II. Thus, the acids of formula II may then be produced as pure racemates, which then may be resolved into their pure enaniomeric or diastereoisomeric forms by conventional means, for example, by conversion to salts of optically pure chiral amines such as cinchonidine, alpha-methyl-p-nitrobenzylamine, and subsequent fractional crystallization from a suitable solvent.

The enantiomerically pure acids may be recovered from their salts by conventional methods, for example extraction from an aqueous acidic solution.

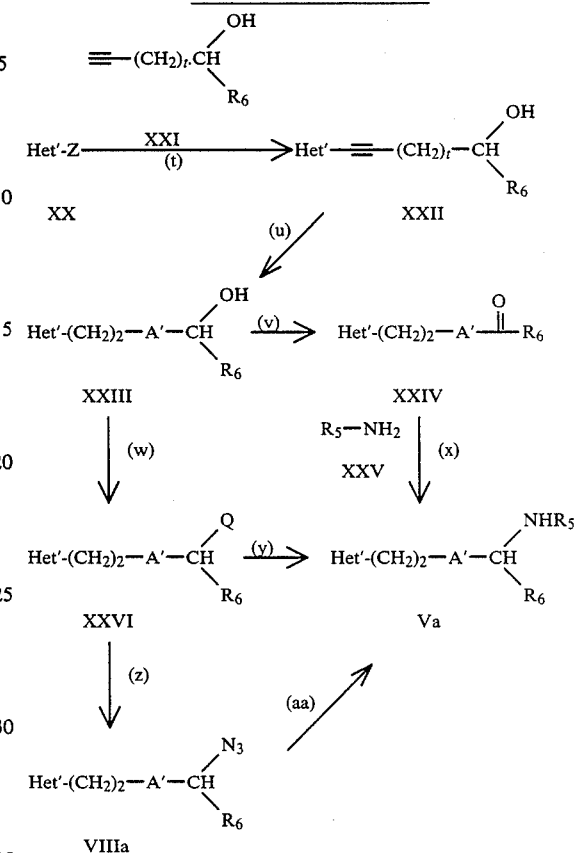

REACTION SCHEME IX

Het'-Z is a monocyclic 5- or 6-membered heteroaromatic or a bicyclic heteroaromatic compound containing one or two heteroatoms selected from nitrogen, oxygen, and sulfur, which compound may be substituted by halogen, lower alkyl or aryl wherein Z is iodide, bromide, or a perfluoroalkylsulfonate and is substituted in a position on the heteroaromatic ring such that it is active in transition metal catalyzed aryl-alkynyl coupling reactions. The compound of formula XXI becomes attached to Het' at the position of the leaving Z group. Examples of Het' are: 3-pyridinyl, 5-pyrimidinyl, 2-thienyl, 3-thienyl, 2-pyridinyl, 6-methyl-3-pyridinyl, 2-methyl-3-pyridinyl, 3-quinolinyl, 4-isoquinolinyl and the like. t is an integer of 0 to 4, A' is alkylene of 1 to 4 carbon atoms, Q is bromo, chloro, or an alkyl- or arylsulfonyloxy radical, and $R_5$ and $R_6$ are as previously described.

In Reaction Scheme IX, step (t), a compound of formula XX is reacted with an acetylene of formula XXI in the presence of an excess of a proton acceptor, for example, triethylamine, and a suitable palladium catalyst, for example, bis(triphenylphosphine)palladium dichloride, optionally in the presence of an inert solvent, for example, dichloromethane or dimethylformamide, at a temperature of from room temperature to 100° C., depending on the particular choice of Z-, solvent, and heteroaromatic ring, to give a compound of formula XXII. The resulting compound of formula XXII can be isolated utilizing conventional methods, for example, distillation, chromatography or the like, or may be used directly in the next step of the synthesis.

In step (u), an acetylene of formula XXII is dissolved in an inert solvent, for example, a lower alkanol, and hydrogenated over a suitable catalyst, for example, pallaidum on carbon, platinum oxide or the like, at a hydrogen pressure of from one to five atmospheres, preferably at room temperature, until reduction is complete. The resulting compound of formula XXIII can be isolated utilizing conventional methods, for example, distillation, chromatography or the like. Compounds of formula XXIII in which $R_6$ is other than hydrogen may be resolved into their enantiomers using standard methodology, for example, conversion to esters of chiral acids and chromatographic separation followed by ester hydrolysis.

In step (w), an alcohol of formula XXIII is reacted with an alkyl or aryl sulfonyl halide, for example, methanesulfonyl chloride or toluenesulfonyl chloride in the presence of a proton acceptor, for example, pyridine or triethylamine to give a compound of formula XXVI wherein Q is an alkyl- or arylsulfonyloxy radical of the same absolute chirality as the starting alcohol XXIII. Alternatively, a compound of formula XXIII can be reacted with a reagent useful for the conversion of alcohols into halides, for example, thionyl chloride, in the presence of a proton acceptor, for example, pyridine, until conversion to a compound of formula XXVI, Q=Cl, or Br is complete. The resulting compound of formula XXVI generally is not isolated, but utilized directly in the next step.

In step (z), a compound of formula XXVI, is reacted with an alkali metal azide, for example, sodium azide, in the presence of a polar inert solvent, for example, dimethylformamide, N-methylpyrrolidinone, dimethylsulfoxide or the like at a temperature of from about room temperature to 100° C. until azide formation is complete. The resulting compound of formula VIIIa can be isolated utilizing conventional methods, for example, chromatography or the like. This transformation generally proceeds with inversion of chirality at the carbon atom of XXVI bearing Q.

In step (y), a compound of formula XXVI is reacted with an amine anion equivalent to give an intermediate which can be deprotected to give an amine of formula Va. For example, a compound of formula XXVI can be reacted with an alkali metal phthalimide, for example, potassium phthalimide, in a polar aprotic solvent, for example dimethylformamide, dimethylsulfoxide, N-methylpyrrolidinone, or the like at a temperature of from about 60° C. to 120° C. until reaction is complete to give an intermediate of formula XXVI, Q=phthalimido, which can be converted to a compound of formula Va, by conventional means, for example by treatment with hydrazine in a lower alkanol solvent or with methylamine in a polar aprotic solvent such as dimethylformamide. Alternatively, a compound of formula XXVI can be reacted with a perfluoroalkylsulfonamide derived from a primary amine, for example N-alkyltrifluoromethanesulfonamide, in a polar aprotic solvent, for example, acetone, dimethylformamide, dimethylsulfoxide or the like in the presence of a base, for example, an alkali metal hydroxide or as appropriate, an alkali metal hydride, for example sodium hydride at a temperature of from room temperature to 100° C. The resulting compounds of formula Va can be isolated utilizing conventional methods, for example, distillation, crystallization of their acid addition salts, chromatography or the like. When a compound of formula XXVI is chiral, this transformation will generally proceed with inversion of configuration at the carbon atom bearing Q in a compound of formula XXVI.

In step (v), an alcohol of formula XXIII is oxidized to a carbonyl derivative of formula XXIV. Reagents which are useful for this transformation include chromium based oxidizing reagents, for example, pyridinium chlorochromate. A preferable procedure is described in K. Omura and D. Swern, Tetrahedron 1978, 34, 1651, which involves dissolution of a slight excess of an acid halide, for example, oxalyl chloride in an inert halocarbon solvent, for example dichloromethane, cooling to a reaction temperature of from −50° C. to −80° C., addition of excess dimethyl sulfoxide, stirring for 0.25 to 0.5 hours, addition of one equivalent of an alcohol of formula XXIII, after an additional 0.25 to 0.5 hours, addition of excess triethylamine while maintaining the reaction temperature at from −50° C. to −80° C., and allowing the reaction mixture to warm for 0.5 to 1 hour before quenching with water and excess inorganic base to produce a carbonyl derivative of formula XXIV.

In step (x), a carbonyl derivative of formula XXIV is reacted with an amine of formula XXV to form a Schiff's base which is reduced in the presence of an appropriate reducing agent to produce an amine of formula Va in either a one step or two step process. For example, a compound of formula XXIV is treated with a large excess of an amine of formula XXV and an equivalent amount of a weak organic acid, for example acetic acid, in the presence of a reducing agent such as sodium cyanoborohydride in a suitable solvent, preferably a lower alkanol, for example methanol, at room temperature until the starting material is consumed. Alternatively, an amine of formula XXV and a carbonyl derivative of formula XXIV heated together in aromatic solvent in an apparatus fitted with a water separator until water formation is complete. The resulting Schiff's base can be hydrogenated over a suitable catalyst, preferably Raney nickel, at a hydrogen pressure of from one to five atmospheres to give a compound of formula Va. When $R_6$ is not hydrogen and $R_5$ is chiral, the resulting amine Va may be enriched in one diastereomer over the other. For example, when $R_5$ is a chiral benzyl group, for example, R-alpha-methylbenzyl, and $R_6$ is lower alkyl, for example, methyl, the compound of formula Va may be diastereomerically enriched, and the chiral benzyl moiety may be removed, for example by hydrogenation over palladium on carbon to give an enantiomerically enriched amine of formula Va, $R_5$=hydrogen and $R_6$=lower alkyl. The compounds of formula Va can be isolated utilizing conventional methods, for example, extraction followed by distillation, crystallization of their acid addition salts, chromatography or the like.

In Reaction Scheme VII, step (aa), an azide of formula VIIIa is dissolved in a solvent, preferably a lower alkanol, and hydrogenated at a hydrogen pressure of from one to five atmospheres over a noble metal catalyst, for example, palladium on carbon or platinum oxide. The resulting compounds of formula Va can be isolated utilizing conventional methods, for example, distillation, crystallization of their acid addition salts, chromatography or the like. This transformation proceeds without alteration of the chirality of the carbon atom bearing the azido group in a compound of formula VIIIa.

Reaction Scheme X

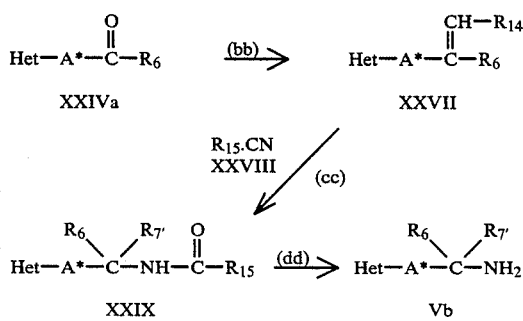

wherein Het, A* and $R_6$ are as previously described, $R_{7'}$ is alkyl, $R_{14}$ is hydrogen or lower alkyl, and $R_{15}$ is alkyl or aryl.

In Reaction Scheme X, step (bb), a carbonyl derivative of formula XXIVa is treated with an alkylidene triarylphosphorane in an inert solvent, preferably tetrahydrofuran, dimethylsulfoxide or diethyl ether, at a temperature of from $-80°$ C. to room temperature. The resulting compounds of formula XXVII can be isolated utilizing conventional methods, for example, distillation, chromatography or the like.

In step (cc), a nitrile of formula XXVIII is reacted with a compound of formula XXVII in the presence of a strong mineral acid, preferably sulfuric acid and a small amount of water. The resulting compounds of formula XXIX can be isolated utilizing conventional methods, for example, distillation, crystallization, chromatography or the like.

In step (dd), a compound of formula XXIX is hydrolyzed to an amine of formula Vb. This process is advantageously carried out where $R_{15}$ is 2-nitrobenzyl by catalytic reduction of the nitro group for example over palladium on carbon at one atmosphere hydrogen pressure, and heating of the residue in the absence of solvent or in the presence of a solvent, for example acetic acid. The resulting compounds of formula Vb can be isolated utilizing conventional methods, for example, distillation, crystallization of their acid addition salts, chromatography or the like.

Reaction Scheme XI

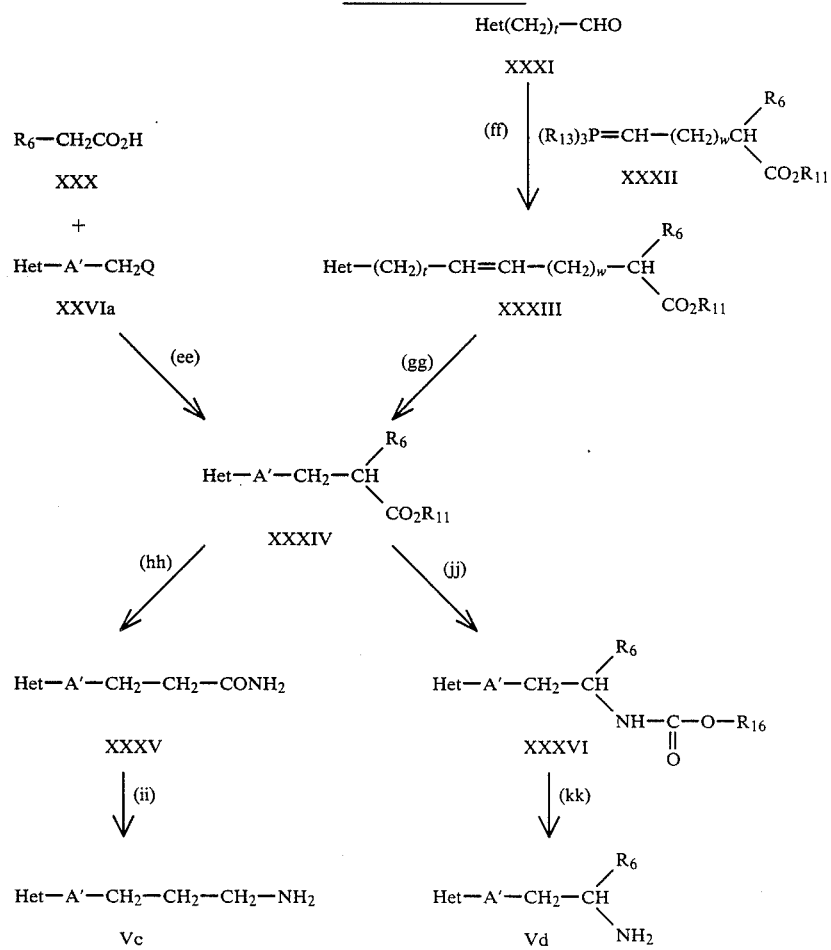

wherein Het, $R_6$, $R_{13}$, A', Q and t are as previously described, and $R_{11}$ is hydrogen or lower alkyl, $R_{16}$ is alkyl or aryl, and w is an integer of 0 to 3.

In Reaction Scheme XI, step (ee), the dilithium salt derived from a compound of formula XXX, for example by treatment with lithium diisopropyl amide, is reacted with a compound of formula XXVIa in a suitable inert solvent, for example tetrahydrofuran, to give a compound of formula XXXIV, $R_{11}$=hydrogen. The resulting compounds of formula XXXIV can be isolated utilizing conventional methods, for example, crystallization, chromatography or the like.

Compounds of formula XXXIV in which $R_6$ is non-hydrogen, and $R_{11}$ is hydrogen, may be resolved into their enantiomers by conversion to salts of chiral, enantiomerically pure amines, for example cinchonine, brucine, alpha-methylbenzylamine or the like. The pure diasteromeric salts are obtained by fractional crystallization from an appropriate solvent, for example a lower alkanol. The chiral, enantiomerically pure acids of formula XXXIV, $R_{11}$=hydrogen may be recovered from their salts by conventional means, for example extraction from an aqueous, acidic solution.

In step (ff), a heteroaromatic carboxaldehyde of formula XXXI, is reacted with a (carboxyalkylidene)-triarylphosphorane of formula XXXII in a suitable solvent, for example tetrahydrofuran, dichloromethane, methanol or dimethylsulfoxide, to give a compound of formula XXXIII. The resulting compounds of formula XXXIII can be isolated utilizing conventional methods, for example, crystallization, distillation, chromatography or the like.

In step (gg), a compound of formula XXXIII is hydrogenated over a suitable catalyst, for example, palladium on carbon or platinum oxide, in a suitable solvent, for example, a lower alkanol, at a hydrogen pressure of from one to five atmospheres until the theoretical amount of hydrogen is taken up to give a compound of formula XXXIV.

In step (hh), a compound of formula XXXIV is converted into an amide of formula XXXV using conventional techniques for the conversion of carboxylic acids and esters into the corresponding primary amide. For example, a compound of formula XXXIV, $R_{11}$=hydrogen may be converted to the corresponding acid chloride by treatment with thionyl chloride and then treated with an excess of ammonia to give a compound of formula XXXV. Alternatively, a compound of formula XXXIV, R=lower alkyl, may be converted into a compound of formula XXXV by treatment with excess ammonia, optionally in the presence of co-solvent, for example, a lower alkanol, at a temperature of from $-33°$ C. to room temperature. The reaction may be run in a pressure vessel when appropriate.

In step (ii), a compound of formula XXXV is treated with a reducing agent, for example borane in tetrahydrofuran at a temperature of from room temperature to the reflux temperature of the solvent for 4 to 24 hours or until reduction is complete to give a compound of formula Vc. The resulting compounds of formula Vc can be isolated utilizing conventional methods, for example, by destruction of the excess reagent with a lower alkanol, followed by treatment with a mineral acid, for example, hydrochloric acid, basification, evaporation of the solvent and extraction of the product into a suitable organic solvent, for example, dichloromethane and purified by distillation, chromatography or the like.

In step (jj), an acid of formula XXXIV, $R_{11}$=hydrogen, which may be obtained from the corresponding ester by hydrolysis, is subjected to conditions leading to a Curtius rearrangement in the presence of a lower alkanol. In a preferred procedure, an acid of formula XXXIV (R=hydrogen), is treated with one equivalent of diphenylphosphoryl azide in the presence of a proton acceptor, for example triethylamine or the like, and an excess of a lower alkanol or a phenol to give a compound of formula XXXVI. The resulting compounds of formula XXXVI can be isolated utilizing conventional methods, for example, crystallization, chromatography or the like.

In step (kk), a compound of formula XXXVI is treated with an excess of a mineral acid in water and optionally an addition co-solvent, for example a lower alkanol, at a temperature of from room temperature to 100° C. or with a strong base in water, optionally in the presence of a co-solvent, for example a lower alkanol at a temperature of between 60° C. and 100° C. to form a compound of formula Vd. The resulting compounds of formula Vd can be isolated utilizing conventional methods, for example, crystallization of their acid addition salts, distillation, chromatography or the like.

Reaction Scheme XII

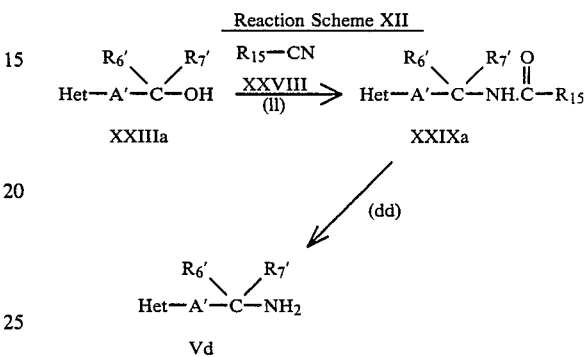

wherein Het, A′, $R_{7'}$ and $R_{15}$, are as previously described, and $R_{6'}$ is lower alkyl.

In Reaction Scheme X, step (ll), an alcohol of formula XXIIIa is reacted with a nitrile of formula XXVIII in the presence of a mineral acid, for example sulfuric acid, and water at a temperature of from $-20°$ C. to room temperature to give a compound of formula XXIXa. The compound of formula XXIXa can be isolated by conventional means, for example chromatography, crystallization or the like.

In this Reaction Scheme, step (dd), is the same as step (dd) in Reaction Scheme X to give a compound of formula Vd. The compound of formula Vd can be isolated by conventional means, for example, chromatography, crystallization or its acid addition salts, distillation or the like.

Reaction Scheme XIII

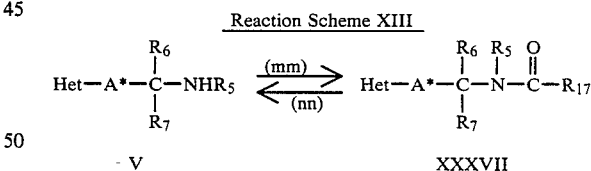

wherein Het, A*, $R_5$, $R_6$ and $R_7$ are as previously described, $R_{17}$ is a chiral moiety, for example, a bonded chain lower alkyl or lower alkyl substituted with one or two groups selected from hydroxy, lower alkoxy, lower alkylcarbonyloxy, perfluoroalkyl, or aryl.

In Reaction Scheme XIII, step (mm), those compounds of formula V which are chiral may be resolved into their enantiomers by conversion to amides of chiral, enantiomerically pure acids using common techniques of peptide coupling. For example, a chiral amine of formula V may be coupled with a chiral, enantiomerically pure acid, for example (R)-mandelic acid, in the presence of a suitable coupling reagent, for example, a dicyclohexylcarbodiimide optionally in the presence of a promoter, for example 1-hydroxybenzotriazole in a polar, aprotic solvent, for example dimethylformamide to give an amide of formula XXXVII. Amides of formula XXXVII may be separated into pure diastereomers by fractional crystallization, chromatography or the like.

In step (nn), enantiomerically pure compounds of formula V may be recovered by hydrolysis of diastereomerically pure amides of formula XXXVII, for example with an aqueous mineral acid at a temperature of from 60° C. to 120° C.

The compounds of formula I can form acid addition salts with inorganic or organic acids. Thus, they form pharmaceutically acceptable acid addition salts with both pharmaceutically acceptable organic and inorganic acids, for example, with hydrohalic acids, such as, hydrochloric acid, hydrobromic acid, hydroiodic acid, other mineral acid salts, such as, sulfuric acid, nitric acid, phosphoric acid, perchloric acid or the like, alkyl and mono-aryl sulfonic acids such as, ethanesulfonic acid, toluenesulfonic acid, benzenesulfonic acid, or the like, other organic acids such as tartaric acid, maleic acid, citric acid, salicylic acid, ascorbic acid and the like. Non-pharmaceutically acceptable acid addition salts of compounds of formula I can be converted into pharmaceutically acceptable acid addition salts via conventional metathetic reactions whereby the non-pharmaceutically acceptable anion is replaced by a pharmaceutically acceptable anion; or alternatively, by neutralizing the non-pharmaceutically acceptable acid addition salt and then reacting the so-obtained free base with a reagent yielding a pharmaceutically acceptable acid addition salt.

The compounds of formula I exhibit activity as platelet activating factor (PAF) antagonists and are, therefore, useful in disease states characterized by excess platelet activating factor or for the prevention and treatment of cardiovascular diseases, pulmonary diseases, immunological disorders, inflammatory diseases, dermatological disorders, shock or transplant rejection.

The useful activity of the compounds of formula I can be demonstrated by the following procedures:

BINDING ASSAY

(a) Assay

The binding assay was done in 400 µl polyethylene microcentrifuge tubes (Beckman) containing 50 µl of an oil mixture of 2 parts Siliconol AR200 (Serva): 1 part Silicone Fluid (Arthur H. Thomas). Buffer, standards, or analogs (150 µl total volume) were added to the tubes. Radiolabelled $^3$H-PAF (50 µl) was then added to the tubes. The reaction was started by the addition of 50 µl of dog platelets ($2 \times 10^7$ platelets). The tubes were capped, inverted several times to mix, and incubated for 10 minutes at room temperature. The platelets were separated from the incubation mixture by centrifuging 1 minute in a Beckman Microfuge B centrifuge. The tip of the microfuge tube was cut off, and the platelets were washed out of the tip with 200 µl of 50% methanol (Burdick and Jackson). Aquasol (NEN, 10 ml) was added and the radioactivity in the samples was determined using an LS 8100 Beckman liquid scintillation counter linked to a Techtran tape recorder. Data was processed through an in-house computer system. Alternatively, radioactivity was determined using a Searle Mark III liquid scintillation counter linked to a Iso-Data microprocessor. Results are set forth in Table I.

(b) Preparation of Platelets

Blood was collected from anesthesized or unanesthesized dogs into 50 ml plastic centrifuge tubes containing 3.8% sodium citrate as the anticoagulant (1 volume of citrate/9 volumes of blood). The red cells were removed by centrifugation for 15 minutes at 600 rpm (100–125 g) at room temperature. An aliquot of the supernatant platelet rich plasma (PRP) was saved for cell counting and the remainder was acidified by pH 6.5 with 0.15M citric acid. The platelet pellet was obtained after a 10 minute centrifugation at 2000 rpm (1000 g) at room temperature. Washed platelets were prepared by resuspending the platelet pellet once with PBS containing 1 mM EDTA, centrifuging as noted, and then resuspending the platelets in 0.1% BSA-PBS. An aliquot of the washed platelets was counted. Platelets used for binding assays were diluted to $2 \times 10^7$ platelets/assay tube ($4 \times 10^8$ platelets/ml). Platelet counting was done using a Royco Cell-Crit 921.

PAF Induced Bronchoconstriction Assay

Male animals (Hartlet Strain, 400–500 g) were anesthetized with urethane (2 g/kg, i.p.). Each animals' trachea was cannulated and the guinea pigs were respirated using a Harvard small animal rodent respirator (3.0 cc stroke volume, 40 breaths per min.). Tracheal pressure was recorded from a cannula inserted in the trachea and connected to a Statham Pressure Transducer.

The jugular vein was cannulated for administering compounds. Spontaneous breathing was arrested with succinylcholine (1.2 mg/kg, i.v.) administered 2 minutes prior to intravenous injection of platelet activating factor (PAF). Since propranolol has been shown to enhance bronchoconstrictor responses, all animals were pretreated five minutes prior to challenge with propranolol (0.1 mg/kg, i.v.).

For, the intravenous testing, the guinea pig is given a 5-minute pretreatment with propranolol at a dose of 0.1 mg/kg intravenously. The test compound is administered with a 1 minute pretreatment prior to intravenous challenge with PAF. The animal is then challenged with a 1.0 µg/kg intravenous dose of PAF and the change is tracheal pressure is measured.

For the oral testing, the procedure includes a 2-hour pretreatment period with the test compound administered through an oral gavage tube. Propranolol or succinylcholine and PAF are administered intravenously, and the change in tracheal pressure measured.

The change is tracheal pressure is determined by subtracting the steady state baseline achieved after administration of succinylcholine from the peak bronchoconstriction seen after challenge with PAF. The mean is calculated for each test compound and compared to the mean of the control animals to give the percent inhibition of bronchoconstriction. The standard error is calculated as the standard error of the mean.

PAF INDUCED PLATELET COUNT DECREASE

Male Hartley guinea pigs weighing between 500 and 900 grams were fed standard guinea pig chow and tap water ad libitum. PAF was solubilized in ethanol and stored as a 2 mM stock solution at −70° C. The stock solution of PAF was diluted to 1 pM in Tris buffer pH 7.4 and 0.1% BSA for all experiments.

(a) Intravenous Procedure

Guinea pigs were anesthetized with urethane (1.6 g/kg, i.p.). A catheter (PE50) was introduced into the right carotid artery for withdrawing blood. A second catheter PE10) was introduced into the jugular vein for injecting drugs and for administering the PAF challenge (75 ng/kg, i.v.). A control blood sample was obtained and platelets were counted in a whole blood platelet analyzer. PAF was then given and blood samples were taken 15, 30, and 60 seconds after the challenge for platelet counts. Fifteen minutes later, selected concentrations of the test compound were solubilized in DMSO and injected intravenously into a group of 4–6 animals. Only one concentration of antagonist was used in each animal group. Fifteen minutes after drug injection, blood samples were taken before and 15, 30, and 60 sec after the PAF challenge, and analyzed for platelet number.

(b) Oral Procedure

Animals were anesthetized with sodium pentobarbital (35 mg/kg, i.p.) and the caritoid artery and jugular vein were cannulated as described above. The cannulae were exteriorized at the base of the neck and the animals were allowed to recover. At least 18 hours after surgery, conscious unrestrained guinea pigs were used in the experiment. The animals were challenged two time with PAF (120 ng/kg, i.v.); the first to establish a consistent response to PAF and the second to serve as a control for the PAF challenge. Blood samples were taken before and 15, 30, and 45 seconds after PAF challenge and platelets were counted. Thirty minutes after the control PAF challenge, the animal were orally dosed with either gum acacia or the test compound. Animals were then challenged with PAF at 1, 3, 5, and 24 hours after the administration of the drug.

DATA ANALYSIS AND STATISTICS

The % change, i.e., the difference in platelet number before and after PAF challenge was calculated by:

$$\% \text{ change} = \frac{\text{\# control platelets (0 Time)} - \text{lowest \# of platelets after } PAF}{\text{\# of control platelets (0 Time)}}$$

the % activity of drug was then determined by $$\% \text{ activity} = \frac{\% \text{ change (control)} - \% \text{ change (drug)}}{\% \text{ change (control)}}$$

Statistical significance (p 0.05) of the difference between the mean PAF control and mean drug treated activity was determined with paried Student's t-test.

The compounds of formula I also have Thromboxane Synthase (TXA$_2$Syn.) Inhibitory Activity, which can be demonstrated as follows.

TXA$_2$ SYNTHESIS INHIBITION

Thromboxane Synthase inhibitory TAX$_2$ syn. activity is measured by following the conversion of $^{14}$C-thromboxane A$_2$ (TXA$_2$) using microsomal fractions from human platelets as enzyme source. In the aqueous incubation medium, the TA X$_2$ decomposes rapidly into TXB$_2$. The amount of TXA$_2$ syn. is adjusted so that under the conditions of the assay approximately 80–90% of the substrate, PGH$_2$, is converted to product in control tubes. To prepare $^{14}$C-PGH$_2$, $^{14}$C-AA(50-60 mCi/mmole; Rose Chem.) is incubated with sheep seminal vesicular gland microsomes for 1.5 min. at 37° C. and then the $^{14}$C-PGH$_2$ is extracted with diethylether, purified on columns of Sephadex LH-20 or silicic acid, and stored in acetone at −70° C. Incubations are done as follows. Sufficient $^{14}$C-PGH$_2$ to yield a final substrate concentration of 10 μM (∼30,000 cpm) is added to the incubation tubes and then the acetone is removed under nitrogen. The tubes are placed in an ice bath and then 215 μl of ice cold phosphate buffered saline, 10 μl of ethanol (control) or of test drug in ethanol, and 25 μl of the microsomal suspension are added with mixing in that order as rapidly as possible. The tubes are incubated at 22° C. for 2 minutes, the reaction is stopped and then the radioactive products and the unconverted PGH$_2$ are extracted and analyzed by thin layer chromatography. The amount of $^{14}$C-PGH$_2$ converted to products is analyzed by thin layer chromatography. The amount of $^{14}$C-PGH$_2$ converted to products was used as a measure of TXA$_2$ synthase activity. Inhibitors were tested initially at a concentration of 100 μM. IC$_{50}$ values were calculated by linear regression analysis of successive 10 fold dilutions of the test compound concentration. Results are provide in Table II.

Test results obtained with compounds of formula I in the described tests are set forth in Table I which follows:

TABLE I

| Compound | Inhibition of PAF Binding IC50 (nM) |
| --- | --- |
| [R,S-(E)]-3-(2,2-Diphenylcyclopropyl)-N-[4-(3-pyridinyl)butyl]-2-propenamide | 150 |
| [R-(E)]-3-(2,2-Diphenylcyclopropyl)-N-[4-(3-pyridinyl)butyl]-2-propenamide | 250 |
| [S-(E)]-3-(2,2-Diphenylcyclopropyl)-N-[4-(3-pyridinyl)butyl]-2-propenamide | 35 |
| [R,S-(E)]-3-[2,2-bis(3-Fluorophenyl)cyclopropyl]-N-[4-(3-pyridinyl)butyl]-2-propenamide | 53 |
| [R-(E)]-3-[2,2-bis(3-Fluorophenyl)cyclopropyl]-N-[4-(3-pyridinyl)butyl]-2-propenamide | 200 |
| [S-(E)]-3-[2,2-bis(3-Fluorophenyl)cyclopropyl]-N-[4-(3-pyridinyl)butyl]-2-propenamide | 24 |
| [S,R*-(E)]-3-[2,2-bis(3-Fluorophenyl)cyclopropyl]-N-[1-methyl-4-(3-pyridinyl)butyl]-2-propenamide | 130 |
| [R,S-(E)]-3-[2,2-bis(4-Fluorophenyl)cyclopropyl]-N-[4-(3-pyridinyl)butyl]-2-propenamide | 100 |
| [R-(E)]-3-[2,2-bis(4-Fluorophenyl)cyclopropyl]-N-[4-(3-pyridinyl)butyl]-2-propenamide | 200 |
| [S-(E)]-3-[2,2-bis(4-Fluorophenyl)cyclopropyl]-N-[4-(3-pyridinyl)butyl]-2-propenamide | 25 |
| [R,S-(E)]-3-[2,2-bis(4-Fluorophenyl)-1-methylcyclopropyl]-N-[4-(3-pyridinyl)butyl]-2-propenamide | 300 |
| [R-(E)]-3-[2,2-bis(4-Fluorophenyl)-1-methylcyclopropyl]-N-[4-(3-pyridinyl)butyl]-2-propenamide | 500 |
| [S-(E)]-3-[2,2-bis(4-Fluorophenyl)-1-methylcyclopropyl]-N-[4-(3-pyridinyl)butyl]-2-propenamide | 200 |
| [S,R*-(E)]-3-[2,2-bis(4-Fluorophenyl)cyclopropyl]-N-[1-methyl-4-(3-pyridinyl)butyl]-2-propenamide | 450 |
| [R,S-(E)]-3-[2,2-bis(3-Methoxyphenyl)cyclopropyl]-N-[4-(3-pyridinyl)butyl]-2-propenamide | 70 |
| [R-(E)]-3-[2,2-bis(3-Methoxyphenyl)cyclopropyl]-N-[4-(3-pyridinyl)butyl]-2-propenamide | 300 |
| [S-(E)]-3-[2,2-bis(3-Methoxyphenyl)cyclopropyl]-N-[4-(3-pyridinyl)butyl]-2-propenamide | 36 |
| [S,R*-(E)]-3-[ 2,2-bis(3-Methoxyphenyl)cyclopropyl]-N-[1-methyl-4-(3-pyridinyl)butyl]-2-propenamde | 450 |
| [1(R,S),2(R,S)-(E)]-3-[2-(3-Methoxyphenyl)-2-phenylcyclopropyl]-N-[4-(3-pyridinyl)butyl]-2-propenamide | 8 |
| [1(R,S),2(S,R)-(E)]-3-[2-(3-Methoxyphenyl)-2-phenylcyclopropyl]-N-[4-(3-pyridinyl)butyl]- | 35 |

TABLE I-continued

| Compound | Inhibition of PAF Binding IC50 (nM) |
|---|---|
| 2-propenamide | |
| [R,S-(E)]-3-[2,2-bis[3-(Trifluoromethyl)phenyl]-cyclopropyl]-N-[4-(3-pyridinyl)butyl]-2-propenamide | 350 |
| [R,S-(Z)]-3-(2,2-Diphenylcyclopropyl)-N-[4-(3-pyridinyl)butyl]-2-propenamide | 650 |
| [R-(Z)]-3-(2,2-Diphenylcyclopropyl)-N-[4-(3-pyridinyl)butyl]-2-propenamide | 100 |
| [S-(Z)]-3-(2,2-Diphenylcyclopropyl)-N-][4-(3-pyridinyl)butyl]-2-propenamide | 1000 |
| [R,S-(Z)]-3-[2,2-bis(3-Fluorophenyl)cyclopropyl]-N-[4-(3-pyridinyl)butyl]-2-propenamide | 100 |
| [R,S-(Z)]-3-[2,2-bis(4-Fluorophenyl)cyclopropyl]-N-[4-(3-pyridinyl)butyl]-2-propenamide | 1000 |
| [1(R,S),2(R,S)-(Z)]-3-[2-(3-Methoxyphenyl)-2-phenylcyclopropyl]-N-[4-(3-pyridinyl)butyl]-2-propenamide | 300 |
| [1(R,S),2(S,R)-(Z)]-3-[2-(3-Methoxyphenyl)-2-phenylcyclopropyl]-N-[4-(3-pyridinyl)butyl]-2-propenamide | 250 |
| (R,S)-2,2-Diphenyl-N-[4-(3-pyridinyl)butyl]-cyclopropanamide | 300 |
| (R)-2,2-Diphenyl-N-[4-(3-pyridinyl)butyl]-cyclopropanamide | 600 |
| (S)-2,2-Diphenyl-N-[4-(3-pyridinyl)butyl]-cyclopropanamide | 200 |
| [R,S-(E)]-3-(2,2-Diphenylcyclopropyl)-N-[4-(3-pyridinyl)butyl]-2-propenethioamide | 55 |

TABLE II

| Compound | Percent Inhib. of PAF-induced Bronchoconstriction | | Percent Inhib. of PAF-induced Platelet Count Decrease | |
|---|---|---|---|---|
| | 1 mg/Kg i.v. | 50 mg/Kg p.o. | 3 mg/Kg i.v. | 30 mg/Kg p.o. |
| [S-(E)]-3-[2,2-bis(4-Fluorophenyl)cyclopropyl]-N-[4-(3-pyridinyl)butyl]-2-propenamide | 33 ± 7 | 62 ± 13 | | |
| [R,S-(E)]-3-[2,2-bis(3-Methoxyphenyl)cyclopropyl]-N-[4-(3-pyridinyl)butyl]-2-propenamide | — | 14 ± 1 | | |
| [R-(E)]-3-[2,2-bis(3-Methoxyphenyl)cyclopropyl]-N-[4-(3-pyridinyl)butyl]-2-propenamide | 8 ± 5 | 8 ± 2 | | |
| [S-(E)]-3-[2,2-bis(3-Methoxyphenyl)cyclopropyl]-N-[4-(3-pyridinyl)butyl]-2-propenamide | 25 ± 8 | — | | |
| [R,S-(Z)]-3-[2,2-bis(3-Fluorophenyl)cyclopropyl]-N-[4-(3-pyridinyl)butyl-2-propenamide | — | 52 ± 28 | 22 | |
| [R,S-(Z)]-3-[2,2-bis(4-Fluorophenyl)cyclopropyl]-N-[4-(3-pyridinyl)butyl]-2-propenamide | — | 78 ± 11 | | |
| [1(R,S),2(R,S)-(Z)]-3-[2-(3-Methoxyphenyl)-2-phenylcyclopropyl]-N-[4-(3-pyridinyl)butyl]-2-propenamide | — | 9 ± 14 | | |
| [1(R,S),2(S,R)-(Z)]-3-[2-(3-Methoxyphenyl)-2-phenylcyclopropyl]-N-[4-(3-pyridinyl)butyl]-2-propenamide | — | 15 ± 12 | | |
| [R,S-(E)-3-(2,2-Diphenylcyclopropyl)-N-[4-(3-pyridinyl)butyl]-2-propenamide | 48 ± 16 | — | | |
| [R-(E)]-3-(2,2-Diphenylcyclopropyl)-N-[4-(3-pyridinyl)butyl]-2-propenamide | 71 ± 12 | 57 ± 19 | | |
| [S-(E)]-3-(2,2-Diphenylcyclopropyl)-N-[4-93-pyridinyl)butyl]-2-propenamide | 86 ± 7 | — | 44 | |
| [R,S-(E)]-3-[2,2-bis(3-Fluorophenyl)cyclopropyl]-N-[4-(3-pyridinyl)butyl]-2-propenamide | 96 ± 2 | — | 30 | |
| [R-(E)]-3-[2,2-bis(3-Fluorophenyl)cyclopropyl]-N-[4-(3-pyridinyl)butyl]-2-propenamide | 29 ± 3 | 10 ± 3 | 13 | |
| [S-(E)]-3-[2,2-bis(3-Fluorophenyl)cyclopropyl]-N-[4-(3-pyridinyl)butyl]-2-propenamide | 90 ± 4 | 95 ± 3 | 79 | 66 |
| [S,R*-(E)]-3-[2,2-bis(3-Fluorophenyl)cyclopropyl]-N-[1-methyl-4-(3-pyridinyl)butyl]-2-propenamide | | | | |
| [R,S-(E)]-3-[2,2-bis(4-Fluorophenyl)cyclopropyl]-N-[4-(3-pyridinyl)butyl]-2-propenamide | 20 ± 8 | 82 ± 5 | | |
| [R-(E)[-3-[2,2-bis(4-Fluorophenyl)cyclopropyl]-N-[4-(3-pyridinyl)butyl]-2-propenamide | 13 ± 11 | 83 ± 7 | 31 | |

A compound of formula I, an enantiomer thereof or a salt thereof or a composition containing a therapeutically effective amount of a compound of formula I, an enantiomer thereof or a salt thereof can be administered by methods well known in the art. Thus, a compound of formula I an enantiomer thereof or a salt thereof can be administered either singly or with other pharmaceutical agents, for example, antihistamines, mediator release inhibitors, methyl xanthines, beta agonists or antiasthmatic steroids such as prednisone and prednisolone, orally, parenterally, rectally, or by inhalation, for example, in the form of an aerosol, micropulverized powder or nebulized solution. For oral administration they can be administered in the form of tablets, capsules, for example, in admixture with talc, starch, milk sugar or other inert ingredients, that is, pharmaceutically acceptable carriers, or in the form of aqueous solutions, suspensions, elixirs or aqueous alcoholic solutions, for example, in admixture with sugar or other sweetening agents, flavoring agents, colorants, thickeners and other conventional pharmaceutical excipients. For parenteral administration, they can be administered in solutions or suspension, for example, as an aqueous or peanut oil solution or suspension using excipients and carriers conventional for this mode of administration. For administration as aerosols, they can be dissolved in a suitable pharmaceutically acceptable solvent, for example, ethyl alcohol or combinations of miscible solvents, and mixed with a pharmaceutically acceptable propellant. Such aerosol compositions are packaged for use in a pressurized container fitted with an aerosol valve suitable for release of the pressurized composition. Preferably, the aerosol valve is a metered valve, that is one which on activation releases a predetermined effective dose of the aerosol composition.

In the practice of the invention, the dose of a compound of formula I or a salt thereof to be administered and the frequency of administration will be dependent on the potency and duration of activity of the particular compound of formula I or salt to be administered and on the route of administration, as well as the severity of the condition, age of the mammal to be treated and the like. Oral doses of a compound of formula I or a salt thereof contemplated for use in practicing the invention are in the range of from about 25 to about 1000 mg per day, preferably about 25 to about 250 mg either as a single dose or in divided doses.

The geometric and diastereomeric isomers encompassed by formula I can be separated by conventional means, for example, chromatography, crystallization and the like. It is noted, however, that the separation in most instances is done at a earlier stage in the synthesis of the compounds of formula I.

The examples which follow also further describe the invention. All temperatures given are in degree centigrade unless otherwse stated.

EXAMPLE 1

(R, S)-alpha-Methyl-4-(3-pyridinyl)-3-butyn-1-ol

In an inert atmosphere, 26 g of bis(triphenylphosphine) palladium dichloride and 2.28 g of cuprous iodide were added to a stirred solution of 311.2 g of (R,S)-4-pentyn-2-ol, 556.8 g of 3-bromopyridine and 665 mL of triethylamine in 1.8 L of dichloromethane at ambient temperature. After stirring for 75 minutes, the mildly exothermic reaction reached reflux temperature, and when the gentle boiling had subsided (40 minutes), external heat was applied to maintain reflux for 5 additional hours. The cooled reaction was stirred overnight at room temperature, then 1 L of water and 500 g of ice were added, followed by 420 mL of conc. hydrochloric acid (HCl) and the stirring was continued for several minutes. After the phases were separated, the aqueous layer was extracted with dichloromethane (4×1 L) and then the organic layers were backwashed with 1 L of 1N HCl before being discarded. The original aqueous phase was treated with 500 mL of 10N sodium hydroxide (NaOH) and the second aqueous layer was basified with 200 mL of 10N NaOH before each was extracted in turn with dichloromethane (1×2 L; 3×1 L). The combined organic extracts were dried over potassium carbonate ($K_2CO_3$) and evaporated to constant weight under reduced pressure to yield 477.3 g of crude (R,S)-alpha-methyl-4-(3-pyridinyl)-3-butyn-1-ol as an amber oil.

EXAMPLE 2

Preparation of (R,S)-alpha-methyl-4-pyridinebutanol

The crude (R,S)-alpha-methyl-4-(3-pyridinyl)-3-butyn-1-ol (477.3 g) obtained in the previous Example was hydrogenated over 20 g of platinum oxide in 3.5 L of ethanol at room temperature and atmospheric pressure. After the uptake of hydrogen had stopped, the catalyst was filtered and the solvent was removed under reduced pressure. The residual oil was distilled on a Kugelrohr apparatus (115°–120° C./0.1 mm) to yield 420.5 g of (R,S)-alpha-methyl-3-pyridinebutanol.

EXAMPLE 3

Preparation of 5-(3-pyridinyl)-2-pentanone

A stirred solution of 218.6 g of oxalyl chloride in 1.5 L of dry dichloromethane was cooled to −75° C. under argon, then a mixture of 141 g of dry dimethylsulfoxide in 200 mL of dichloromethane was added dropwise over 75 minutes such that the reaction temperature did not exceed −72° C. The mixture was stirred at −75° C. for 10 minutes, then a solution of 271.5 g of (R,S)-alpha-methyl-3-pyridinebutanol in 125 mL of dichloromethane was added dropwise over 55 minutes, while the reaction temperature was maintained below −70° C. After the addition of substrate was completed, the mixture was stirred at −75° C. for another 30 minutes, then 520 mL of triethylamine was added over 65 minutes while the reaction temperature was maintained between −65° and −70° C. The cooling bath was removed, and after the reaction was allowed to equilibrate to room temperature over 1 hour, 1 L of water was added and the phases separated. The aqueous layer was extracted with dichloromethane (2×800 mL), and then the organic phase and extracts were washed in turn with 800 mL of 1.5N NaOH and with 800 mL of 10% sodium chloride (NaCl). The combined organic layers were dried ($K_2CO_3$) and evaporated to yield 266 g of crude ketone. The product was distilled to yield 248.6 g of 5-(3-pyridinyl)-2-pentanone (bp 100°–102° C./0.2 mm).

EXAMPLE 4

Preparation of (R,S)-methanesulfonic acid 5-(3-pyridinyl)-2-pentyl ester

In an inert atmosphere, a solution of 2.42 mL of methanesulfonyl chloride in 10 mL of dichloromethane was added over 10 minutes to a stirred mixture of 5.0 g of (R,S)-alpha-methyl-3-pyridinebutanol and 6.2 mL of triethylamine in 50 mL of dry dichloromethane maintained at −40° C. After 30 minutes the reaction was warmed to 0° C., then a small piece of ice was added and the mixture was stirred in a an ice bath for another 15 minutes. The solution was then washed in turn with water (3×15 mL), 1N NaOH (2×15 mL) and brine (10 mL). The dried ($K_2CO_3$) organic layer was evaporated to furnish 7.2 g of (R,S)-methanesulfonic acid 5-(3-pyridinyl)-2-pentyl ester.

EXAMPLE 5

Preparation of (R,S)-3-(4-azidopentyl)pyridine

A mixture of 2.5 g of (R,S)-methanesulfonic acid 5-(3-pyridinyl)-2-pentyl ester, 0.832 g of sodium azide, 1.5 mL of water and 15 mL of dimethylformamide was stirred at 50° C. under argon for 150 minutes. The cooled solution was dilued with 40 mL of water and extracted with dichloromethane (3×30 mL). The extracts were washed in turn with water (2×20 mL) and then were combined, dried (K$_2$CO$_2$) and evaporated to furnish 1.76 g of (R,S)-3-(4-azidopentyl)pyridine as an oil.

EXAMPLE 6

Preparation of (R,S)-3-(ethoxycarbonyl)butyltriphenylphosphonium bromide.

A solution of 86.3 g of (R,S)-4-bromo-2-methylbutanoic acid ethyl ester and 104.9 g of triphenylphosphine in 600 mL of toluene was stirred at reflux for 4 days. As the reaction proceeded, the phosphonium bromide separated from solution as an oil. After the reaction was cooled, the toluene supernatant was decanted and replaced with 500 mL of fresh toluene. The mixture was stirred at reflux for 30 minutes, then was cooled and the toluene layer was again decanted. After this process was repeated a second time, the residual oil was dried in vacuo to give 187 g of (R,S)-3-(ethoxycarbonyl)butyltriphenylphosphonium bromide as a viscous oil.

EXAMPLE 7

Preparation of [(R,S)-Z]-2-methyl-5-(3-pyridinyl)-4-pentenoic acid ethyl ester A stirred solution of 10.56 g of sodium hydride (60% dispersion in oil) in 1000 mL of dry dimethylsulfoxide was heated at 70° C. until the evolution of hydrogen stopped (30 minutes), then the solution was cooled to 0° C. and a solution of 103.7 g of (R,S)-3-(ethoxycarbonyl)butyltriphenylphosphonium bromide in 200 mL of dimethylsulfoxide was added. After the mixture had stirred at room temperature for 30 minutes, a solution of 20.8 mL of 3-pyridinecarboxaldehyde in 100 mL of tetrahydrofuran was added and the reaction was stirred at room temperature overnight. The mixture was diluted with ice-water and extracted with dichloromethane (6×150 mL). The combined organic layers were then extracted with 4×400 mL of 0.5N HCl. The acidic layers were made basic with 125 mL triethylamine and extracted with dichloromethane (5×150 mL), and the dried (K$_2$CO$_3$) extracts were evaporated to furnish 34 g of crude reaction product. An initial purification of the material by high pressure liquid chromatography (HPLC) (ether-hexane; 3:2) yielded 11.9 g of a mixture of (Z)- and (E)-isomers (4:1). A subsequent separation of the mixture by HPLC with recycle gave 6.77 g of [(R,S)-Z]-2-methyl-5-(3-pyridinyl)-4-pentenoic acid ethyl ester and 3 g of a mixture of [(R,S)-Z]-2-methyl-5-(3-pyridinyl)-4-pentenoic acid ethyl ester and its (E)-isomer.

EXAMPLE 8

Preparation of (R,S)-alpha-methyl-3-pyridinepentanoic acid ethyl ester

A solution of 5.5 g of a mixture (1:1) of [(R,S)-E]- and [(R,S)-Z]-2-methyl-5-(3-pyridinyl)-4-pentenoic acid ethyl ester in 100 mL was ethanol was hydrogenated over 4.0 g of 10% palladium on carbon (Pd/C). After the uptake of hydrogen had stopped, the catalyst was removed by filtration and the solvent evaporated to give 5.33 g of (R,S)-alpha-methyl-3-pyridinepentanoic acid ethyl ester.

EXAMPLE 9

Preparation of (R,S)-alpha-methyl-3-pyridinepentanoic acid

A mixture of 5.3 g of (R,S)-alpha-methyl-3-pyridinepentanoic acid, 35 mL of 1N NaOH and 35 mL of methanol was stirred at reflux for 3 hours, then most of the methanol was removed under reduced pressure. The solution was diluted to 100 mL with water and extracted with dichloromethane (3×35 mL). The aqueous layer was then neutralized with 35 ml of 1N HCl and extracted with dichloromethane (3×30 mL), then dried over sodium sulfate (Na$_2$SO$_4$). Extracts were evaporated to yield 3.47 g of (R,S)-alpha-methyl-3-pyridinepentanoic acid.

EXAMPLE 10

Preparation of (R,S)-[1-methyl-4-(3-pyridinyl)butyl]carbamic acid 1,1-dimethylethyl ester As in Example 36, 1.93 g of (R,S)-alpha-methyl-3-pyridinepentanoic acid when treated with 2.21 mL of diphenylphosphorylazide in 10 mL of t-butanol containing 1.4 mL of triethylamine furnished 2.45 g of crude product. Purification of the material by HPLC (ethyl acetate) yielded 2.2 g of (R,S)-[1-methyl-4-(3-pyridinyl)butyl]carbamic acid 1,1-dimethylethyl ester as a colorless oil.

EXAMPLE 11

Preparation of (R,S)-N-[1-methyl-4-(3-pyridinyl)butyl]acetamide

To a mixture of 10.6 g of (R,S)-alpha-methyl-3-pyridinebutanol in 30 mL of acetonitrile was added 20 mL of sulfuric acid. After the reaction was stirred at 50° C. for 2 hours, it was poured over a mixture of 500 g of ice and 400 mL of 4N NaOH and extracted with dichloromethane (2×150 mL). Evaporation of the dried (K$_2$CO$_3$) extracts gave 6 g of crude product which was purified by HPLC (methanol-ethyl acetate; 1:49) and triturated with ether to yield 2.9 g of (R,S)-N-[1-methyl-4-(3-pyridinyl)butyl]acetamide, mp 70°–71.5° C.

EXAMPLE 12

Preparation of (R,S)-alpha-methyl-3-pyridinebutanamine From 5-(3-pyridinyl)-2-pentanone A mixture of 248.5 g of 5-(3-pyridinyl)-2-pentanone, 95.85 g of sodium cyanoborohydride and 1170 g of ammonium acetate in 5.3 L of dry methanol was stirred at room temperature for 8 days, then 3 L of methanol was removed by distillation under reduced pressure (internal temp ~30° C.). The reaction was cooled in an ice bath as 3.8 L of 6N HCL was added dropwise over 2 hours. After the mixture was stirred at room temperature overnight, it was made strongly basic by the addition of 2 L of 12.5N NaOH and extracted with dichloromethane (1×2 L; 2×1 L). The combined extracts were dried (K$_2$CO$_3$) and evaporated to yield 244 g of a light brown oil, which was distilled to give 205 g of (R,S)-alpha-methyl-3-pyridinebutanamine (bp 95°–100° C./0.15 mm)

EXAMPLE 13

Preparation of (R,S)-alpha-methyl-3-pyridinebutanamine

(a) From 3-(4-azidopentyl)pyridine

A solution of 0.9 g of (R,S)-3-(4-azidopentyl)pyridine in 25 mL ethanol was hydrogenated over 0.05 g 10% Pd/C at 50 psi. After 105 minutes, the catalyst was removed by filtration and the solvent was removed under reduced pressure to yield 0.69 g of a colorless oil. Evaporative distillation of the crude product furnished 0.57 g of (R,S)-alpha-methyl-3-pyridinebutanamine.

(b) From (R,S)-[1-methyl-4-(3-pyridinyl)butyl]carbamic acid 1,1-dimethylethyl ester As in Example 37, hydrolysis of 2.1 g of (R,S)-[1-methyl-4-(3-pyridinyl)butyl]carbamic acid 1,1-dimethylethyl ester in 25 mL of 1N HCl yielded, after the usual work up and evaporative distillation of the product (95°–100° C./0.2 mm), 1.25 g of (R,S)-alpha-methyl-3-pyridinebutanamine.

(c) From (R,S)-N-[1-methyl-4-(3-pyridinyl)butyl]acetamide

A solution of 2.06 g of (R,S)-N-[1-methyl-4-(3-pyridinyl) butyl]acetamide in 50 mL of 6N HCl was stirred at reflux for 22 hours. In an argon atmosphere, the cooled mixture was made basic with the careful addition of 30 mL of 10N NaOH and was extracted with dichloromethane (2×75 mL). The extracts were washed with brine, then were combined, dried ($K_2CO_3$) and evaporated to give 1.43 g of (R,S)-alpha-methyl-3-pyridinebutanamine.

EXAMPLE 14

Preparation of [R-(R*,R*)]-alpha-hydroxy-N-[1-methyl-4-(3-pyridinyl)butyl]benzeneacetamide

(a) From (R,S)-alpha-methyl-3-pyridinebutanamine

A solution of 281.5 g of 1,3-dicyclohexylcarbodiimide in 400 ml of dimethylformamide was added to a stirred solution of 204 g of (R,S)-alpha-methyl-3-pyridinebutanamine, 198.4 g of (R)-mandelic acid and 209.75 g of 1-hydroxybenzotriazole in 1400 mL of dimethylformamide, maintained at −10° C. during the addition by intermittent cooling with a dry ice-acetone bath. After stirring at −5° for 4 hours, then at room temperature overnight the mixture was recooled to 0° C. for 2 hours. The precipitated solids were filtered and washed in turn with cold dimethylformamide (2×150 mL) and ethyl acetate (2×300 mL). This material, a mixture of 1,3-dicyclohexylurea (DCU) and the less soluble (R*,R)-mandelamide, was dispersed in 2 L of 1N HCl and stirred at room temperature for 3 hours. The undissolved solids (DCU) were removed by filtration and were washed with 200 mL of dilute HCl and with water. The filtrate was basified and the resulting material was collected by filtration, washed with water and dried in vacuo to give 64.4 g of [R-(R* R*)]alpha-hydroxy-N-[1-methyl-4-(3-pyridinyl)butyl]benzeneacetamide, the (R*,R)-mandelamide, mp 144°–146° C.; $[\alpha]_D^{25}$ −27.8° (c, 1.0, MeOH).

The original mother liquors and washings were concentrated to dryness under reduced pressure and the residue was dispersed in 2 of 1.5N NaOH and extracted with dichloromethane (1×2 L; 2×1 L). The organic extracts were washed with in turn with 1N NaOH (2×800 mL) and then in turn with 1N HCl (1×1.5 L; 2×750 mL). The combined acidic aqueous layers were basified with 350 mL of 10N NaoH and extracted with dichloromethane (1×2 L; 2×1 L). The extracts were dried ($K_2CO_3$) and evaporated to give 280 g of mandelamide, rich (∼3:2) in the (S*,R)-diastereomer. The residue was crystallized three times from 2-propanol to yield 74.1 g of the less soluble (R*,R)-mandelamide, mp 144°–146° C.

The mother liquors from the final two crystallizations were combined, evaporated and the residue crystallized twice from 2-propanol to give an additional 7.2 g of the (R*,R)-diastereomer, mp 143°–145° C. The total yield of [R-(R*,R*)]-alpha-hydroxy-N-[1-methyl-4-(3-pyridinyl)butyl]benzeneacetamide, obtained in three crops, was 145.6 g (78.5%).

All remaining mother liquors were combined, evaporated and dried to give 198 g of mandelamide rich in the (S*,R)-diastereoisomer. This material was reserved for further processing, particularly to serve as a potential source of (S)-alpha-methyl-4-pyridinebutanamine.

(b) Via an enatioselective process from 5-(3-pyridinyl)-2-pentanone

A solution of 70.5 g of 5-(3-pyridinyl)-2-pentanone and 53.5 g of (R)-(+)-alpha-methylbenzylamine in 700 mL of toluene containing 1.8 g of p-toluenesulfonic acid was heated at reflux for 17 hours. Water was removed from the reaction as it was formed using a Dean-Stark trap. The cooled solution was hydrogenated over 70 g of Raney Nickel at room temperature and 50 psi. When approximately 50% of the theoretical amount of hydrogen had been taken up, the reaction essentially stopped. The spent catalyst was removed and replaced with 70 g of fresh Raney Nickel and the hydrogenation was continued until the absorption of hydrogen ceased. After the catalyst was removed by filtration, the filtrate was washed with 250 mL of 1N sodium hydroxide solution, then was dried and evaporated to give 106 g of an oil. HPLC analysis of the product showed that the main component (∼68%) was [R-(R*,R)]-N-[1-methyl-(3-pyridinyl)butyl]-alpha-methylbenzylamine along with 13% of the related (S*,R)-diastereomer.

The above mixture (105 g) in 1 L of ethanol was hydrogenolysed over 21 g of 20% Pd(OH)₂ on charcoal (50° C.; 25 psi) for a total of 51 hours. After the catalyst was removed by filtration, the solvent was evaporated and the residue distilled to provide 33.6 g of alpha-methyl-3-pyridinebutanamine enriched in the (R)-enantiomer.

To a cooled (−5° C.) solution of 32 g of the above enriched amine, 33 g of 1-hydroxybenzotriazole and 31.22 g of (R)-mandelic acid in 350 mL of dimethylformamide, was added a solution of 44.26 g of 1,3-dicyclohexylcarbodiimide in 150 mL of dimethylformamide and the mixture was stirred at −5° C. for 18 hours. After the precipitated dicyclohexylurea was removed by filtration, the filtrate was evaporated and the residue dispersed in 300 mL of cold 2N sodium hydroxide. The resulting solids were removed by filtration, washed with dilute sodium hydroxide solution and with water and then dissolved in 500 mL of 2N hydrochloric acid. The acidic solution was extracted with dichloromethane (3×150 mL) to remove neutral impurities, then was basified with 10N sodium hydroxide and extracted with dichloromethane (6×300 mL). The dried extracts were evaporated to give 55 g of residual solid. Crystallization of the product from ethanol gave 25.6 g of [R-(R*,R)]-alpha-hydroxy-N-[1-methyl-4-(3-pyridinyl)butyl]benzeneacetamide, mp 141°–143° C. An additional 1.3 g of product, mp 141°–143° C., was obtained from the mother liquors.

EXAMPLE 15

Preparation of [S-(S*,S*)]-alpha-hydroxy-N-[1-methyl-4-(3-pyridinyl)butyl]benzeneacetamide (a) From (R,S)-alpha-methyl-3-pyridinebutanamine To an ice cold solution of 2.0 g of (S)-(+)-mandelic acid and 1.82 mL of triethylamine in 20 mL of dry dimethylformamide was added 2.82 mL of diphenylphosphoryl azide. The mixture was stirred at 0° C. for 30 minutes before 2.15 g of (R,S)-alphamethyl-3-pyridinebutanamine was added. After the reaction was stirred at room temperature overnight, it was diluted with 130 mL of ethyl acetate, washed with water (4×50 mL), dried ($K_2CO_3$) and evaporated. The residue was crystallized from ethyl acetate (3x) to give 0.45 g of [S-(S*,S)]-alpha-hydroxy-N-[1-methyl-4-(3-pyridinyl)butyl]benzeneacetamide, mp 142°–145° C.

The absolute configuration of [S-(S*,S*)]-alpha-hydroxy-N-[1-methyl-4-(3-pyridinyl)butyl]benzeneacetamide, was established by X-ray crystallographic analysis.

(b) From enriched (S)-alpha-methyl-pyridinebutanamine

A solution of 160 g of crude [S-(R*,R*)]-alpha-hydroxy-N-[1-methyl-4-(3-pyridinyl)butyl]benzeneacetamide in 800 mL of 6N HCl was treated with 85 mL conc. HCl and then was heated at reflux overnight as described in Example 16. The crude amine (~85 g), isolated in the normal manner, was distilled to furnish 76.4 g of (S)-alpha-methyl-3-pyridinebutanamine, (60%ee; bp 89°–91°/0.15 mm).

Under the conditions outlined in Example 14a, 76.2 g of the amine was reacted with 74.2 g of (S)-mandelic acid in the presence of 105.2 g of 1.3-dicyclohexylcarbodiimide and 78.4 g of 1-hydroxybenzotriazole in 1 L of dimethylformamide. A similar workup furnished 109 g of [S-(S*,S*)]-alpha-hydroxy-N-[1-methyl-4-(3-pyridinyl)butyl]benzeneacetamide, mp 143°–145° C., $[\alpha]_D^{25}$+27.8° (c, 1.0, MeOH).

EXAMPLE 16

Preparation of (R)-alpha-methyl-3-pyridinebutanamine

A solution of 145 g of [R-(R*,R*)]-alpha-hydroxy-N-[1-methyl-4-(3-pyridinyl)butyl]benzeneacetamide in 900 mL of 6N HCl was treated with 80 mL of conc. HCl and then was heated at reflux for 2 days. After most of the solvent was removed under reduced pressure, the residue was made decidedly basic with 10N NaOH in an argon atmosphere, and extracted with dichloromethane (1×1.2 L; 2×600 mL). The dried ($K_2CO_3$) extracts were evaporated and the crude product was distilled to give 78.5 g of (R)-alpha-methyl-3-pyridinebutanamine, (bp 95° C./0.2 mm).

EXAMPLE 17

Preparation of (S)-alpha-methyl-3-pyridinebutanamine

As in Example 16, a solution of 16.3 g of [S-(S*,S*)]-alpha-hydroxy-N-[1-methyl-4-(3-pyridinyl)butyl]benzeneacetamide in 160 mL of 6N HCl was heated at reflux for 22 hours. The crude product, obtained by the usual work up was distilled to yield 8.3 g of (S)-alpha-methyl-3-pyridinebutanamine, (bp 85°–87° C./0.1 mm)

EXAMPLE 18

Preparation of (R,S)-alpha-ethyl-4-(3-pyridinyl)-3-butyn-1-ol

Under the conditions described in Example 1, 395 g of 3-bromopyridine and 259.3 g of (R,S)-5-hexyne-3-ol were reacted together in 1.5 L of dichloromethane in the presence of 418 mL of triethylamine, 17.56 g of bis(triphenylphosphine)palladium dichloride and 1.7 g of cuprous iodide. The usual work-up furnished 361.5 g of crude (R,S)-alpha-ethyl-4-(3-pyridinyl)-3-butyn-1-ol as a brown oil.

EXAMPLE 19

Preparation of (R,S)-alpha-ethyl-3-pyridinebutanol

As in Example 2, hydrogenation of 361.5 g of crude (R,S)-alpha-ethyl-4-(3-pyridinyl)-3-butyn-1-ol over 15 g of platinum oxide in 3 L of ethanol at room temperature and atmospheric pressure and distillation of the product furnished 357 g of (R,S)-alpha-ethyl-3-pyridinebutanol (bp 120°–130°/0.1 mm) as a colorless oil.

EXAMPLE 20

Preparation of 6-(3-pyridinyl)-3-hexanone

As in Example 3, 356.6 g of (R,S)-alpha-ethyl-3-pyridinebutanol was added to a mixture prepared in the prescribed manner from 211.7 g of oxalyl chloride and 170 g of dimethylsulfoxide in 1.75 L of dichloromethane. After the addition of 630 mL of triethylamine, the reaction was worked up in the usual way to yield 347.6 g of crude product which was distilled to give 327.9 g of 5-(3-pyridinyl)-3-hexanone (bp 110°–115° C./0.1 mm).

EXAMPLE 21

Preparation of (R,S)-alpha-ethyl-3-pyridinebutanamine

In the manner described in Example 12, 372.9 g of 6-(3-pyridinyl)-3-hexanone was reacted with 116.5 g of sodium cyanoborohydride and 1426 g of ammonium acetate in 6.5 L of dry methanol for 3 days at room temperature, and then 4.5 L of 6N HCl was added and the mixture stirred overnight. Distillation of the crude product gave 289.4 g of (R,S)-alpha-ethyl-3-pyridinebutanamine (bp 95°–100° C./0.1 mm).

EXAMPLE 22

Preparation of [R-(R*,R*)]-alpha-hydroxy-N-[1-ethyl-4-(3-pyridinyl)butyl]benzeneacetamide and [S-(R*,R*)]-alpha-hydroxy-N-[1-ethyl-4-(3-pyridinyl)butyl]benzeneacetamide As in Example 14a, a solution of 367.4 g of 1,3-dicyclohexylcarbodiimide in 500 mL of dimethylformamide was added to a stirred solution of 289 g of (R,S)-alpha-ethyl-3-pyridinebutanamine, 259 g of (R)-mandelic acid and 274 g of 1-hydroxybenzotriazole in 1.7 L of dimethylformamide maintained at −10° C. during the addition. After stirring at −5° C. for 3 hours, then at room temperature overnight, the mixture was recooled to 0° C. for 2 hours. The precipitated solids were filtered and washed in turn with cold dimethylformamide (3×150 mL) and ethyl acetate (3×200 mL). The solids, a mixture of 1,3-dicyclohexylurea (DCU) and the less soluble (R*,R)-mandelamide, was dispersed in 1N HCl (2 L) and stirred at room temperature for 4 hours. The undissolved solids (DCU) were removed by filtration and were washed with 200 mL dilute HCl and with water. The filtrate was basified and the resulting crystalline material was collected by filtration, washed with water and dried in vacuo to give 195.4 g of [R-(R*,R*)]-alpha-hydroxy-N-[1-ethyl-4-(3-pyridinyl)butyl]benzeneacetamide, mp 161.5°–163°; $[\alpha]_D^{25}$ −14.9° (c, 1.0 MeOH).

The original mother liquors and washings were concentrated to dryness and were worked up as in Example 14a. The crude residue was triturated with hot hexane (1 L), and the solids filtered to give 265 g of mandelamide rich (>7:1) in the more soluble (S*,R)-diastereomer. Fractional crystallization of the residue from 2-propanol furnished 147 g of [S-(R*,R*)]-alpha-hydroxy-N-[1-ethyl-4-(3-pyridinyl)butyl]benzeneacetamide, mp 122°–124° C.; $[\alpha]_D^{25}$ −41.2°(c, 1.0 MeOH).

EXAMPLE 23

Preparation of (R)-alpha-ethyl-3-pyridinebutanamine

As in Example 16, a solution of 195 g of [R-(R*,R*)]-alpha-hydroxy-N-[1-ethyl-4-(3-pyridinyl)butyl]benzeneacetamide in 1.1 L of 6N HCl was treated with 104 mL of conc. HCl and then was heated at reflux for 2 days. The crude amine, obtained by the normal work up, was distilled to give 109 g of (R)-alpha-ethyl-3-pyridinebutanamine, (bp 105° C./0.2 mm); $[\alpha]_D^{25}$ −11.9° (c, 1.0, MeOH)

EXAMPLE 24

Preparation of (S)-alpha-ethyl-pyridinebutanamine

As in Example 16, a solution of 31.2 g of [S-(R*,R*)]-alpha-hydroxy-N-[1-ethyl-4-(3-pyridinyl)butyl]benzeneacetamide in 175 ml of 6N HCl was treated with 10 mL of conc. HCl and then was heated at reflux for 42 hours. The normal work up furnished 16.4 g of (S)-alpha-ethyl-3-pyridinebutanamine, (bp 95°–98° C./0.1 mm); $[\alpha]_D^{25}$ +11.75° (c, 1.0, MeOH).

EXAMPLE 25

Preparation of trifluoromethanesulfonic acid 6-methyl-3-pyridinyl ester

A suspension of 7.48 g of 5-hydroxy-2-methylpyridine and 24.4 g of bis(trifluoromethanesulphonyl)-phenylimide in 25 mL of dichloromethane was cooled in an ice bath as 10 mL of dry triethylamine was added. After 1 hour at 0° C., the mixture was allowed to stir at room temperature for 18 hours, then was washed in turn with 1N NaOH (2×50 mL) and with half saturated K$_2$CO$_3$ solution. Concentration of the dried (K$_2$CO$_3$) solution gave a yellow oil which was evaporatively distilled to yield 14.48 g of trifluoromethanesulfonic acid 6-methyl-3-pyridinyl ester, (bp 65°–70° C./0.1 mm.)

EXAMPLE 26

Preparation of (R,S)-5-(6-methyl-3-pyridinyl)-4-pentyn-2-ol

A solution of 28 g trifluoromethanesulfonic acid 6-methyl-3-pyridinyl ester and 14.4 g of (R,S)-4-pentyn-2-ol and 110 mL triethylamine in 350 mL of dry dimethylformamide was deoxygenated with argon and 2.4 g of bis(triphenylphosphine) palladium dichloride was added. After the mixture was stirred at 90° C. for 3 hours, it was cooled, then acidified with 300 mL of 6N HCl and extracted with ether. The aqueous phase was made basic with sodium hydroxide solution and extracted with ethyl acetate. The organic extract was washed with brine, then dried (K$_2$CO$_3$) and evaporated to furnish an oil which was evaporatively distilled to yield 10.8 g of (R,S)-5-(6-methyl-3-pyridinyl)-4-pentyn-2-ol, bp 123°–130° C./0.02 mm.

EXAMPLE 27

Preparation of (R,S)-alpha-6-dimethyl-3-pyridinebutanol

As in Example 2, 10.3 g of (R,S)-5-(6-methyl-3-pyridinyl)-4-pentyn-2-ol was hydrogenated over 1.1 g of 10% Pd/C in 135 mL of ethanol at room temperature and atmospheric pressure. After the usual workup, the resulting yellow oil was purified by HPLC (ethyl acetate) to give 10.45 g of (R,S)-alpha-6-dimethyl-3-pyridinebutanol. A portion was evaporatively distilled at 105°–110° C./0.1 mm to furnish the analytical sample.

EXAMPLE 28

Preparation of 5-(6-methyl-3-pyridinyl)-2-pentanone

Under conditions similar to that describe in Example 3, 10.25 g of (R,S)-alpha-6-dimethyl-3-pyridinebutanol in 50 mL of dichloromethane was added to an mixture prepared from 8.58 g of oxalyl chloride and 9.27 g of dimethylsulfoxide in 225 mL of dichloromethane. After the addition of 36.8 mL of triethylamine, the reaction was worked up in the usual manner and the crude product was purified by HPLC (ethyl acetate-hexane; 1:1). The resulting material was distilled to give 7.4 g of 5-(6-methyl-3-pyridinyl)-2-pentanone (bp 88°–92 C./0.05 mm).

EXAMPLE 29

Preparation of (R,S)-6-alpha-dimethyl-3-pyridinebutanamine

As in Example 12, 7.27 g of 5-(6-methyl-3-pyridinyl)-2-pentanone was reacted with 2.71 g of sodium cyanoborohydride and 31.1 g of ammonium acetate in 115 mL of dry methanol for 3 days at room temperature. After the chilled reaction was quenched by the addition of 110 mL of 6N HCl, the mixture heated at reflux for 90 minutes then was cooled and worked up in the usual manner. Distillation of the crude product gave 4.31 g of (R,S)-6-alpha-dimethyl-3-pyridinebutanamine (bp 98°–101° C./0.1 mm).

EXAMPLE 30

Preparation of 5-bromo-2-[(2-trimethylsilyl)ethynyl]pyridine

A degassed solution of 15.0 g of 2,5-dibromopyridine, 9.0 mL of trimethylsilylacetylene and 0.27 g of cuprous iodide in 200 mL of triethylamine was treated with 1.0 g of bis(triphenylphosphine)palladium dichloride. After an ice bath was used to control the initial exotherm, the reaction was stirred at room temperature overnight, then was diluted with 400 mL ether. The mixture was washed in turn with water (4×75 mL) and with brine (75 mL), then was dried (K$_2$CO$_3$) and evaporated. The residual dark oil was passed through a plug of silica gel (ether) and then was purified by HPLC (ether-hexane; 1:49). Crystallization of the resulting material from hexane gave 11.86 g of 5-bromo-2-[(2-trimethylsilyl)ethynyl]pyridine, mp 56°–59° C.

EXAMPLE 31

Preparation of (R,S)-5-[6-[2-trimethylsilyl)ethynyl]-3-pyridinyl]-4-pentyne-2-ol A solution of 9.78 g of 5-bromo-2-[(2-trimethylsilyl)ethynyl]pyridine and 0.19 g of cuprous iodide in 150 mL of triethylamine and 50 mL dichloromethane were deoxygenated with argon and 3.4 g of (R,S)-4-pentyn-2-ol and 0.7 g of bis(triphenylphosphine)palladium dichloride were added. After the dark mixture was stirred overnight at room temperature, the solvents were removed under reduced pressure and the residue was dissolved in ether. The solution was washed with water and brine, then was dried ($K_2CO_3$) and evaporated. The crude product was filtered through a plug of silica gel (ethyl acetate-hexane; 1:10) and then was purified by HPLC (ethyl acetate) to give (R,S)-5-[6-[2-trimethylsilyl)ethynyl]-3-pyridinyl]-4-pentyne-2-ol, mp 79°–80° C.

EXAMPLE 32

Preparation of (R,S)-6-ethyl-3-pyridine-alpha-methylbutanol

A solution of 8.51 g of (R,S)-5-[6-[2-(trimethylsilyl)ethynyl]-3-pyridinyl]-4-pentyn-2-ol in 60 mL of methanol and 15 mL of 2.5N NaOH was stirred for 1 hour and diluted to 300 mL with ethyl acetate. The separated organic layer was washed in turn with water and brine, then was dried ($K_2CO_3$) and evaporated. The residue was hydrogenated over 0.7 g of 10% Pd/C in 150 mL of ethanol at atmospheric pressure and room temperature. After the normal work up, the crude hydrogenation product was evaporatively distilled to afford 5.61 g of (R,S)-6-ethyl-3-pyridine-alpha-methylbutanol (bp 110°–115° C./0.1 mm).

EXAMPLE 33

Preparation of 5-(6-ethyl-3-pyridinyl)-2-pentanone 5-(6-Ethyl-3-pyridinyl)-2-pentanone was prepared by the method described in Example 3. Starting with 4.4 g of (R,S)-6-ethyl-3-pyridine-alpha-methylbutanol, there was obtained 4.9 g of 5-(6-ethyl-3-pyridinyl)-2-pentanone (bp 107°–110° C./0.1 mm).

EXAMPLE 34

Preparation of (R,S)-6-ethyl-alpha-methyl-3-pyridinebutanamine (R,S)-6-ethyl-alpha-methyl-3-pyridinebutanamine was made by the method outlined in Example 12. Starting from 4.75 g of 5-(6-ethyl-3-pyridinyl)-2-pentanone there was obtained 2.44 g of (R,S)-6-ethyl-alpha-methyl-3-pyridinebutanamine, bp 101°–104° C./0.15 mm.

EXAMPLE 35

Preparation of (R,S)-alpha-cyclopropyl-3-pyridinepentanoic acid

In an inert atmosphere, 33 mL of 1.6M butyl lithium in hexene was added to a stirred solution of 7.4 mL diisopropylamine in 20 mL dry tetrahydrofuran previously cooled to −78° C. for 30 minutes, then a solution of 2.5 g cyclopropaneacetic acid in 10 mL dry tetrahydrofuran was added over 3 minutes. The reaction was allowed to equilibrate to ambient temperature and then was heated at 50° C. for 1 hour to complete the formation of the dianion. The mixture was recooled to −78° C. and a solution of 7.67 g 3-bromopropyl)pyridine (freshly liberated from its HBr salt) in 20 mL tetrahydrofuran was added. The reaction was allowed to warm to room temperature and then was heated at 50° C. for 7 hours. The solvents were removed in vacuo and the residue was dissolved in 100 mL 1N HCl and extracted with dichloromethane (3×50 ml). The organic layers were backwashed in turn with 2×25 mL portions of 1N HCl, then the aqueous layers were basified with 17 mL 10N NaOH solution and extracted with dichloromethane (3×100 mL) to remove the starting bromide. The aqueous phase was then acidified by the addition of 3 mL acetic acid and extracted with dichloromethane (1×150 mL; 2×100 mL). The extracts were washed with brine, then were combined, dried ($Na_2SO_4$) and evaporated to give 4.6 g of (R,S)-alpha-cyclopropyl-3-pyridinepentanoic acid as a colorless solid. A portion was crystallized from ether-hexane to yield the analytical sample, mp 82°–84° C.

EXAMPLE 36

Preparation of (R,S)-[1-cyclopropyl-4-(3-pyridinyl)butyl]carbamic acid 1,1-dimethylethyl ester A solution of 4.2 g of (R,S)-alpha-cyclopropyl-3-pyridinepentanoic acid 5.8 g of diphenylphosphorylazide and 3 mL if triethylamine in 40 mL of t-butanol was stirred at reflux under argon overnight. After the solvents were removed under reduce pressure, the residue was dissolved in 100 mL of dichloromethane and washed with 2×50 mL portions of 1N NaOH. The aqueous layers were washed in turn with 50 mL of dichloromethane. Then the combined organic extracts were dried ($K_2CO_3$) and evaporated to yield 5.6 g of an oil. The crude carbamate was purified by HPLC (ethyl acetate) to furnish 4.8 g of (R,S)-[1-cyclopropyl-4-(3-pyridinyl)butyl]carbamic acid 1,1-dimethylether ester as a colorless oil.

EXAMPLE 37

Preparation of (R,S)-alpha-cyclopropyl-3-pyridinebutanamine

A solution of 4.4 g of (R,S)-[1-cyclopropyl-4-(3-pyridinyl)butyl]-carbamic acid 1,1-dimethylethyl ester in 50 mL of 1N HCl was heated on a steam bath for 75 minutes then was cooled and extracted with 50 mL of ether. In an atmosphere of argon, the aqueous layer was treated with 6 mL of 10N NaOH and extracted with 2×50 mL portions of dichloromethane. Evaporation of the dried ($K_2CO_3$) extracts gave 2.8 g of (R,S)-alpha-cyclopropyl-3-pyridinebutanamine as a colorless oil.

EXAMPLE 38

Preparation of (R,S)-alpha-propyl-3-pyridinepentanoic acid

As in Example 35, 2.04 g of pentanoic acid was treated with two equivalents of lithium diisopropylamide (LDA) and then reacted with 4.0 g of 3-(3-bromopropyl)pyridine. After workup, the crude product (3.5 g) was crystallized from ether-hexane to afford 2.7 g of (R,S)-alpha-propyl-3-pyridinepentanoic acid, mp 55°–57° C.

EXAMPLE 39

Preparation of
(R,S)-[1-propyl-4-(3-pyridinyl)butyl]carbamic acid
1,1-dimethylethyl ester As in Example 36, 2.5 g of (R,S)-alpha-propyl-3-pyridinepentanoic acid when reacted with 2.45 mL of diphenylphosphorylazide in 25 mL of t-butanol containing 1.6 mL of triethylamine furnished 3.1 g of crude carbamate. Purification of the material by HPLC (ethyl acetate) yielded 2.75 g (R,S)-[1-propyl-4-(3-pyridinyl)butyl]carbamic acid 1,1-dimethylethyl ester as an oil.

EXAMPLE 40

Preparation of
(R,S)-alpha-propyl-3-pyridinebutanamine

As in Example 37, hydrolysis of 1.8 g of (R,S)-[1-propyl-4-(3-pyridinyl)butyl]carbamic acid 1,1-dimethylethyl ester in 25 mL of 1N HCl, after the usual workup, gave 1.15 g of (R,S)-alpha-propyl-3-pyridinebutanamine. A portion was distilled on a Kugelrohr apparatus (110° C./0.1 mm) to yield the analytical sample.

EXAMPLE 41

Preparation of
(R,S)-alpha-(1-methylethyl)-3-pyridinepentanoic acid

As in Example 35, 2.04 g of isovaleric acid was treated with two equivalents of LDA and then reacted with 4.0 g of 3-(3-bromopropyl)pyridine. The crude product was crystallized from ether-hexane to yield 2.8 g of (R,S)-alpha-(1-methylethyl)-3-pyridinepentanoic acid, mp 52°–55° C. Recrystallization of a sample from the same solvents gave the analytical specimen, mp 54°–56° C.

EXAMPLE 42

Preparation of
(R,S)-[1-(1-methylethyl)-4-(3-pyridinyl)butyl]carbamic
acid 1,1-dimethylethyl ester As in Example 36, 2.3 g of (R,S)-alpha-(1-methylethyl)-3-pyridine-pentanoic acid, when reacted with 2.3 mL of diphenylphosphorylazide in 25 mL of t-butanol containing 1.5 mL of triethylamine gave 2.8 g of product. Purification of the crude ester by HPLC (ethyl acetate) gave 2.5 g of (R,S)-[1-(1-methylethyl)-4-(3-pyridinyl)butyl]carbamic acid 1,1-dimethylethyl ester as an oil.

EXAMPLE 43

Preparation of
(R,S)-alpha-(1-methylethyl)-3-pyridinebutanamine

As in Example 37, hydrolysis of 1.7 g of (R,S)-[1-(1-methylethyl)-4-(3-pyridinyl)butyl]carbamic acid 1,1-dimethylethyl ester in 25 mL of 1N HCl yielded 1.1 g of (R,S)-alpha-(1-methylethyl)-3-pyridinebutanamine. A small sample was distilled on a Kugelrohr (110°–115° C./0.1 mm) to furnish the analytical specimen.

EXAMPLE 44

Preparation of (R,S)-alpha-butyl-3-pyridinepentanoic acid

As in Example 35, 2.32 g of hexanoic acid was treated with two equivalents of LDA and then reacted with 4.0 g of 3-(3-bromopropyl)pyridine. The usual workup yielded 4 g of (R,S)-alpha-butyl-3-pyridinepentanoic acid, as an oil.

EXAMPLE 45

Preparation of
(R,S)-1-[1-butyl-4-(3-pyridinyl)butyl]carbamic acid
1,1-dimethylethyl ester As in Example 36, 3.7 g of (R,S)-alpha-butyl-3-pyridinepentanoic acid, when reacted with 3.4 mL of diphenylphosphorylazide in 25 mL of t-butanol containing 2.2 mL of triethylamine yielded 4.4 g of crude carbamate. Purification of the product by HPLC (ethyl acetate) gave 3.6 g of (R,S)-[1-butyl-4-(3-pyridinyl)butyl]carbamic acid 1,1-dimethylethyl ester as an oil.

EXAMPLE 46

Preparation of (R,S)-alpha-butyl-3-pyridinebutanamine

As in Example 37, hydrolysis of 2.2 g of (R,S)-[1-butyl-4-(3-pyridinyl)butyl]carbamic acid 1,1-dimethylethyl ester in 25 mL 1N HCl, after the usual workup yielded 1.35 g of (R,S)-alpha-butyl-3-pyridinebutanamine. A portion was distilled on a Kugelrohr (115° C./0.1 mm) to yield the analytical sample.

EXAMPLE 47

Preparation of
(R,S)-alpha-cyclopentyl-3-pyridinepentanoic acid

As in Example 35, 2.56 g of cyclopentaneacetic acid was treated with two equivalents of LDA and then reacted with 4.0 g of 3-(3-bromopropyl)pyridine. The crude product (4 g) was crystallized from ether-hexane to yield 3.1 g of (R,S)-alpha-cyclopentyl-3-pyridinepentanoic acid, mp 95°–97° C.

EXAMPLE 48

Preparation of
(R,S)-[1-cyclopentyl-4-(3-pyridinyl)butyl]carbamic
acid 1,1-dimethylethyl ester As in Example 36, 2.8 g of (R,S)-alpha-cyclopentyl-3-pyrinepentanoic acid, when treated with 2.5 mL of diphenylphosphorylazide in 25 mL of t-butanol containing 1.58 mL of triethylamine yielded 3.4 g of product. Purification of the crude by HPLC (ethyl acetate) yielded 2.5 g of (R,S)-[1-cyclopentyl-4-(3-pyridinyl)butyl]carbamic acid 1,1-dimethylethyl ester as an oil.

EXAMPLE 49

Preparation of
(R,S)-alpha-(1-cyclopentyl)-3-pyridinebutanamine

As in Example 37, hydrolysis of 1.6 g of (R,S)-[1-cyclopentyl)-4-(3-pyridinyl)butyl]carbamic acid 1,1-dimethylethyl ester in 25 mL of 1N HCl yielded 1.05 g of (R,S)-alpha-(1-cyclopentyl)-3-pyridinebutanamine. A sample was distilled (125°130° C./0.1 mm) to yield the analytical specimen.

EXAMPLE 50

Preparation of
(R,S)-alpha-cyclohexyl-3-pyridinepentanoic acid

As in Example 35, 2.84 g of cyclohexaneacetic acid was treated with two equivalents of LDA and then reacted with 4.0 g of 3-(3-bromopropyl)pyridine. The crude product (3.8 g) was crystallized from ether-hexane to give 2.7 g of (R,S)-alpha-cyclohexyl-3-pyridinepentanoic acid, mp 92°–93° C.

EXAMPLE 51

Preparation of (R,S)-[1-cyclohexyl-4-(3-pyridinyl)butyl]carbamic acid 1,1-dimethylethyl ester As in Example 36, 2.5 g of (R,S)-alpha-cyclohexyl-3-pyridinepentanoic acid, when reacted with 2.68 g of diphenylphosphorylazide in 25 mL of t-butanol containing 0.97 g of triethylamine yielded 3.1 g of crude product. Purification by HPLC (ethyl acetate) furnished 2.8 g of (R,S)-[1-cyclohexyl-4-(3-pyridinyl)butyl]carbamic acid 1,1-dimethylethyl ester. The material was crystallized from ether-hexane to yield the analytical sample, mp 64°–66° C.

EXAMPLE 52

Preparation of (R,S)-alpha-(1-cyclohexyl)-3-pyridinebutanamine

As in Example 37, hydrolysis of 1.9 g of (R,S)-1-[1-cyclohexyl-4-(3-pyridinyl)butyl]carbamic acid 1,1-dimethylethyl ester in 25 mL of 1N HCl yielded 1.25 g of (R,S)-alpha-(1-cyclohexyl)-3-pyridinebutanamine. Distillation of a portion of the material on a Kugelrohr apparatus (140°–145° C./0.1 mm) yielded the analytical sample.

EXAMPLE 53

Preparation of alpha-[3-(3-pyridinyl)propyl]-3-pyridinepentanoic acid

As in Example 35, 7.16 g of 3-pyridinepentanoic acid was treated with two equivalents of LDA and then reacted with 8.8 g of 3-(3-bromopropyl)pyridine. The usual work-up yielded 8.9 g of an orange colored oil, consisting mainly of alpha-[3-(3-pyridinyl)propyl]-3-pyridinepentanoic acid contaminated by a small amount of starting 3-pyridinepentanoic acid.

EXAMPLE 54

Preparation of [1-[3-(3-pyridinyl)propyl]-4-(3-pyridinyl)butyl]carbamic acid 1,1-dimethylethyl ester As in Example 36, 8.8 g of alpha-[3-(3-pyridinyl)propyl]-3-pyridinepentanoic acid, when reacted with 9.1 g of diphenylphosphorylazide in 75 mL of t-butanol containing 4.1 mL of triethylamine furnished 11.1 g of product. Purification of the crude by HPLC (ethyl acetate-methanol; 13:1) yielded 5.5 g of [1-[3-(3-pyridinyl)-propyl]-4-(3-pyridinyl)butyl]carbamic acid 1,1-dimethylethyl ester as an oil.

EXAMPLE 55

Preparation of alpha-[3-(3-pyridinyl)propyl]-3-pyridinebutanamine

As in Example 37, hydrolysis of 5.4 g of [1-[3-(3-pyridinyl)-propyl]-4-(3-pyridinyl)butyl]carbamic acid 1,1-dimethylethyl ester in 55 mL of 1N HCl yielded 3.15 g of alpha-[3-(3-pyridinyl)propyl]-3-pyridinebutanamine.

EXAMPLE 56

Preparation of (R,S)-alpha-(4-bromophenyl)-3-pyridinepentanoic acid

As in Example 35, 2.15 g of p-bromophenylacetic acid was treated with two equivalents of LDA and then reacted with 2.0 g of 3-(3-bromopropyl)pyridine. The crude product was crystallized from ether-hexane to yield 1.46 g of (R,S)-alpha-(4-bromophenyl)-3-pyridinepentanoic acid, mp 123°–126° C.

EXAMPLE 57

Preparation of (R,S)-[1-(4-bromophenyl)-4-(3-pyridinyl)butyl] carbamic acid 1,1-dimethylethyl ester As in Example 36, 1.45 g of (R,S)-alpha-(4-bromophenyl)-3-pyridinepentanoic acid, when treated with 0.94 mL of diphenylphosphorylazide in 10 mL of t-butanol containing 0.44 g of triethylamine yielded 1.7 g of crude (R,S)-[1-(4-bromophenyl)-4-(3-pyridinyl)-butyl]carbamic acid 1,1-dimethylethyl ester as an oil.

EXAMPLE 58

Preparation of (R,S)-alpha-(4-bromophenyl)-3-pyridinebutanamine

As in Example 37, hydrolysis of 1.7 g of (R,S)-[1-(4-bromophenyl)-4-(3-pyridinyl)butyl]carbamic acid 1,1-dimethylethyl ester in 15 mL of 1N HCl yielded 1.1 g of (R,S)-alpha-(4-bromophenyl)-3-pyridinebutanamine.

EXAMPLE 59

Preparation of [(R,S)-Z]-2-methyl-5-(3-pyridinyl)-4-pentenoic acid

A solution of 9.95 g of [(R,S)-Z]-2-methyl-5-(3-pyridinyl)-4-pentenoic acid ethyl ester in 75 mL of 1N NaOH and 75 mL of methanol were stirred at reflux for 3 hours, then most of the methanol was removed under reduced pressure. After the solution was extracted with dichloromethane (3×50 mL), the aqueous layer was neutralized with 75 ml of 1N HCl and extracted with dichloromethane (4×40 mL). The dried (Na$_2$SO$_4$) extracts were evaporated to give 7.28 g of a solid which was crystallized from ether-hexane to yield 6.12 g of [(R,S)-Z]-2-methyl-5-(3-pyridinyl)-4-pentenoic acid, mp 79°–82° C.

EXAMPLE 60

[(R,S)-Z]-[1-methyl-4-(3-pyridinyl)-3-butenyl]carbamic acid 1,1-dimethylethyl ester As in Example 36, 2.87 g of [(R,S)-Z]-2-methyl-5-(3-pyridinyl)-4-pentenoic acid was reacted with 3.31 mL of diphenylphosphoryl azide in 30 mL of t-butanol containing 2.1 mL of triethylamine. The product was isolated in the usual manner to yield 3.88 g of [(R,S)-Z]-1-[1-methyl-4-(3-pyridinyl)-3-butenyl]carbamic acid 1,1-dimethylethyl ester as an oil.

EXAMPLE 61

[(R,S)-Z]-1-methyl-4-(3-pyridinyl)-3-butenamine

As in Example 37, hydrolysis of 3.88 g of [(R,S)-Z]-[1-methyl-4-(3-pyridinyl)-3-butenyl]carbamic acid 1,1-dimethylethyl ester in 50 mL of 1N HCl yielded, after the usual work-up and evaporative distillation of the product (100°–120° C./0.1 mm), 1.7 g of [(R,S)-Z]-1-methyl-4-(3-pyridinyl)-3-butenamine as an oil.

EXAMPLE 62

Preparation of 3-(4-methyl-4-pentenyl)pyridine

A suspension of 7.0 g of sodium hydride (60% dispersion in oil) in 75 mL of dry dimethylsulfoxide was stirred at 75° C. under argon for 45 minutes, at which time the evolution of hydrogen had ceased. After the solution was cooled, 61 g of methyltriphenylphosphonium bromide was added and the mixture was stirred at room temperature for 30 minutes before the addition of 25 g of 5-(3-pyridinyl)-2-pentanone in 125 mL of dimethylsulfoxide. The reaction was then stirred at room temperature overnight. After the addition of 1 L of 1N hydrochloric acid solution, the precipitated triphenylphosphine oxide was removed by filtration, and the filtrate was basified with 110 mL of 10N sodium hydroxide. The product was extracted with dichloromethane (4×300 ml) and the extracts were washed with brine, then were combined, dried ($K_2CO_3$) and evaporated to give 25 g of crude product. The material was purified by HPLC (ethyl acetate:hexane: 1:1) to yield 17.5 g of 3-(4-methyl-4-pentenyl)pyridine as a colorless oil.

EXAMPLE 63

Preparation of N-[1,1-dimethyl-4-(3-pyridyl)butyl]-2-nitrobenzeneacetamide

A mixture of 22.7 g of 3-(4-methyl-pentenyl)pyridine and 22.8 g of 2-nitrobenzeneacetonitrile in 80 mL of acetic acid was cooled to 12°–13° C. and then 16 mL of sulfuric acid was added dropwise over 6 minutes. The reaction was stirred for 2 hours at ambient temperature, then after the acetic acid was removed in vacuo, 1L of water was added and the mixture was extracted with dichloromethane to remove neutral impurities. The aqueous layer was basified with 10N sodium hydroxide, and extracted with dichloromethane (4×200 mL). The dried ($K_2CO_3$) extracts were evaporated to give 35.6 g of N-[1.1-dimethyl(3-pyridyl)butyl]-2-nitrobenzeneacetamide. A portion was crystallized from ethyl acetate-hexane to yield the analytical sample, mp 117°–118.5° C.

EXAMPLE 64

Preparation of alpha,alpha-dimethyl-3-pyridinebutanamine

A solution of 35.2 g of N-[1,1-dimethyl-4-(3-pyridyl)butyl]-2-nitrobenzeneacetamide in 250 mL of acetic acid was hydrogenated over 3.5 g of 10% Pd/C at atmospheric pressure and ambient temperature. The reaction was exothermic and stopped abruptly after the uptake of the theoretical amount of hydrogen (7.5 L). The catalyst was removed by filtration and the filtrate was heated at reflux for 90 minutes. After the solution was cooled, 10 mL of conc. HCl was added and the solvent was removed under reduced pressure. The residue was taken up in 1 L of water and extracted with ethyl acetate (4×200 mL) to remove the byproduct, oxindole. The aqueous layer was basified with 10N NaOH and extracted with dichloromethane to give, after evaporation of the dried ($K_2CO_3$) extracts 15 g of product. The material was distilled on a Kugelrohr apparatus (95° C.; 0.1 mm) to yield 14.3 g of alpha,alpha-dimethyl-3-pyridinebutanamine.

EXAMPLE 65

Preparation of 4-pyridinepropanamide

In an inert atmosphere 10.7 g of 4-pyridinecarboxaldehyde was added to a stirred solution of 35.1 g of (carbomethoxy)methylenetriphenylphosphorane in 250 mL of methanol. After 90 minutes, the solvent was removed under reduced pressure and the residue was triturated with etherhexane. The resulting solid (triphenylphosphine oxide) was removed by filtration, and the filtrate was evaporated to yield 18 g of a mixture of (E)- and (Z)-3-(4-pyridinyl)-2-propenoic acid methyl ester contaminated with a small amount of residual triphenylphosphine oxide.

The crude mixture (18 g) was hydrogenated over 1.6 g of 10% Pd/C in 200 mL of methanol at atmospheric pressure and room temperature. After the uptake of hydrogen had stopped, the catalyst was removed by filtration and the solvent was removed in vacuo to furnish 16 g of crude 4-pyridinepropanoic acid methyl ester.

The crude ester was dissolved in 250 mL of 7.1M methanolic ammonia solution and was stirred at room temperature for 65 hours. After the solvent and excess ammonia were removed by distillation under reduced pressure, the residue was dissolved in 150 mL of 1N HCl and extracted with dichloromethane to remove residual triphenylphosphine oxide. The aqueous phase was basified with 40 mL of 4N NaOH and then was extracted with ethyl acetate (5×300 mL). The dried ($Na_2SO_4$) extracts weer evaporated to furnish 6 g of the amide. The aqueous layer was concentrated to dryness and triturated with tetrahydrofuran (4×100 mL) and evaporation of the tetrahydrofuran extracts yielded an additional 5 g of amide. The combined crude products were dried, triturated with ether and the solids were filtered to yield 10.7 g of 4-pyridinepropanamide, mp 164°–166° C.

EXAMPLE 66

Preparation of 4-pyridinepropanamine

A 1M solution of $BH_3$ in tetrahydrofuran (192 mL) was added over 10 minutes to a stirred suspension of 7.2 g of 4-pyridinepropanamide in 50 mL of tetrahydrofuran at 0°–5° C. After the cooling bath was removed, the reaction was stirred at reflux for 17 hours and then the solvent was removed in vacuo. The residue was dissolved in 160 mL of 3.5N HCl and after the solution was heated on a steam bath overnight, it was cooled, basified with excess 10N NaOH and then extracted with dichloromethane. The dried ($K_2CO_3$) extract was evaporated to furnish 6.98 g of an amber oil, which was distilled in vacuo to give 4.3 g of 4-pyridinepropanamine (bp 100°–110° C./0.2 mm).

EXAMPLE 67

Preparation of 5-(2-pyridinyl)-4-pentyn-1-ol

As in Example 1, 15.8 g of 2-bromopyridine and 8.4 g of 4-pentyn-1-ol were reacted together in 125 mL of dichloromethane in the presence of 4.2 mL of triethylamine, 2.1 g of bis(triphenylphosphine)palladium dichloride and 0.135 g of cuprous iodide. After 48 hours at reflux, the reaction was worked up in the usual manner. Distillation of the crude product yielded 8.8 g of 5-(2-pyridinyl)-4-pentyn-1-ol (bp 115°–120° C./0.25 mm).

EXAMPLE 68

Preparation of 2-pyridinepentanol 5-(2-Pyridinyl)-4-pentyn-1-ol (8.8 g) was hydrogenated over 1.0 g of 10% Pd/C in 125 mL of ethanol at room temperature and atmospheric pressure. After the uptake of hydrogen had stopped, the catalyst was removed by filtration and the solvent was removed under reduced pressure. The residual oil was distilled on a Kugelrohr apparatus (115°–120° C./0.1 mm) to yield 8.4 g of 2-pyridinepentanol.

EXAMPLE 69

Preparation of 2-(5-chloropentyl)pyridine

A solution of 4.1 mL of thionyl chloride in 30 mL of dichloromethane was added over 10 minutes to a stirred solution of 6.65 g of 2-pyridinepentanol in 60 mL of dichloromethane maintained at −5° C. After the addition was complete, the mixture was stirred at room temperature for 17 hours, then was rechilled to 5° C. as 150 ml of 1N NaOH was added dropwise over 10 minutes. The layers were separated and the aqueous layer was extracted with 75 mL of dichloromethane. The organic layers were washed with brine, then were combined, dried ($K_2CO_3$) and evaporated to yield 7.4 g of 2-(5-chloropentyl)pyridine as an oil.

EXAMPLE 70

Preparation of 1-[5-(2-pyridinyl)pentyl]-1H-isoindole-1,3-(2H)-dione

A mixture of 6.35 g of 2-(5-chloropentyl)pyridine, 7.7 g potassium phthalimide, 5.2 g of sodium iodide and 3.7 g of sodium carbonate in 50 mL of dimethylformamide was stirred at 50° C. for 20 hours. After the solvent was removed under reduced pressure, the residue was taken up in 100 mL of water and extracted with dichloromethane (1×250 mL; 1×150 mL). The organic extracts were washed with brine, then were combined, dried ($K_2CO_3$) and concentrated in vacuo to give 10.1 g of an orange colored oil. Purification of the crude material by HPLC (ethyl acetate-hexane) yielded 6.7 g of 1-[5-(2-pyridinyl) pentyl]-1H-isoindole-1,3-(2H)-dione.

EXAMPLE 71

Preparation of 2-pyridinepentanamine

A solution of 6.5 g of 1-[5-(2-pyridinyl)pentyl]-1H-isoindole-1,3-(2H)-dione and 1.15 mL of hydrazine hydrate in 35 mL of ethanol was heated at reflux for 90 minutes. The cooled reaction mixture was treated with 10 ml of 6N HCl, and the solids were removed by filtration and washed with 20 mL of 0.5N HCl. After the filtrate was concentrated to remove ethanol, it was basified with 10N NaOH and extracted with dichloromethane. The organic extract was washed with brine, then was dried ($K_2CO_3$) and evaporated to give 3.4 g of a yellow oil. The crude reaction product was evaporatively distilled (105°–110° C./0.01 mm) to yield 2.4 g of 2-pyridinepentanamine.

EXAMPLE 72

Preparation of 3-(8-isoquinolinyl)-2-propyn-1-ol

In an inert atmosphere, 0.068 g of bis(triphenylphosphine)palladium dichloride and 0.013 g of cuprous iodide was added with stirring to a deoxygenated solution of 1 g of 8-bromoisoquinoline, 0.56 mL of propargyl alcohol and 2 mL of triethylamine in 25 mL of dichloromethane. The mixture was stirred at room temperature for 2 hours and then at reflux for 20 hours. The cooled reaction was filtered and the filtrate was concentrated in vacuo. The residual oil was purified by HPLC (ethyl acetate-toluene; 2:3) to yield 0.4 g of 3-(8-isoquinolinyl)-2-propyne-1-ol, mp 138°–139° C.

EXAMPLE 73

Preparation of 8-isoquinolinepropanol

A solution of 0.4 g of 3-(8-isoquinolinyl)-2-propyn-1-ol in a mixture of 10 mL of ethanol and 5 mL of methanol was hydrogenated over 0.06 g 10% Pd/C at room temperature and atmospheric pressure for 22 hours and then at 50 psi for 20 hours. After the catalyst was removed by filtration and the filtrate was concentrated, the residual oil was purified by HPLC (methanol-chloroform; 1:19) and crystallized from ethyl acetate-hexane to yield 0.136 g of 8-isoquinolinepropanol, mp 66°–69° C.

EXAMPLE 74

Preparation of [3-(8-isoquinolinyl)propyl]-1H-isoindole-1,3-(2H)-dione

A solution of 0.142 g of 8-isoquinolinepropanol in 3 mL of chloroform was added to a solution of 0.085 mL of thionyl chloride in 1 mL of chloroform and the reaction was stirred at reflux for 3 hours. The cooled mixture was washed with $NaHCO_3$ solution and with brine, then was dried ($Na_2SO_4$) and evaporated. The residual oil was stirred with 0.281 g of potassium phthalimide and 0.126 potassium iodide in 3 mL of dry dimethylformamide at 130° C. for 90 minutes. After evaporation of the solvent, the residue was partitioned between dichloromethane and water. The dried ($Na_2SO_4$) organic layer was concentrated and the crude product was purified by HPLC (ethyl acetate-toluene; 1:4) and then crystallized from ether to give 0.177 g of [3-(8-isoquinolinyl)propyl]-1H-isoindole-1,3-(2H)-dione, mp 135°–140° C.

EXAMPLE 75

Preparation of 8-isoquinolinepropanamine

To a refluxing solution of 0.174 g of [3-(8-isoquinolinyl)propyl]-1H-isoindole-1,3-(2H)-dione in 8 mL of ethanol was added 0.12 mL of hydrazine hydrate and the reaction was stirred at reflux for 5.5 hours. The solvent was removed under reduced pressure and the residue was triturated with chloroform. The chloroform extract was concentrated to an oil which was passed through a short column of silica gel (chloroform-methanoltriethylamine; 1:4:15) to yield 0.103 g of 8-isoquinolinepropanamine as an oil.

EXAMPLE 76

Preparation of 4-(4-isoquinolinyl)-3-butyn-1-ol

In an inert atmosphere, 0.268 g of bis(triphenylphosphine) palladium dichloride and 0.072 g of cuprous iodide was added with stirring to a deoxygenated solution of 5 g of 4-bromoisoquinoline, 3.02 g of 3-butyn-1-ol and 10 mL of triethylamine in 20 mL of dichloromethane. The reaction was stirred at room temperature for 1 hour and then at reflux for 18 hours. The cooled mixture was filtered and the filtrate was washed with water. The dried ($Na_2SO_4$) organic phase was concentrated in vacuo and the residual oil was purified by HPLC (ethyl acetate-toluene; 2:3) to yield 3.4 g of 4-(4-isoquinolinyl)-3-butyn-1-ol as an oil.

EXAMPLE 77

Preparation of (E)-4-(4-isoquinolinyl)-3-buten-1-ol

A solution of 3.4 g of 4-(4-isoquinolinyl)-3-butyn-1-ol in 35 mL of ethanol was hydrogenated over 0.35 g of 10% Pd/C at room temperature and atmospheric pressure for 5 hours. The catalyst was removed by filtration and the filtrate was evaporated to yield 3.3 g of (E)-4-(4-isoquinolinyl)-3-buten-1-ol as an oil.

EXAMPLE 78

Preparation of (E)-4-(4-chloro-1-butenyl)isoquinoline

A solution of 3.3 g of (E)-4-(4-isoquinolinyl)-3-buten-1-ol in 15 mL of dry chloroform was added to a cold solution of 1.8 mL of thionyl chloride in 5 mL of dry chloroform. After 15 minutes, the cooling bath was removed and the reaction was stirred at room temperature for 1 hour and then at reflux for 3 hours. The cooled mixture was washed with NaHCO$_3$ solution and with brine, then was dried (Na$_2$SO$_4$) and evaporated. The residue was purified by chromatography over silica gel (ethyl acetate-toluene; 3:17) to yield 2.2 g of (E)-4-(4-chloro-1-butenyl)isoquinoline as an oil.

EXAMPLE 79

Preparation of (E)-1-[4-(4-isoquinolinyl)-3-butenyl]-1H-isoindole-1,3-(2H)-dione A mixture of 2.2 g of (E)-4-(4-chloro-1-butenyl) isoqunioline, 3.8 g of potassium phthalimide and 1.7 g of potassium iodide in 20 mL of dry dimethylformamide was maintained at 130° C. for 5 hours. After evaporation of the solvent, the residue was partitioned between dichloromethane and water. The dried (Na$_2$SO$_4$) organic layer was concentrated and the crude product was purified by chromatography over silica gel (ethyl acetate-toluene; 3:7) to yield 1.75 g of (E)-1-[4-(4-isoquinolinyl)-3-butenyl]-1H-isoindole-1,3-(2H)-dione, mp 135°-140°.

EXAMPLE 80

Preparation of (E)-4-(4-isoquinolinyl)-3-buten-1-amine

To a refluxing solution of 1.75 g of (E)-1-[4-(4-isoquinolinyl)-3-butenyl]-1H-isoindole-1,3-(2H)-dione in 80 mL of ethanol was added 1.1 mL of hydrazine hydrate and the reaction was stirred at reflux for 17 hours. The solvent was removed in vacuo and the residue was triturated with chloroform. The extract was concentrated to yield 1 g of (E)-4-(4-isoquinolinyl)-3-buten-1-amine as an oil.

EXAMPLE 81

Preparation of 4-isoquinolinebutanamine

A solution of 1 g of (E)-4-(4-isoquinolinyl)-3-buten-1-amine in 20 mL of ethanol was hydrogenated over 0.12 g of 10% Pd/C at room temperature and atmospheric pressure. After 8 hours, the catalyst was removed by filtration and the filtrate was concentrated to yield 0.893 g of 4-isoquinolinebutanamine.

EXAMPLE 82

2,3'-Difluorobenzophenone hydrazone

A solution of 3,3'-difluorobenzophenone (76.4 g) and 95% hydrazine hydrate (56 mL) in n-butanol (225 mL) was heated at reflux under argon for 3 hours and then 100 mL of solvents were distilled off. The reaction was colled and distibuted between toluene (1.2 L) and water (400 mL). The separated organic layer was washed with water (4×400 mL) and then each aqueous wash was back-extracted in turn with toluene (100 mL). The combined toluene extracts were dried (K$_2$CO$_3$) and evaporated under reduced pressure to furnish 80 g of the crude hydrazone as an oil. The material was dissolved in hot hexane and the resulting solution cooled slowly to room temperature with stirring. The resulting solids were collected by filtration, washed with hexane and dried to provide 72.1 g of 3,3'-difluorobenzophenone hydrazone, mp 35°-36° C.

EXAMPLE 83

2,2-Diphenylcyclopropanecarboxaldehyde

A solution of diisobutylaluminum hydride in hexane (25%; 212 mL) was added over 30 minutes to a solution of 2,2-diphenylcyclopropanecarbonitrile (45.4 g) in dry toluene (400 mL) maintained at −40° C. during the addition. After the reaction had been stirred at room temperature for 1 hour, it was rechilled to 0°-5° C. and 2N sulfuric acid (400 mL) was added dropwise. The two phase system was stirred at ambient temperature for 1 hours then the layers were separated and the aqueous phase was extracted with ethyl acetate (2×300 mL). The organic layers were washed with Rochelle salt solution (5%; 2×200 mL), then were dried (Na$_2$SO$_4$) and evaporated to give 2,2-diphenylcyclopropanecarboxaldehyde as a solid, mp 71°-73° C. A sample was crystallized from benzene-hexane to provide the purified aldehyde, mp 75°-76° C.

EXAMPLE 84

2,2-bis(3-Fluorophenyl)cyclopropanecarboxaldehyde

A stirred solution of 3,3'-difluorobenzophenone hydrazone (176 g) in dichloromethane (845 mL) was cooled to 8° C. and activated manganese dioxide (267 g) was added portionwise over 10 minutes such that the reaction temperature did not exceed 15° C. The mixture was stirred at room temperature for 2.5 hours, then was filtered and the solidss washed with dichloromethane. The deep purple filtrate containing the bis(3-fluorophenyl)diazomethane was added dropwise to a solution of acrolein (64 mL) in hexane (750 mL) with stirring over 20 minutes. The reaction temperature was held at 25° C. throughout the addition. After 90 minutes at 25° C. the evolution of nitrogen had significantly decreased, so the reaction was gradually raised to 50° C. over 2 hours. Towards the end of this period, the original intense violet color of the mixture had faded to a pale amber. The solvents were removed under reduced pressure and the residue was passed through a short column of silica gel (1 Kg) made up in dichloromethane-hexane (2:1). The appropriate cuts were combined to give 84.7 g of 2,2-bis(3-fluorophenyl)cyclopropanecarboxaldehyde. A portion of the aldehyde was crystallized from hexane to provide the analytical sample, mp 49°-51° C.

Anal. Calculated for C$_{16}$H$_{12}$F$_2$O: C, 74.41; H, 4.68; /F, 14.71. Found: C, 73.95; H, 4.83; F, 14.95.

EXAMPLE 85

2,2-bis(3-Fluorophenyl)-1-methylcyclopropanecarboxaldehyde

A solution of bis(3-fluorophenyl)diazomethane, prepared as in Example 84 by the action of activated manganese dioxide (33 g) on 3,3'-difluorobenzophenone hydrazone (21.76 g) in dichloro-methane (105 mL), was added to a solution of methacrolein (15 mL) in hexane (100 mL). The mixture was heated at 43° C. for 20 hours then the amber solution was evaporated in vacuo. The crude solid was triturated with hexane to yield 23.1 g of 2,2-bis(3-fluorophenyl)-1-methylcyclopropanecarboxaldehyde, mp 92°–93° C. Recrystallization of a sample from hexane furnished the analytical specimen, mp 92°–93.5° C.

Anal. Calculated for $C_{17}H_{14}F_2O$: C, 74.99; H, 5.18; F, 13.96. Found: C, 74.79; H, 5.26; F, 13.93.

EXAMPLE 86

2,2-bis(4-Fluorophenyl)cyclopropanecarboxaldehyde

A solution of bis(4-fluorophenyl)diazomethane, prepared as in Example 84 from the action of activated manganese dioxide (59.7 g) on 4,4'-difluorobenzophenone hydrazone (42.81 g) in dichloromethane (195 mL), was added to a solution of acrolein (15.7 mL) in heptane (150 mL). The deep purple reaction mixture, after being stirred at 40° C. for 2 hours then at 53° C. for 30 minutes, faded to a pale amber color. Evaporation of the solvents afforded 46 g of 2,2-bis(4-fluorophenyl)cyclopropanecarboxaldehyde as an oil. The material was used without further purification in subsequent reactions.

EXAMPLE 87

2,2-bis(4-Fluorophenyl)-1-methylcyclopropanecarboxaldehyde

A solution of bis(4-fluorophenyl)diazomethane, prepared as above from the action of activated manganese dioxide (32.3 g) on 4,4'-difluorobenzophenone hydrazone (23.2 g) in dichloromethane (105 mL), was added to a solution of methacrolein (12.5 mL) in heptane (100 mL). The mixture was heated at 40° C. for 6 hours then the amber colored solution was evaporated in vacuo. The resulting solid was triturated with hexane (100 mL) to give 22.0 g of 2,2-bis(4-fluorophenyl)-1-methylcyclopropanecarboxaldehyde, mp 110°–113° C. Recrystallization of a sample from hexane provide the analytical specimen, mp 111°–113° C.

Anal. Calculated for $C_{17}H_{14}F_2O$: C, 74.99; H, 5.18; F, 13.96. Found: C, 74.98; H, 5.15; F, 13.66.

EXAMPLE 88

2,2-bis[3-(Trifluoromethyl)phenyl]cyclopropanecarboxaldehyde

A solution of bis[3-(trifluoromethyl)phenyl]diazomethane, prepared as in Example 84 from 3,3'-(trifluoromethyl)benzophenone hydrazone (29.9 g) and activated manganese dioxide (30 g) in dichloromethane (150 mL) was added to a solution of acrolein (9.9 mL) in heptane (90 mL) over 15 minutes at 40° C. The solution was heated at 55° C. for 5.5 hours, then the dichloromethane was distilled off and replaced with heptane (100 mL). After the mixture was heated at 90° C. overnight, the solvent was removed in vacuo and the residue was purified by HPLC (dichloromethanehexane; 1:1). Evaporation of the appropriate fractions yielded 30.5 g of 2,2-bis[3-(trifluoromethyl)phenyl]cyclopropanecarboxaldehyde. Crystallization of a portion from hexane gave the analytical sample, 106°–108° C.

Anal. Calculated for $C_{18}H_{12}F_6O$: C, 60.34; H, 3.38; F, 31.82. Found: C, 59.59; H, 3.32; F, 32.98.

EXAMPLE 89

2,2-bis(3-Methoxyphenyl)cyclopropanecarboxaldehyde

A solution of bis(3-methoxyphenyl)diazomethane, prepared as in Example 84 from 3,3'-dimethoxybenzophenone hydrazone (2.45 g) and activated manganese dioxide (3.2 g) in dichloromethane (15 mL), was added to a stirred solution of acrolein (0.73 mL) in heptane (10 mL) over 15 minutes at 40° C. After 45 minutes at 40° C., the solution had changed from intense purple to pale pink in color. The dichloromethane was then distilled off, heptane (10 mL) added and the mixture stirred at reflux for 1 hour. Evaporation of the solution and purification of the residue by using HPLC (ethyl acetate-hexane; 1:4) afforded 1.5 g of 2,2-bis(3-methoxyphenyl)cyclopropanecarboxaldehyde as an oil.

Anal. Calculated for $C_{18}H_{18}O_3$: C, 76.57; H, 6.43. Found: C, 76.51; H, 6.18.

EXAMPLE 90

2,2bis(3-Methoxyphenyl)-1-methylcyclopropanecarboxaldehyde

A solution of bis(3-methoxyphenyl)diazomethane, prepared as in Example 84 from 3,3'-dimethoxybenzophenone hydrazone (18.7 g) and activated manganese dioxide (24.3 g) in dichloromethane (125 mL) was added to a solution of methacrolein (10.8 mL) in heptane (70 mL) over 10 minutes at 40° C. The mixture was stirred at 40° C. for 16 hours, and then after the dichloromethane was distilled off, at 85° C. for 1 hour. The solvent was removed in vacuo and the residue was purified by HPLC (ethyl acetate-hexane; 1:5) to yield 8.0 g of 2,2-bis(3-methoxyphenyl)1-methylcyclopropanecarboxaldehyde. Crystallization of the material from ethyl acetate-hexane provided 6.2 g of the aldehyde, mp 122°–123° C.

Anal. Calculated for $C_{19}H_{20}O_3$: C, 77.00; H, 6.80. Found: C, 77.24; H, 6.79.

EXAMPLE 91

[1(R,S),2(R,S)]-2-(3-Methoxyphenyl)-2-phenylcyclopropanecarboxaldehyde and

[1(R,S),2(S,R)]-2-(3methoxyphenyl)-2-phenylcyclopropanecarboxaldehyde

A solution of 1-(3-methoxyphenyl)-1-phenyldiazomethane, prepared as in Example 84 from 3-methoxybenzophenone hydrazone (85.3 g) and activated manganese dioxide (127 g) in dichloromethane (400 mL), was added to a solution of acrolein (31.5 mL) in hexane (70 mL) over 2.5 hours at 15° C. After the mixture was stirred at 20° C. for 16 hours the solvent was removed in vacuo and the residue was purified by HPLC (ethyl acetate-dichloromethane hexane; 1:2:11) to yield 75.6 g of a mixture (1:1) of the diastereomeric pairs, [1(R,S),2(R,S)]-2-(3-methoxyphenyl)-2-phenylcyclopropanecarboxaldehyde and [1(R,S),2(S,R)]-2-(3-methoxyphenyl)-2-phenylcyclopropanecarboxaldehyde as an oil.

EXAMPLE 92

[R,S-(E)]-3-(2,2-Diphenylcyclopropyl)-2-propenoic acid and

[R,S-(Z)]-3-(2,2-diphenylcyclopropyl)-2-propenoic acid

A solution of 2,2-diphenylcyclopropanecarboxaldehyde (78.4 g) and (carbethoxymethylene)triphenylphosphorane (123 g) in ethanol (400 mL) was stirred at room temperature over 30 minutes. The solvent was removed in vacuo and the residual material was taken up in an ether-hexane mixture (2:3; -800 mL) and left overnight at 0° C. After the precipitated triphenylphosphine oxide was removed by filtration, the filtrate was evaporated and the residue was passed through a short column of silica gel (1 Kg) made up in dicloromethane. Evaporation of the appropriate fractions gave 95 g of the mixture of (E)- and (Z)-esters. These were separated by HPLC (ether-hexane; 1:19) to give 34.2 g of the less polar [R,S-(Z)]-3-(2,2-diphenylcyclopropyl)-2-propenoic acid ethyl ester and 55 g of [R,S-(E)]-3-(2,2-diphenylcyclopropyl)-2-propenoic acid ethyl ester as oils.

A solution of [R,S-(Z)]-3-(2,2-diphenylcyclopropyl)-2-propenoic acid ethyl ester (34.2 g) in methanol (200 mL) was treated with 4N potassium hydroxide solution (50 mL) and was heated at reflux for 1.5 hours. The mixture was diluted with water (200 mL) and after the methanol was removed under reduced pressure, it was extracted with ether (100 mL). Acidification of the separated aqueous layer with 6N hydrochloric acid (40 mL) furnished a dense colorless precipitate which was recovered by filtration, washed with water and dried to provide 29.1 g of [R,S-(Z)]-3-(2,2-diphenylcyclopropyl)-2-propenoic acid, mp 135°–139° C. Crystallization from ether furnished the analytical specimen, mp 141.5°–142.5° C.

Anal. Calculated for $C_{18}H_{16}O_2$: C, 81.79; H, 6.10. Found: C, 82.07; H, 6.04.

Under the same conditions, [R,S-(E)]-3-(2,2-diphenylcyclopropyl)-2-propanoic acid ethyl ester (55 g) in methanol (350 mL) was saponified with 4N potassium hydroxide (87.5 mL). The usual work up afforded 49.1 g of [R,S-(E)]-3-(2,2-diphenylcyclopropyl)-2-propenoic acid, mp 171.5°–173.5° C. Crystallization from 2-propanol afforded the analytical sample, mp 175.5°–177.5° C.

Anal. Calculated for $C_{18}H_{16}O_2$: C, 81.79; H, 6.10. Found: C, 82.01; H, 6.11.

EXAMPLE 93

[R-(E)]-3-(2,2-Diphenylcyclopropyl)-2-propenoic acid and [S-(E)]-3-(2,2-diphenylcyclopropyl)-2-propanoic acid A stirred solution of racemic (E)-3-(2,2-diphenylcyclopropyl)-2-propenoic acid (44.9 g) in hot methanol (700 mL) was treated with cinchonidine (50 g) and the solution was stirred at room temperature for 1 hour and then at 0° C. for 1 hour. The precipitated salt was recovered by filtration, washed with cold methanol and dried to give 53 g of the crude cinchonidine salt of the (−)-acid, mp 214° c. A slurry of the salt in methanol (350 mL) was stirred at reflux for 30 minutes, then was cooled to 10°–15° C. and the solids filtered to give 39.1 g of [S-(E)]-3-(2,2-diphenylcyclopropyl)-2-propenoic acid cinchonidine salt, mp 224° C.

The combined mother liquors from above were evaporated and the residue was distributed between dichloromethane (250 mL) and 1N hydrochloric acid (250 mL). The separated aqueous layer was extracted with dichloromethane (2×50 mL) and the organic layers were washed with 1N hydrochloric acid (2×50 mL) and with water (50 mL). The dried (MgSO4) extracts were evaporated to give 21.5 g of acid enriched in the (+)-isomer. A solution of this impure (+)-acid (17.7 g; 0.067 mol) in methanol (75 mL) was combined with (−)-alphamethyl -p-nitrobenzylamine (12.8 g) in methanol (25 mL). The mixture was left at room temperature for 4 hours and then the solids were recovered by filtration, washed with methanol and ether to give 22.3 g of [R-(E)]-3-(2,2-diphenylcyclopropyl)-2-propenoic aicd (−)-alpha methyl-p-nitrobenzylamine salt, mp 170.5°–171.5° C.

The cinchonidine salt of the (S)-acid from above (39.6 g) was distributed between dichlormethane (250 mL) and 1N hydrochloric acid (250 mL) and the aqueous layer was re-extracted with dichlormethane (2×50 mL). The organic layers were washed with 1N hydrochloric acid (2×50 mL), then combined, dried (MgSO4) and evaporated to yield 18.4 g of [S-(E)]-3-(2,2-diphenylcyclopropyl)-2-propenoic acid, mp 148°–149° C. Crystallization of a sample from ether-hexane afforded the analytical specimen, mp 149°–150° C; $[\alpha]_D^{25}$ −247° (c, 1.0, MeOH)

Anal. Calculated for $C_{18}H_{16}O_2$: C, 81.79; H, 6.10. Found: C, 81.42; H, 6.16.

In the same manner, the [R-(E)]-3-(2,2-diphenylcyclopropyl)-2-propenoic acid (−)-alpha-methyl-p-nitrobenzylamine salt (22.3 g) was split to give 14.5 g of [R-(E)]-3-(2,2-diphenylcyclopropyl)-2-propenoic acid, mp 148°–149° C. Crystallization from ether-hexane furnished the analytical sample, mp 150.5°–151.5° C; $[\alpha]_D^{25}$ 250.3°(c, 1.0, MeOH)

Anal. Calculated for $C_{18}H_{16}O_2$: C, 81.79; H, 6.10. Found: C, 82.10; H, 5.81.

EXAMPLE 94

[R-(Z)]-3-(2,2-Diphenylcyclopropyl)-2-propenoic acid and [S-(Z)]-3-(2,2-diphenylcyclopropyl)-2-propenoic acid To a stirred solution of [R,S-(Z)]-3-(2,2-diphenylcyclopropyl)-2-propenoic acid (37.8 g) in methanol (700 mL) was added a solution of (+)-alpha-methyl-p-nitrobenzylamine (23.8 g) in methanol. After 4 hours at room temperature, the crystalline salt that had formed was filtered and washed with methanol. The salt (23.8 g) was recrystallized from methanol to give 18.7 g of the [R-(Z)]-3-(2,2-diphenylcyclopropyl)-2-propenoic acid (+)-alpha-methyl-p-nitrobenzylamine salt, mp 120°–121° C.

The above salt (18.7 g) was split by distribution between dichloromethane and 1N hydrochloric acid in the usual fashion to give 10.45 g of [R-(Z)]-3-(2,2-diphenylcyclopropyl)-2-propenoic acid. A sample was crystallized from ether-hexane to furnish the analytical specimen, mp 96°–97° C.; $[\alpha]_D^{25}$ −170.6° (c, 1.0, MeOH).

Anal. Calculated for $C_{18}H_{16}O_2$: C, 81.79; H, 6.10. Found: C, 82.06; H, 6.16.

The mother liquor from the original crystallization was evaporated and the residual non-crystalline salt was split in the usual manner to give 25.5 g of crude acid rich in the (+)-isomer. This material was dissolved in methanol (500 mL) containing (−)-alpha-methyl-p-nitrobenzylamine (16 g). After 2 hours the precipitated salt was recovered by filtration and recrystallized from methanol (400 mL) to yield 23.5 g of the [S-(Z)]-3-(2,2-diphenylcyclopropyl)-2-propenoic acid (−)-alpha-methyl-p-nitrobenzylamine salt, mp 121°–122° C.

The above salt (23.3 g) was split in the usual manner to give 14 g of [S-(Z)]-3-(2,2-diphenylcyclopropyl)-2-propenoic acid. A sample was crystallized from ether-hexane to provide the analytical specimen, mp 96°–97° C.; $[\alpha]_D^{25}$ ×168.05° (c, 1.0, MeOH)

Anal. Calculated for $C_{18}H_{16}O_2$: C, 81.79; H, 6.10. Found: C, 82.04; H, 6.24.

EXAMPLE 95

[R-(E)]-(2,2-Diphenylcyclopropyl)-2-propenoic acid 4-bromophenyl ester

A solution of (+)-(E)-(2,2-diphenylcyclopropyl)-2-propenoic acid (0.792 g) and 4-bromophenol (0.53 g) in dichloromethane (10 mL) was treated with 1,3-dicyclohexylcarbodiimide (0.62 g) and the mixture was stirred at room temperature for 2 hours. After the solids were filtered off, the solvent was evaporated and the residue passed through a column of silica gel (15 g) made up in dichloromethane. Evaporation of the appropriate fractions yielded 0.8 g of (+)-(E)-(2,2-diphenylcyclopropyl)-2-propenoic acid 4-bromophenyl ester. A portion was crystallized from 2-propanol to give the pure ester, mp 116.5°–117.5° C; $[\alpha]_D^{25}+195.1°$ (c, 1.0, MeOH).

Anal. Calculated for $C_{24}H_{19}BrO_2$: C, 68.75; H, 4.57; Br, 19.06. Found: C, 68.49; H, 4.58; Br, 19.19.

The ester [R-(E)]-(2,2-diphenylcyclopropyl)-2-propenoic acid 4-bromophenyl ester was determined to have the R absolute configuration by X-ray crystallography. On this basis, the acid precursor of [R-(E)]-(2,2-diphenylcyclopropyl)-2-propenoic acid 4-bromophenyl ester, (+)-(E)-3-(2,2-diphenylcyclopropyl)-2-propenoic acid was assigned the R configuration. Furthermore, since both (+)-E)-3-(2,2-diphenylcyclopropyl)-2-propanoic acid and (−)-(Z)-3-(2,2-diphenylcyclopropyl)-2-propenoic acid yield the same compound when hydrogenated over Raney Ni, i.e., (+)-2,2-diphenylcyclopropanepropanoic acid (vide infra), (−)-(Z)-3-(2,2-diphenylcyclopropyl)-2-propenoic acid and (+)-2,2-diphenylcyclopropanepropanoic acid could also be assigned the R configuration.

EXAMPLE 96

[R,S-(E)]-3-[2,2-bis(3-Fluorophenyl)cyclopropyl]-2-propenoic acid and
[R,S-(Z)]-3-[2,2-bis(3-fluorophenyl)cyclopropyl]-2-propenoic acid As in Example 92, 2,2-bis(3-fluorophenyl)cyclopropanecarboxaldehyde (30 g) and (carbomethoxymethylene)triphenylphosphorane (41 g) were reacted together in methanol (250 mL). The mixture obtained from the usual work up was separated by HPLC (dichloromethane-hexane; 1:2) to give 14.7 g of [R,S-(Z)]-3-[2,2-bis(3-fluorophenyl)cyclopropyl]-2-propenoic acid methyl ester and 19 g of [R,S-(E)-3-[2,2-bis(3-fluorophenyl)cyclopropyl]-2-propenoic acid methyl ester, both as oils.

The minor component, [R,S-(Z)]-3-bis[2,2-(3-fluorophenyl)-cyclopropyl]-2-propenoic acid methyl ester (14.7 g) was saponified in the normal fashion in a mixture of methanol (100 mL) and 2N sodium hydroxide solution (45 mL) over 30 minutes at reflux. The usual work up furnished 14 g of crude acid, which was crystallized from ether-hexane to yield 11.9 g of [R,S-(Z)]-3-[2,2-bis(3-fluorophenyl)cyclopropyl]-2-propenoic acid, mp 139°–141° C.

Anal. Calculated for $C_{18}H_{14}F_2O_2$: C, 71.99; H, 4.70; F, 12.65. Found: C, 71.95; H, 4.58; F, 12.65.

In the same manner, [R,S-(E)]-3-[2,2-bis(3-fluorophenyl)cyclopropyl]-2-propenoic acid methyl ester (19 g) was saponified in a mixture of methanol (150 mL) and 2N sodium hydroxide solution (65 mL) over 15 minutes at reflux. The normal work up, after crystallization of the crude product from ether-hexane, afforded 15.8 g of [R,S-(E)]-3-[2,2-bis(3-fluorophenyl)cyclopropyl]-2-propenoic acid, mp 134°–136° C. Recrystallization from ether gave the pure acid, mp 136°–138° C.

Anal. Calculated for $C_{18}H_{14}F_2O_2$: C, 71.99; H, 4.70; F, 12.65. Found: C, 72.11; H, 4.67; F, 12.57.

EXAMPLE 97

[R-(E)]-3-[2,2-bis(3-Fluorophenyl)cyclopropyl]-2-propenoic acid and
[S-(E)]-3-[2,2-bis(3-fluorophenyl)cyclopropyl]-2-propenoic acid Cinchonidine (45 g) was added to a stirred solution of racemic (E)-3-[2,2-bis(3-fluorophenyl)cyclopropyl]-2-propenoic acid (54.1 g) in hot 2-propanol (600 mL and the mixture was left at room temperature for 4 hours. The solid that formed was filtered and washed with 2-propanol to give 49.5 g of partially resolved salt, mp 212.5°–214° C. The salt was recrystallized twice from 2-propanol to afford 42.5 g of [S-(E)]-3-[2,2-bis(3-fluorophenyl)cyclopropyl]-2-propenoic acid cinchonidine salt, mp 216°–217° C.

Evaporation of the original mother liquors furnished an oil that was distributed between 1N hydrochloric acid (250 mL) and dichloromethane (250 mL). The organic phase was washed with 1N hydrochloric acid (2×100 mL) and the aqueous layers were extracted with dichloromethane (100 mL). Evaporation of the combined organic extracts gave 30 g of partially resolved (+)-acid. This material (30 g) was combined with (−)-alpha-methyl-p-nitrobenzylamine (16 g) in 2-propanol (700 mL) and the mixture was stored at 0° C. for 2 hours. The copious precipitate was filtered off to yield 36.8 g of salt, mp 168°–171° C., which was recrystallized from 2-propanol (650 mL) to furnish 35.4 g of [R-(E)]-3-[2,2-bis(3-fluorophenyl)cyclopropyl]-2-propenoic acid (−)-alpha-methyl-p-nitrobenzylamine salt, mp 172°–174° C.

The combined mother liquors collected from the various recrystallizations of the above salts were evaporated and the residual salts were split in the usual manner to give 8 g of slightly levorotary acid. This material was treated with cinchonidine (6 g) in 2-propanol. The resulting solid was collected and recrystallized (2×) from 2-propanol to give an additional 6.1 g of the (S)-acid cinchonidine salt, mp 215.5°–217° C.

The (S)-acid cinchonidine salts from above (48.9 g) were split in the usual manner to furnish [S-(E)]-3-[2,2-bis(3-fluorophenyl)cyclopropyl]-2-propenoic acid (24.5 g). Recrystallization from ether-hexane yielded 22.7 g of the acid, mp 128°–129° C.; $[\alpha]_D^{25}-221.05°$ (c, 1.0, MeOH)

Anal. Calculated for $C_{18}H_{14}F_2O_2$: C, 71.99; H, 4.70; F, 12.65. Found: C, 71.75; H, 4.61; F, 12.83.

The [R-(E)]-3-[2,2-bis(3-fluorophenyl)cyclopropyl]-2-propenoic acid (−)-alpha-methyl-p-nitrobenzylamine salt from above (35.4 g) was split in the usual manner to give, after crystallization of the crude acid from ether, 20.3 g of [S-(E)]-3-[2,2-bis(3-fluorophenyl)cyclopropyl]-2-propenoic acid, mp 128°–129° C.; $[\alpha]_D^{25}+224.6°$ (c, 1.0, MeOH).

Anal. Calculated for $C_{18}H_{14}F_2O_2$: C, 71.99; H, 4.70; F, 12.65. Found: C, 72.11; H, 4.67; F, 12.57.

EXAMPLE 98

[R,S-(E)]-3-[2,2-bis(3-Fluorophenyl)-1-methylcyclopropyl]-2-propenoic acid

As in Example 92, 2,2-bis(3-fluorophenyl)-1-methylcyclopropanecarboxaldehyde (22.7 g) was reacted with (carbomethoxymethylene)triphenylphosphorane (28.6 g) in methanol for 45 minutes at 55° C. The usual work up afforded 28 g of crude [R,S-(E)]-[2,2-bis(3-fluorophenyl)-1-methylcyclopropyl]-2-propenoic acid methyl ester. The ester was then saponified in a mixture of methanol (160 mL) and 2N sodium hydroxide solution over 1.25 hours at reflux. In the usual way, the methanol was removed in vacuo and replaced with water (100 mL). However, during the extraction of the basic solution with dichloromethane, the sodium salt of the racemic (E)-acid precipitated from the aqueous layer. After the salt was collected by filtration, the filtrate was acidified and extracted with dichloromethane to give 3.5 g of mixture of (E)- and (Z)-acids. Crystallization of this material from ether-hexane furnished 1.4 g of the desired (E)-isomer [R,S-(E)]-3-[2,2-bis(3-fluorophenyl)-1-methylcyclopropyl]-2-propenoic acid, mp 176°-179° C. The remaining material in the mother liquor was essentially at 1:1 mixture of the (E)- and (Z)-acids.

The sodium salt from above (25 g) was slurried in 1N hydrochloric acid (250 mL) for 15 minutes and the resulting mixture was extracted with dichloromethane (4×200 mL). The organic extracts were washed with dilute hydrochloric acid, then were combined, dried (MgSO4) and evaporated to furnish 22.2 g of [R,S-(E)]-3-[2,2-bis(3-fluorophenyl)-1-methylcyclopropyl]-2-propenoic acid. A sample was crystallized from ether-hexane to give the purified acid, mp 177°-179° C.

Anal. Calculated for $C_{19}H_{16}F_2O_2$: C, 72.60; H, 5.13; F, 12.09; Found: C, 72.84; H, 5.38; F, 12.35.

EXAMPLE 99

[R-(E)]-3-[2,2-bis(3-Fluorophenyl)-1-methylcyclopropyl]-2-propenoic acid and
[S-(E)]-3-[2,2-bis(3-fluorophenyl)-1-methylcyclopropyl]-2-propenoic acid Cinchonidine (8.9 g) was added to a hot solution of racemic (E)-3-[2,2-bis(3-fluorophenyl)-1-methylcyclopropyl]-2-propenoic acid (9.5 g) in methanol and the mixture was left at room temperature for 2 hours. The deposited salt (7.4 g) was recrystallized from methanol (2×) to yield 3.3 g of [S-(E)]-3-[2,2-bis(3-fluorophenyl)-1-methylcyclopropyl]-2-propenoic acid cinchonidine salt, mp 174°-176° C.

The original mother liquor was concentrated to 50 mL and cooled to room temperature. The resulting solid was collected by filtration and recrystallized from methanol to give 2.4 g of [R-(E)]-3-[2,2-bis(3-fluorophenyl)-1-methylcyclopropyl]-2-propenoic acid cinchonidine salt, mp 209°-211° C.

The (S)-acid cinchonidine salt (3.3 g) was converted to the acid in the usual manner to furnish 1.6 g of [S-(E)]-3-[2,2-bis(3-fluorophenyl)-1-methylcyclopropyl]-2-propenoic acid. Crystallization from ether-hexane afforded the analytical sample, mp 125°-126.5° C.; $[\alpha]_D^{25} -28.9°$ (c, 1.0, MeOH)

Anal. Calculated for $C_{19}H_{16}F_2O_2$: C, 72.60; H, 5.13; F, 12.09. Found: C, 72.65; H, 5.15; F, 72.65.

The (R)-acid cinchonidine salt (2.4 g) was converted to the acid in the usual manner to furnish 1.2 g of [R-(E)]-3-[2,2-bis(3-fluorophenyl)-1-methylcyclopropyl]-2-propenoic acid. Crystallization from ether-hexane provided the analytical sample, mp 125°-126.5° C.; $[\alpha]_D^{25} +29.5°$ (c, 1.0, MeOH)

Anal. Calculated for $C_{19}H_{16}F_2O_2$: C, 72.60; H, 5.13; F. 12.09. Found: C, 72.07; H, 5.30; F, 11.80.

EXAMPLE 100

[R,S-(E)]-3-[2,2-bis(4-Fluorophenyl)cyclopropyl]-2-propenoic acid and
[R,S-(Z)]-3-[2,2-bis(4-fluorophenyl)cyclopropyl]-2-propenoic acid As in Example 92, 2,2-bis(4-fluorophenyl)cyclopropanecarboxaldehyde (44.6 g) was reacted with (carbethoxymethylene)triphenylphosphorane (63 g) in ethanol (350 mL) over 1.25 hours at ambient temperature. The usual work up furnished a mixture of racemic (E)- and (Z)-esters (58 g) that was separated by HPLC (hexane-dichloromethane; 2:1) to yield 18 g of [R,S-(Z)]-3-[2,2-bis(4-fluorophenyl)cyclopropyl]-2-propenoic acid ethyl ester and 33 g of [R,S-(E)]-3-[2,2-bis(4-fluorophenyl)cyclopropyl]-2-propenoic acid ethyl ester as oils.

The racemic (Z)-ethyl ester, [R,S-(Z)]-3-[2,2-bis(4-fluorophenyl)cyclopropyl]-2-propenoic acid ethyl ester (9 g) was saponified as in previous examples in a mixture of methanol (60 mL) and 10N sodium hydroxide solution (7 mL) at 48° C. over 5 hours. The usual work up gave 15 g of crude acid that was crystallized from ether-hexane to afford 8.8 g of [R,S-(Z)]-3-[2,2-bis(4-fluorophenyl)cyclopropyl]-2-propenoic acid, mp 107°-108° C.

Anal. Calculated for $C_{18}H_{14}F_2O_2$: C, 71.99; H, 4.70; F, 12.65. Found: C, 71.85; H, 4.74; F, 12.62.

The racemic (E)-ethyl ester (33 g) was saponified as before in a mixture of methanol (100 mL) and 5N sodium hydroxide solution (26 mL) at reflux for 45 minutes. The usual work up gave 30 g of [R,S-(E)]-3-[2,2-bis(4-fluorophenyl)cyclopropyl]-2-propenoic acid. Crystallization of a portion from ethyl acetate-hexane afforded the analytical specimen, mp 166°-167.5° C.

Anal. Calculated for $C_{18}H_{14}F_2O_2$: C, 71.99; H, 4.70; F, 12.65. Found: C, 71.86; H, 4.78; F, 12.48.

EXAMPLE 101

[R-(E)]-3-[2,2-bis(4-Fluorophenyl)cyclopropyl]-2-propenoic acid and
[S-(E)]-3-[2,2-bis(4-fluorophenyl)cyclopropyl]-2-propenoic acid A solution of [R,S-(E)]-3-[2,2-bis(4-fluorophenyl)cyclopropyl]-2-propenoic acid (18 g) in 2-propanol (200 mL) at 75° C. was treated with cinchonidine (17.4 g) and the mixture was left at room temperature for 3 hours. The crystalline material was recovered by filtration to yield 16.1 g of partially resolved salt, mp 203°-205° C., which was recrystallized from 2-propanol (170 mL) to afford 14.25 g of [S-(E)]-3-[2,2-bis(4-fluorophenyl)cyclopropyl]-2-propenoic acid cinchonidine salt, mp 206°-207° C.

Evaporation of the original mother liquors gave an oil that was distributed between dichloromethane and 1N hydrochloric acid in the usual manner to furnish 10.6 g of partially resolved (+)-acid. A solution of this acid (10.6 g) in 2-propanol (300 mL) was treated with (−)-alpha-methyl-p-nitrobenzylamine (6 g) and the mixture was kept at ambient temperature for 5 hours. The crystalline material was recovered by filtration to give 13.5 g of a salt, mp 178°-179° C., that was recrystallized from the same solvent to yield 11.7 g of [R-(E)]-3-[2,2-bis(4-fluorophenyl)-2-propenoic acid (−)-alpha-methyl-p-nitrobenzylamine salt, mp 181°–182° C.

The (S)-acid cinchonidine salt (14.25 g) was split in the usual manner and the recovered acid was crystallized from ether-hexane to furnish 6.7 g of [S-(E)]-3-[2,2-bis(4-fluorophenyl)cyclopropyl]-2-propenoic acid, mp 122°–123° C.; $[\alpha]_D^{25} -206.4°$ (c, 1.0, MeOH)

Anal. Calculated for $C_{18}H_{14}F_2O_2$: C, 71.99; H, 4.70; F, 12.65. Found: C, 71.82; H, 4.69; F, 12.74.

The (R)-acid (−)-alpha-methyl-p-nitrobenzylamine salt (11.7 g) was split in the usual way and the recovered acid was crystallized from ether-hexane to furnish 7.1 g of [R-(E)]-3-[2,2-bis(r-fluorophenyl)cyclopropyl]-2-propenoic acid, mp 121.5°–123° C.; $[\alpha]_D^{25}+210.2°$ (c, 1.0, MeOH)

Anal. Calculated for $C_{19}H_{14}F_2O_2$: C, 71.99; H, 4.70; F, 12.65. Found: C, 72.02; H, 4.81; F, 12.38.

EXAMPLE 102

[R,S-(E)]-3-[2,2-bis(4-Fluorophenyl)-1-methylcyclopropyl]-2-propenoic acid

As in Example 92, 2,2-bis(4-fluorophenyl)-1-methylcyclopropanecarboxaldehyde (21.6 g) was reacted with (carbethoxymethylene)triphenylphosphorane (31 g) in methanol (100 mL) at 50° C. for 5 hours. A 2N solution of sodium hydroxide (200 mL) was added and the mixture was maintained at 50° C. for 3 hours. After the methanol was removed by filtration, the concentrate was diluted with water (200 mL) and the precipitated triphenylphosphine oxide was filtered off. The basic filtrate was extracted with dichloromethane (3×200 mL), then was acidified with concentrated hydrochloric acid (25 mL) and extracted with dichloromethane (5×200 mL). The organic extracts that contained the acidic material were combined, dried (MgSO$_4$) and evaporated. Trituration of the residue with hexane afforded 21.5 g of [R,S-(E)]-3-[2,2-bis(4-fluorophenyl)-1-methylcyclopropyl]-2-propenoic acid, mp 196°–197° C. Crystallization of a portion from ether-hexane provided the analytical sample, mp 197°–198° C.

Anal. Calculated for $C_{19}H_{16}F_2O_2$: C, 72.60; H, 5.13; F, 12.09. Found: C, 72.31; H, 5.08; F, 12.17.

EXAMPLE 103

[R-(E)]-3-[2,2-bis(4-Fluorophenyl)-1-methylcyclopropyl]-2-propenoic acid and
[S-(E)-3-]2,2-bis(4-fluorophenyl)-1-methylcyclopropyl]-2-propenoic acid Cinchonidine (16.5 g) was added to a heated solution of [R,S-(E)]-3-[2,2-bis(4-fluorophenyl)-1-methylcyclopropyl]-2-propenoic acid (17.5 g) in 2-propanol (150 mL) and the mixture was left at ambient temperature for 4 hours. The solids were recovered by filtration to give 16.2 g of partially resolved salt, mp 187°–189° C., which was recrystallized from the same solvent (120 mL) to furnish 14 g of [S-(E)]-3-[2,2-bis(4-fluorophenyl)-1-methylcyclopropyl]-2-propenoic acid cinchonidine salt, mp 188°–189° C.

Evaporation of the original mother liquor yielded a crude salt that was split in the usual manner to give 9.5 g of impure (+)-acid. This material was dissolved in 2-propanol (300 mL) containing (−)-alpha-methyl-p-nitrobenzylamine (5 g) and, after 2 hours at room temperature, the mixture was filtered to yield 12.5 g of a crystalline salt. Recrystallization of the solid from 2-propanol (300 mL) afforded 10.9 g of [R-(E)]-3-[2,2-bis(4-fluorophenyl)-1-methylcyclopropyl]-2-propenoic acid (−)-alpha-methyl-p-nitrobenzylamine salt.

The (S)-acid cinchonidine salt from above (14.0 g) was combined with an additional amount of the same compound (1.7 g) and was split in the usual manner to give [S-(E)]-3-[2,2-bis(4-fluorophenyl)-1-methylcyclopropyl]-2-propenoic acid. Trituration of the material with hot hexane furnished 7.3 g of the acid, mp 179.5°–180.5° C.; $[\alpha]_D^{25}-37.7°$ (c, 1.0, MeOH).

Anal. Calculated for $C_{19}H_{16}F_2O_2$: C, 72.60; H, 5.13; F, 12.09. Found: C, 72.66; H, 5.13; F, 12.17.

The (R)-acid (−)-alpha-methyl-p-nitrobenzylamine salt from above (10.6 g) was split in the usual manner to give [R-(E)]-3-[2,2-bis(4-fluorophenyl)-1-methylcyclopropyl]-2-propenoic acid. Trituration of the material with hot hexane afforded 6.5 g of the acid, mp 179.5°–180.5° C.; $[\alpha]_D^{25}+38.1°$ (c, 1.0, MeOH).

Anal. Calculated for $C_{19}H_{16}F_2O_2$: C, 72.60; H, 5.13; F, 12.09. Found: C, 72.66; H, 5.07; F, 12.04.

EXAMPLE 104

[R,S-(E)]-3-[2,2-bis(3-Methoxyphenyl)cyclopropyl]-2-propenoic acid

A mixture of 2,2-bis(3-methoxyphenyl)cyclopropanecarboxaldehyde (79.1 g), malonic acid (30 g) and piperidine (1 mL) in pyridine (50 mL) was heated at reflux temperature until the evolution of carbon dioxide subsided (1.5 hours). After the solvents were removed under reduced pressure, the residue was dissolved in dichloromethane (300 mL) and washed with 1N hydrochloric acid solution (200 mL) and with water (200 mL). The aqueous layers were extracted with dichloromethane (2×100 mL) and then the dried (MgSO$_4$) organic layers were evaporated to yield 75 g of crude acid as a reddish orange solid. Trituration of the crude with two portions of either (1×100 mL; 1×50 mL) afforded 61.6 g of [R,S-(E)]-3-[2,2-bis(3-methoxyphenyl)cyclopropyl]-2-propenoic acid, mp 126°–128° C. The analytical sample, mp 127.5°–128.5° C., was obtained by crystallization from ether-hexane.

Anal. Calculated for $C_{20}H_{20}O_2$: C, 74.06; H, 6.21. Found: C, 74.14; H, 6.31.

EXAMPLE 105

[R-(E)]-3-[2,2-bis(3-Methoxyphenyl)cyclopropyl]-2-propenoic acid and
[S-(E)]-3-[2,2-bis(3-methoxyphenyl)cyclopropyl]-2-propenoic acid Cinchonidine (42 g) was added to a heated solution of [R,S-(E)]-3-[2,2-bis(3-methoxyphenyl)cyclopropyl]-2-propenoic acid (57.75 g) in methanol (300 mL) and the mixture was left at room temperature for 5 hours. The crystalline solid that had formed was filtered and washed with cold methanol to give 37.5 g of the partially resolved salt, mp 177°–178° C. Recrystallization of the salt from methanol (150 mL) furnished 33.6 g of [S-(E)]-3-[2,2-bis(3-methoxyphenyl)cyclopropyl]-2-propenoic acid cinchonidine salt, mp 178°–179° C.

The original mother liquors were evaporated and the acidic component was isolated in the usual manner to yield 33 g of the impure partially resolved (+)-acid. The material freed from a polar impurity by filtration through a plug of silica gel in a dichloromethane-hexane-ether (1:1:2) mixture and then was crystallized from ethyl acetate to recover 12.6 g of the racemic acid [R,S-(E)]-3-[2,2-bis(3-methoxyphenyl)cyclopropyl]-2-propenoic acid. Evaporation of the mother liquor gave 16.1 g of residual material which was treated with (—)-alpha-methyl-p-nitrobenzylamine (8 g) in 2-propanol (200 mL). The crystalline solid that formed was recrystallized twice from 2-propanol to afford 17.5 g of [R-(E)]-3-[2,2-bis(3-methoxyphenyl)cyclopropyl]-2-propenoic acid (—)-alpha-methyl-p-nitrobenzylamine salt, mp 178°–179° C.

The (S)-acid cinchonidine salt from above (33.6 g) was split in the normal manner to give 17.5 g of [S-(E)]-3-[2,2-bis(3-methoxyphenyl)cyclopropyl]-2-propenoic acid. A portion (13 g) was crystallized from ether-hexane to furnish 11.1 g of [S-(E)]-3-[2,2-bis(3-methoxyphenyl)cyclopropyl]-2-propenoic acid, mp 98.5°–99.5° C. Recrystallization from ether-hexane afforded the analytical sample, mp 100°–101° C.; $[\alpha]_D^{25}$ —225° (c, 1.0, MeOH).

Anal. Calculated for $C_{20}H_{20}O_4$: C, 74.06; H, 6.21. Found: C, 74.26; H, 6.37.

The (R)-acid (—)-alpha-methyl-p-nitrobenzylamine salt (17.5 g) was split in the usual fashion to give, after crystallization of the crude acid from ether-hexane, 9.5 g of [R-(E)]-3-[2,2-bis(3-methoxyphenyl)cyclopropyl]-2-propenoic acid, mp 99°–100° C. Recrystallization of a sample from the same solvents gave the analytical specimen, mp 100°–101° C.; $[\alpha]_D^{25}$ +227° (c, 1.0, MeOH)

Anal. Calculated for $C_{20}H_{20}O_4$: C, 74.06; H, 6.21. Found: C, 73.87; H, 6.05.

EXAMPLE 106

[1(R,S),2(R,S)-(Z)]-3-[[2-(3-Methoxyphenyl)-2-phenyl]cyclopropyl]-2-propenoic acid, [1(R,S),2(S,R)-(Z)]-3-[[2-(3-methoxyphenyl)-2-phenyl]cyclopropyl]-2-propenoic acid,[1(R,S),2(R,S)-(E)]-3-[[2-(3-methoxyphenyl)-2-phenyl)cyclopropyl]-2-propenoic acid, and [1(R,S),2(S,R)-(E)]-3-[[2-(3-methoxyphenyl)-2-phenyl]-cyclopropyl]-2-propenoic acid As in Example 92, the mixture (~1:1) of [1(R,S),2(R,S)]-2-(3-methoxyphenyl)-2-phenylcyclopropanecarboxaldehyde and [1(R,S),2(S,R)]-2-(3-methoxyphenyl)-2-phenylcyclopropanecarboxaldehyde (75.6 g) was reacted with (carbomethoxymethylene)triphenylphosphorane (107 g) in methanol (400 mL) for 1 hour at room temperature. The usual work up furnished a mixture of the four possible racemic esters which were separated by a series of HPLCs as described below.

A preliminary gross separation of the two less polar (Z)-esters (35.4 g) from the (E)-esters (49.7 g) was achieved by using an ether-hexane (1:9) solvent mixture.

The (Z)-isomers were further resolved by HPLC (etherhexane; 1:12; 3 recycles) to yield 15.1 g of the faster moving [1(R,S),2(R,S)-(Z)]-3-[[2-(3-methoxyphenyl)-2-phenyl]cyclopropyl]-2-propenoic acid methyl ester and 15.8 g of [1(R,S),2(S,R)-(Z)]-3-[[2-(3-methoxyphenyl)-2-phenyl]cyclopropyl]-2-propenoic acid methyl ester, both as oils.

The mixture of (E)-isomers were separated in a similar manner (ether-hexane; 3:17, 2 recycles) to furnish 23.3 g of the less polar [1(R,S),2(R,S)-(E)]-3-[[(2-(3-methoxyphenyl)-2-phenyl]cyclopropyl]-2-propenoic acid methyl ester and 18.1 g of [1(R,S),2(S,R)-(E)]-3-[[2-(3-methoxyphenyl)-2-phenyl]cyclopropyl]-2-propenoic acid methyl ester, both as oils.

Saponification of the less polar (Z)-ester [1(R,S),2(R,S)-(Z)]-3-[[2-(3-methoxyphenyl)-2-phenyl]cyclopropyl]-2-propenoic acid methyl ester (14.3 g) was done in a mixture of methanol (100 ml) and 4N potassium hydroxide solution (20 mL) at reflux for 35 minutes. The usual work up furnished, after crystallization of the crude product from 2-propanol-hexane, 8.9 g of [1(R,S),2(R,S)-(Z)]-3-[[2-(3-methoxyphenyl)-2-phenyl]cyclopropyl]-2-propenoic acid, mp 138°–139° C. Recrystallization from the same solvents provided the analytical sample, mp 138.5°–139.5° C.

Anal. Calculated for $C_{19}H_{18}O_3$: C, 77.53; H, 6.16. Found: C, 77.76; H, 6.11.

In the same way, the more polar (Z)-ester [1(R,S),2(S,R)-(Z)]-3-[[2-(3-methoxyphenyl)-2-phenyl]cyclopropyl]-2-propenoic acid methyl ester (14.6 g) was saponified in a mixture of methanol (100 ml) and 4N potassium hydroxide solution (20 mL) at reflux for 25 minutes. The usual work up, after crystallization of the crude product from 2-propanol-hexane, gave 10 g of [1(R,S),2(S,R)-(Z)]-3-[[2-(3-methoxyphenyl)-2-phenyl]cyclopropyl]-2-propenoic acid, mp 114°–115° C. Recrystallization of a sample from the same solvents afforded the analytical specimen, mp 114°–115° C.

Anal. Calculated for $C_{19}H_{18}O_3$: C, 77.53; H, 6.16. Found: C, 77.81; H, 6.15.

Saponification of the less polar (E)-ester (22 g) was done in a mixture of methanol (125 ml) and 4N potassium hydroxide solution (30 mL) at reflux for 30 minutes. The usual work up furnished, after crystallization of the crude product from 2-propanol-hexane, 14.1 g of [1(R,S),2(R,S)-(E)]-3-[[2-(3-methoxyphenyl)-2-phenyl]cyclopropyl]-2-propenoic acid, mp 149°–151° C. Recrystallization from 2-propanol yielded the analytical sample, mp 150°–151.5° C.

Anal. Calculated for $C_{19}H_{18}O_3$: C, 77.53; H, 6.16. Found: C, 77.38; H, 6.05.

In the same manner, the more polar (E)-ester (18 g) was saponified in a mixture of methanol (100 ml) and 4N potassium hydroxide solution (25 mL) at reflux for 30 minutes. The usual work up, after crystallization of the crude product from 2-propanol-hexane, furnished 11.5 g of [1(R,S),2(S,R)-(E)]-3-[[2-(3-methoxyphenyl)-2-phenyl]cyclopropyl]-2-propenoic acid, mp 130°–132° C. A portion was recrystallized from 2-propanol to afford the anaytical sample, mp 132.5°–133.5° C.

Anal. Calculated for $C_{19}H_{18}O_3$: C, 77.53; H, 6.16. Found: C, 77.11; H, 6.05.

EXAMPLE 107

[R,S-(E)]-3-[2,2-bis[3-(Trifluoromethyl)phenyl]cyclopropyl]-2-propenoic acid

As in Example 104, 2,2-bis[3-(trifluoromethyl)phenyl]cyclopropanecarboxaldehyde (32.5 g) was reacted with malonic acid (9.6 g) in the presence of piperidine (0.4 mL) in pyridine (20 mL) at reflux for 2.5 hours. The usual work up furnished 29 g of crude acid which was crystallized from hexane to give 17.7 g of [R,S-(E)]-3-[2,2-bis[3-(trifluoromethyl)phenyl]cyclopropyl]-2-propenoic acid, mp 119°–121° C. A sample was recrystallized from hexane to yield to analytical specimen, mp 122°–124° C.

Anal. Calculated for $C_{20}H_{14}F_6O_2$: C, 60.00; H, 3.53; F, 28.48. Found: C, 60.22; H, 3.65 F. 28.77.

The mother liquors were purified by HPLC (dichloromethane-hexane; 1:1) to provide an additional 5 g of the (E)-acid as well as 0.6 g of the isomeric ]R,S-(Z)]-3-[2,2-bis[3-(trifluoromethyl)phenyl]cyclopropyl]-2-propenoic acid. The (Z)-acid was crystallized from dichloromethanehexane to yield the analytical sample, mp 147°–148° C.

Anal. Calculated for $C_{20}H_{14}F_6O_2$: C, 60.00; H, 3.53; F, 28.48. Found: C, 59.87; H, 3.56 F. 28.22.

EXAMPLE 108

(R,S)-2,2-Diphenylcyclopropanepropanoic acid

A mixture of [R,S-(E)]-3-(2,2-diphenylcyclopropyl)-2-propenoic acid ethyl ester (10 g) and Raney Ni (2 g) in ethanol (100 mL) was hydrogenated at room temperature and atmospheric pressure. After the hydrogen uptake had stopped, the catalyst was removed by filtration and the filtrate was evaporated to provide 9.95 g of the saturated ester. A solution of the hydrogenation product (9.75 g) in methanol (65 mL) containing 4N potassium hydroxide (15 mL) was heated at reflux for 0.75 hour. After the reaction was diluted with water (65 mL), the methanol was removed in vacuo and the concentrate was added to a mixture of ice and 1N hydrochloric acid (100 mL). The resulting solid was filtered off, washed with water and dried to yield 8.45 g of (R,S)-diphenylcyclopropanepropanoic acid, mp 84.5°–87° C. The analytical sample, mp 87.5°–88.5° C., was obtained from ether-hexane.

Anal. Calculated for $C_{18}H_{18}O_2$: C, 81.17; H, 6.81. Found: C, 81.39; H, 6.59.

EXAMPLE 109

(R)-Diphenylcyclopropanepropanoic acid

A mixture of the levorotary [R-(Z)]-3-(2,2-diphenylcyclopropyl)-2-propenoic acid (0.264 g) and Raney Ni (0.05 g) in ethanol (10 mL) was hydrogenated at room temperature and atmospheric pressure. After the uptake of hydrogen had stopped, the catalyst was filtered off and the solvent removed in vacuo to provide 0.260 g of (R)-diphenylcyclopropanepropanoic acid as an oil, $[\alpha]_D^{25} +138°$ (c, 1.0, MeOH).

EXAMPLE 110

(S)-Diphenylcyclopropanepropanoic acid

A mixture of the levorotary [S-(E)-3-(2,2-diphenylcyclopropyl)-2-propenoic acid (8.4 g) and Raney Ni (2 g) in ethanol (100 mL) was hydrogenated as in the previous example, to give after work up, 8.4 g of (S)-diphenylcyclopropanepropanoic acid as an oil, $[\alpha]_D^{25} -137°$ (c, 1.0, MeOH).

EXAMPLE 111

[R,S-(E)]-3-(2,2-Diphenylcyclopropyl)-2-propenoic acid 4-nitrophenyl ester

A solution of [R,S-(E)]-3-(2,2-diphenylcyclopropyl)-2-propenoic acid (10.25 g) and 4-nitrophenyl (6.5 g) in dichloromethane (100 mL), stirred at 0°–5° C. in an ice-water bath, was treated with 1,3-dicyclohexylcarbodiimide (8.0 g). The mixture was stirred at 0°–5° C. for 10 minutes, then at room temperature for 1 hour. After the precipitated dicyclohexylurea was filtered off, the concentrated filtrate was passed through a short column of silica gel (~75 g) made up in dichloromethane-hexane (3:2). The appropriate fractions were combined and evaporated to give 15.8 g of crude ester. Crystallization of the material from toluene-hexane furnished 12.15 g of [R,S-(E)]-3-(2,2-diphenylcyclopropyl)-2-propenoic acid 4-nitrophenyl ester, mp 146°–147° C.

EXAMPLE 112

[R-(E)]-3-(2,2-Diphenylcyclopropyl)-2-propenoic acid 4-nitrophenyl ester

As in Example 111, [R-(E)]-3-(2,2-diphenylcyclopropyl)-2-propenoic acid (5.0 g) and 4-nitrophenol (3.17 g) in dichloromethane (50 mL) was treated with 1,3-dicyclohexylcarbodiimide (3.9 g) and the mixture was stirred at room temperature for 1 hour. The usual work up gave 7 g of [R-(E)]-3-(2,2-diphenylcyclopropyl)-2-propenoic acid 4-nitrophenyl ester as an oil. This material was used without further purification in subsequent reactions.

EXAMPLE 113

[S-(E)]-3-(2,2-Diphenylcyclopropyl)-2-propenoic acid 4-nitrophenyl ester

As in Example 111, [S-(E)]-3-(2,2-diphenylcyclopropyl)-2-propenoic acid (6.0 g) and 4-nitrophenol (3.74 g) in dichloromethane (60 mL) was treated with 1,3-dicyclohexylcarbodiimide (4.68 g) and the mixture was stirred at room temperature for 1 hour. The usual work up afforded 9 g of crude ester that was purified by HPLC (dichloromethanehexane; 1:1) to give 6.45 g of [S-(E)]-3-(2,2-diphenylcyclopropyl)-2-propenoic acid 4-nitrophenyl ester as an oil.

EXAMPLE 114

[R,S-(E)]-3-[2,2-bis(3-Fluorophenyl)cyclopropyl]-2-propenoic acid 4-nitrophenyl ester As in Example 111, [R,S-(E)]-3-[2,2-bis(3-fluorophenyl)cyclopropyl]-2-propenoic acid (3.5 g) and 4-nitrophenol (1.73 g) in dichloromethane (50 mL) was treated with 1,3-dicyclohexylcarbodiimide (2.33 g) and the mixture was stirred at room temperature for 45 minutes. The usual work up provided 4.2 g of [R,S-(E)]-3-[2,2-bis(3-fluorophenyl)cyclopropyl]-2-propenoic acid 4-nitrophenyl ester, which was crystallized from ether to give 3.6 g of essentially pure material.

EXAMPLE 115

[R-(E)]-3-[2,2-bis(3-Fluorophenyl)cyclopropyl]-2-propenoic acid 4-nitrophenyl ester As in Example 111, [R-(E)]-3-[2,2-bis(3-fluorophenyl)cyclopropyl]-2-propenoic acid (1.76 g) and 4-nitrophenol (0.9 g) in dichloromethane (25 mL) was treated with 1,3-dicyclohexylcarbodiimide (1.21 g) and the mixture was stirred at 0°–5° C. for 10 minute and then at room temperature for 1 hour. The usual work up afforded 2.5 g of [R-(E)]-3-[2,2-bis(3-fluorophenyl)cyclopropyl]-2-propenoic acid 4-nitrophenyl ester as an oil.

EXAMPLE 116

[S-(E)]-3-[2,2-bis(3-Fluorophenyl)cyclopropyl]-2-propenoic acid 4-nitrophenyl ester As in Example 111, [R-(E)]-3-[2,2-bis(3-fluorophenyl)cyclopropyl]-2-propenoic acid (2.1 g) and 4-nitrophenol (1.07 g) in dichloromethane (30 mL) was treated with 1,3-dicyclohexylcarbodiimide (1.45 g) and the mixture was stirred at 0°–5° C. for 1 hour and then at room temperature for 17 hours. The usual work up furnished 2.8 g of [S-(E)]-3-[2,2-bis(3-fluorophenyl)cyclopropyl]-2-propenoic acid 4-nitrophenyl ester as an oil.

EXAMPLE 117

[R-(E)]-3-[2,2-bis(3-Fluorophenyl)-1-methylcyclopropyl]-2-propenoic acid 4-nitrophenyl ester As in Example 111, [R-(E)]-3-[2,2-bis(3-fluorophenyl)-1-methylcyclopropyl]-2-propenoic acid (3.75 g) and 4-nitrophenol (1.84 g) in dichloromethane (40 mL) was treated with 1,3-dicyclohexylcarbodiimide (1.21 g) and the mixture was stirred at 0°–5° C. for 1 hour and then at room temperature for 18 hours. The usual work up provided 4.5 g of [R-(E)]-3-[2,2-bis(3-fluorophenyl)-1-methylcyclopropyl]-2-propenoic acid 4-nitrophenyl ester as an oil.

EXAMPLE 118

[S-(E)]-3-[2,2-bis(3-Fluorophenyl)-1-methylcyclopropyl]-2-propenoic acid 4-nitrophenyl ester As in Example 111, [S-(E)]-3-[2,2-bis(3-fluorophenyl)-1-methylcyclopropyl]-2-propenoic acid (3.0 g) and 4-nitrophenol (1.46 g) in dichloromethane (30 mL) was treated with 1,3-dicyclohexylcarbodiimide (2.06 g) and the mixture was stirred at 0°–5° C. for 1 hour and then at room temperature for 18 hours. The usual work up furnished 3.6 g of [S-(E)]-3-[2,2-bis(3-fluorophenyl)-1-methylcyclopropyl]-2-propenoic acid 4-nitrophenyl ester as an oil.

EXAMPLE 119

[R,S-(E)]-3-[2,2-bis(4-Fluorophenyl)cyclopropyl]-2-propenoic acid 4-nitrophenyl ester As in Example 111, [R,S-(E)]-3-[2,2-bis(4-fluorophenyl)cyclopropyl]-2-propenoic acid (1.8 g) and 4-nitrophenol (0.92 g) in dichloromethane (25 mL) was treated with 1,3-dicyclohexylcarbodiimide (2.33 g) and the reaction was stirred at 0°–5° C. for 1 hour. The usual work up provided 2.4 g of [R,S-(E)]-3-[2,2-bis(4-fluorophenyl)cyclopropyl]-2-propenoic acid 4-nitrophenyl ester.

EXAMPLE 120

[R-(E)]-3-[2,2-bis(4-Fluorophenyl)cyclopropyl]-2-propenoic acid 4-nitrophenyl ester As in Example 111, [R-(E)]-3-[2,2-bis(4-fluorophenyl)cyclopropyl]-2-propenoic acid (3.0 g) and 4-nitrophenol (1.53 g) in dichloromethane (40 mL) was treated with 1,3-dicyclohexylcarbodiimide (2.06 g) and the mixture was stirred at 0°–5° C. for 1 hour. The usual work up provided 4 g of [R-(E)]-3-[2,2-bis(4-fluorophenyl)cyclopropyl]-2-propenoic acid 4-nitrophenyl ester as an oil.

EXAMPLE 121

[S-(E)]-3-[2,2-bis(4-Fluorophenyl)cyclopropyl]-2-propenoic acid 4-nitrophenyl ester As in Example 111, [S-(E)]-3-[2,2-bis(4-fluorophenyl)cyclopropyl]-2-propenoic acid (3.0 g) and 4-nitrophenol (1.53 g) in dichloromethane (40 mL) was treated with 1,3-dicyclohexylcarbodiimide (2.06 g) and the reaction was stirred at 0°–5° C. for 1 hour. The usual work up yielded 4 g of [S-(E)]-3-[2,2-bis(4-fluorophenyl)cyclopropyl]-2-propenoic acid 4-nitrophenyl ester as an oil.

EXAMPLE 122

[R,S-(E)]-[2,2-bis(4-Fluorophenyl)-1-methylcyclopropyl]-2-propenoic acid 4-nitrophenyl ester As in Example 111, (R,S)-(E)-[2,2-bis(4-fluorophenyl)-1-methylcyclopropyl]-2-propenoic acid (2.83 g) and 4-nitrophenyl (1.4 g) in dichloromethane (35 ml) was treated with 1,3-dicyclohexylcarbodiimide (1.86 g) and the reaction was stirred at 0°–5° C. for 1 hour. The usual work up provided 3.72 g of [R,S-(E)]-[2,2-bis(4-fluorophenyl)-1-methylcyclopropyl]-2-propenoic acid 4-nitrophenyl ester as an oil.

EXAMPLE 123

[R-(E)]-3-[2,2-bis(4-Fluorophenyl)-1-methylcyclopropyl]-2-propenoic acid 4-nitrophenyl ester As in Example 111, [R-(E)]-3-[2,2-bis(4-fluorophenyl)-1-methylcyclopropyl]-2-propenoic acid (2.83 g) and 4-nitrophenol (1.4 g) in dichloromethane (35 mL) was treated with 1,3-dicyclohexylcarbodiimide (1.86 g) and the reaction was stirred at 0°–5° C. for 1 hour. The usual work up gave 3.7 g of [R-(E)]-3-[2,2-bis(4-fluorophenyl)-1-methylcyclopropyl]-2-propenoic acid 4-nitrophenyl ester as an oil.

EXAMPLE 124

[S-(E)]-3-[2,2-bis(4-Fluorophenyl)-1-methylcyclopropyl]-2-propenoic acid 4-nitrophenyl ester As in the previous example, [S-(E)]-3-[2,2-bis(4-fluorophenyl)-1-methylcyclopropyl]-2-propenoic acid (2.83 g) and 4-nitrophenyl ester (1.4 g) in dichloromethane (35 mL) was treated with 1,3-dicyclohexylcarbodiimide (2.06 g) and the mixture was stirred at 0°–5° C. for 1 hour. The usual work up gave 3.72 g of [S-(E)]-3-[2,2-bis(4-fluorophenyl)-1-methylcyclopropyl]-2-propenoic acid 4-nitrophenyl ester as an oil.

EXAMPLE 125

[R,S-(E)]-3-[2,2-bis(3-Methoxyphenyl)cyclopropyl]-2-propenoic acid 4-nitrophenyl ester As in Example 111, [R,S-(E)]-3-[2,2-bis(3-methoxyphenyl)cyclopropyl]-2-propenoic acid (4.05 g) and 4-nitrophenol (2.1 g) in dichloromethane (25 mL) was treated with 1,3-dicyclohexylcarbodiimide (2.57 g) and the reaction was stirred at 30° C. for 1 hour. The usual work up provided 4.6 g of [R,S-(E)]-3-[2,2-bis(3-methoxyphenyl)cyclopropyl]-2-propenoic acid 4-nitrophenyl ester as an oil.

EXAMPLE 126

[R,S-(E)]-3-[2,2-bis(3-Methoxyphenyl)cyclopropyl]-2-propenoic acid 4-nitrophenyl ester As in Example 111, (R,S)-(E)-3-[2,2-bis(3-methoxyphenyl)cyclopropyl]-2-propenoic acid (4.05 g) and 4-nitrophenol (2.1 g) in dichloromethane (25 mL) was treated with 1,3-dicyclohexylcarbodiimide (2.57 g) and the reaction was stirred at 30° C. for 1 hour. The usual work up provided 4.6 g of [R,S-(E)]-3-[2,2-bis(3-methoxyphenyl)cyclopropyl]-2-propenoic acid 4-nitrophenyl ester as an oil.

EXAMPLE 127

[S-(E)]-3-[2,2-bis(3-Methoxyphenyl)cyclopropyl]-2-propenoic acid 4-nitrophenyl ester As in the previous examples, [S-(E)]-3-[2,2-bis(3-methoxyphenyl)cyclopropyl]-2-propenoic acid and 4-nitrophenol (2.18 g) in dichloromethane (35 mL) was treated with 1,3-dicyclohexylcarbodiimide (3.3 g) and the mixture was stirred at 30° C. for 1 hour. The usual work up provided 6.4 g of [S-(E)]-3-[2,2-bis(3-methoxyphenyl)cyclopropyl]-2-propenoic acid 4-nitrophenyl ester as an clear glass.

EXAMPLE 128

[1(R,S),2(R,S)-(E)]-3-[[2-(3-Methoxyphenyl)-2-phenyl]cyclopropyl]-2-propenoic acid 4-nitrophenyl ester As in Example 111, [1(R,S),2(R,S)-(E)]-3-[[2-(3-methoxyphenyl)-2-phenyl]cyclopropyl]-2-propenoic acid (1.5 g) and 4-nitrophenol (0.856 g) in dichloromethane (10 mL) was treated with 1,3-dicyclohexylcarbodiimide (1.05 g) and the reaction was stirred at 0°-5° C. for 1 hour and then at 25° C. for 16 hours. The usual work up yielded 1.6 g of [1(R,S),2(R,S)-(E)]-3-[[2-(3-methoxyphenyl)-2-phenyl]cyclopropyl]-2-propenoic acid 4-nitrophenyl ester as an oil.

EXAMPLE 129

[1(R,S),2(S,R)-(E)]-3-[[2-(3-Methoxyphenyl)-2-phenyl]cyclopropyl]-2-propenoic acid 4-nitrophenyl ester As in the previous example, [1(R,S),2(S,R)-(E)]-3-[[2-(3-methoxyphenyl)-2-phenyl]cyclopropyl]-2-propenoic acid (1.5 g) and 4-nitrophenol (0.856 g) in dichloromethane (10 mL) was treated with 1,3-dicyclohexylcarbodiimide (1.05 g) and the mixture was stirred at 0°-5° C. for 1 hour and then at 25° C. for 16 hours. The usual work up furnished 1.55 g of [1(R,S),2(S,R)-(E)]-3-[[2-(3-methoxyphenyl)-2-phenyl]cyclopropyl]-2-propenoic acid 4-nitrophenyl ester as a glass.

EXAMPLE 130

[R,S-(E)]-3-[2,2-bis[3-Trifluoromethyl)phenyl)cyclopropyl]-2-propencic acid 4-nitrophenyl ester As in Example 111, [R,S-(E)]-3-[2,2-bis[3-(trifluoromethyl)phenyl]cyclopropyl]-2-propenoic acid (2.0 g) and 4-nitrophenol (0.764 g) in dichloromethane (25 mL) was treated with 1,3-dicyclohexylcarbodiimide (1.032 g) and the mixture was stirred at 0°-5° C. for 10 minutes and then at room temperature for 1.5 hours. The usual work up gave 6.4 g of [R,S-(E)[-3-[2,2-bis[3-trifluoromethyl)phenyl)cyclopropyl]-2-propenoic acid 4-nitrophenyl ester as an oil.

EXAMPLE 131

[R,S-(Z)]-3-(2,2-Diphenylcyclopropyl)-2-propenoic acid 4-nitrophenyl ester

As in Example 111, [R,S-(Z)]-3-(2,2-diphenylcyclopropyl)-2-propenoic acid (11.25 g) and 4-nitrophenol (7.13 g) in dichloromethane (120 mL) was treated with 1,3-dicyclohexylcarbodiimide (8.8 g) and the mixture was stirred at 0°-5° C. for 10 minutes then at room temperature for 1 hour. After the usual work up, the crude product (16.8 g) was crystallized from toluene-hexane to give 13.65 g of [R,S-(Z)]-3-(2,2-diphenylcyclopropyl)-2-propenoic acid 4-nitrophenyl ester, mp 164°-165.5° C.

EXAMPLE 132

[R-(Z)]-3-(2,2-Diphenylcyclopropyl)-2-propenoic acid 4-nitrophenyl ester

As in Example 111, [R-(Z)]-3-(2,2-Diphenylcyclopropyl)-2-propenoic acid (6.0 g) and 4-nitrophenol (3.8 g) in dichloromethane (60 mL) was treated with 1,3-dicyclohexylcarbodiimide (4.68 g) and the mixture was stirred at 30° C. for 1 hour. The usual work up gave 8.7 g of crude product which was crystallized from 2-propanol to furnish 7.25 g of [R-(Z)]-3-(2,2-diphenylcyclopropyl)-2-propenoic acid 4-nitrophenyl ester, mp 88°-89° C.; $[\alpha]_D^{25}$ −347.9 (c, 1.0, MeOH).

Anal. Calculated for $C_{24}H_{19}NO_4$: C, 74.79; H, 4.97; N, 3.63. Found: C, 75.03; H, 5.18; N, 3.51.

EXAMPLE 133

[S-(Z)]-3-(2,2-Diphenylcyclopropyl)-2-propenoic acid 4-nitrophenyl ester

As in the previous sample, [S-(Z)]-3-(2,2-diphenylcyclopropyl)-2-propenoic acid (6.0 g) and 4-nitrophenol (3.8 g) in dichloromethane (60 mL) was treated with 1,3-dicyclohexylcarbodiimide (4.68 g) and the mixture was stirred at 30° C. for 1 hour. The usual work up afforded 7.5 g of crude product. The ester was crystallized from 2-propanol to give 6.5 g of [S-(Z)]-3-(2,2-diphenylcyclopropyl)-2-propenoic acid 4-nitrophenyl ester, mp 88°-89° C.; $[\alpha]_D^{25}$ +347.3° C. (c, 1.0, MeOH).

EXAMPLE 134

[R,S-(Z)]-3-[2,2-bis(3-Fluorophenyl)cyclopropyl]-2-propenoic acid 4-nitrophenyl ester As in Example 111, (R,S)-(Z)-3-[2,2-bis(3-fluorophenyl)cyclopropyl]-2-propenoic acid (2.1 g) and 4-nitrophenol (1.07 g) in dichloromethane (30 mL) was treated with 1,3-dicyclohexylcarbodiimide (1.45 g) and the mixture was stirred at 0°-5° C. for 1 hour and then at 25° C. for 16 hours. The usual work up yielded 3 g of [R,S-(Z)]-3-[2,2-bis(3-fluorophenyl)cyclopropyl]-2-propenoic acid 4-nitrophenyl ester as an oil. A portion was crystallized from ethyl acetate-hexane to give the ester, mp 162°-163° C.

EXAMPLE 135

[R,S-(Z)]-3-[2,2-bis(4-Fluorophenyl)cyclopropyl]-2-propenoic acid 4-nitrophenyl ester As in the previous example, [R,S-(Z)]-3-[2,2-bis(4-fluorophenyl)cyclopropyl]-2-propenoic acid (0.9 g) and 4-nitrophenol (0.4 g) in dichloromethane (12 mL) was treated with 1,3-dicyclohexylcarbodiimide (0.62 g) and the mixture was stirred at 0°-5° C. for 1 hour. The usual work up provided 1.3 g of [R,S-(Z)]-3-[2,2-bis(4-fluorophenyl)cyclopropyl]-2-propenoic acid 4-nitrophenyl ester as an oil.

EXAMPLE 136

[1(R,S),2(R,S)-(Z)-3-[[2-(3-Methoxyphenyl)-2-phenyl]cyclopropyl]-2-propenoic acid 4-nitrophenyl ester As in Example 111, [1-(R,S),2(R,S)-(Z)]-3-[[2-(3-methoxyphenyl)-2-phenyl]cyclopropyl]-2-propenoic acid (1.5 g) and 4-nitrophenol (0.856 g) in dichloromethane (10 mL) was treated with 1,3-dicyclohexylcarbodiimide (1.05 g) and the mixture was stirred at 0°-5° C. for 1 hour and then at 25° C. for 16 hours. The usual work up gave 1.4 g of [1(R,S),2(R,S)-(Z)]-3-[[2-(3-methoxyphenyl)-2-phenyl]cyclopropyl]-2-propenoic acid 4-nitrophenyl ester as an oil.

EXAMPLE 137

[1(R,S),2(S,R)-(Z)]-3-[[2-(3-Methoxyphenyl)-2-phenyl]-cyclopropyl]-2-propenoic acid 4-nitrophenyl ester As in the previous example, [1(R,S),2(S,R)-(Z)]-3-[[2-(3-methoxyphenyl)-2-phenyl]cyclopropyl]-2-propenoic acid (1.5 g) and 4-nitrophenol (0.856 g) in dichloromethane (10 mL) was treated with 1,3-dicyclohexylcarbodiimide (1.05 g) and the reaction was stirred at 0°–5° C. for 1 hour and then at 25° C. for 16 hours. The usual work up yielded 1.5 g of [1(R,S),2(S,R)-(Z)]-3-[[2-(3-methoxyphenyl)-2-phenyl]cyclopropyl]-2-propenoic acid 4-nitrophenyl ester as a glass.

EXAMPLE 138

(R,S)-2,2-Diphenylcyclopropanepropanoic acid 4-nitrophenyl ester

As in Example 111, (R,S)-2,2-diphenylcyclopropanepropanoic acid (7.6 g) and 4-nitrophenol (4.78 g) in dichloromethane (75 mL) was treated with 1,3-dicyclohexylcarbodiimide (5.88 g) and the mixture was stirred at 30° C. for 1.5 hours. The usual work up furnished 9.15 g of (R,S)-2,2-diphenylcyclopropanepropanoic acid 4-nitrophenyl ester.

EXAMPLE 139

(R)-2,2-Diphenylcyclopropanepropanoic acid 4-nitrophenyl ester

As in Example 111, (R)-2,2-diphenylcyclopropanepropanoic acid (6.1 g) and 4-nitrophenol (3,8 g) in dichloromethane (100 mL) was treated with 1,3-dicyclohexylcarbodiimide (4.7 g) and the mixture was stirred at 30° C. for 1 hour. The product obtained from the usual work up was crystallized from 2-propanol to yield 6.4 g of (R)-2,2-diphenylcyclopropanepropanoic acid 4-nitrophenyl ester, mp 77.5°–76.5° C.; $[\alpha]_D^{25}$ +93.7° (c, 1.0, MeOH)

Anal. Calculated for $C_{24}H_{21}NO_4$: C, 74.40; H, 5.46; N, 3.62. Found: C, 74.46; H, 5.54; N, 3.77.

EXAMPLE 140

(S)-2,2-Diphenylcyclopropanepropanoic acid 4-nitrophenyl ester

As in Example 111, (S)-2,2-diphenylcyclopropanepropanoic acid (6.38 g) and 4-nitrophenol (4 g) in dichloromethane (100 mL) was treated with 1,3-dicyclohexylcarbodiimide (4.95 g) and the mixture was stirred at 25° C. for 1 hour. The crude ester, isolated in the usual way, was crystallized from 2-propanol to give 4.8 g of (S)-2,2-diphenylcyclopropanepropanoic acid 4-nitrophenyl ester. The analytical sample was obtained from the same solvent, mp 76°–77° C.; $[\alpha]_D^{25}$ −93.53° (c, 1.0, MeOH).

Anal. Calculated for $C_{24}H_{21}NO_4$: C, 74.40; H, 5.46; N, 3.62. Found: C, 74.58; H, 5.55; N, 3.62.

EXAMPLE 141

[R,S-(E)]-3-(2,2-Diphenylcyclopropyl)-N-[4-(3-pyridinyl)butyl]-2-propenamide

A solution of [R,S-(E)]-3-(2,2-diphenylcyclopropyl)-2-propenoic acid 4-nitrophenyl ester (6.17 g) and 3-pyridinebutanamine (2.5 g) in tetrahydrofuran (50 mL) was stirred at room temperature for 2 hours. After the solvent was removed in vacuo, a solution of the residue in dichloromethane was washed with 0.5N sodium hydroxide solution (3×100 mL). The aqueous layers were backwashed with dichloromethane (2×50 mL), then the dried ($K_2CO_3$) organic extracts were evaporated. The resulting crude amide was purified by HPLC (ethyl acetate) and then was crystallized from ethyl acetate-hexane (2×) to yield 3.8 g of [R,S-(E)]-3-(2,2-diphenylcyclopropyl)-N-[4-(3-pyridinyl)butyl]-2-propenamide, mp 135.5°–136.5° C.

Anal. Calculated for $C_{27}H_{28}N_2O$: C, 81.78; H, 7.12; N, 7.06. Found: C, 81.61; H, 7.09; N, 7.04.

EXAMPLE 142

[R-(E)]-3-(2,2-Diphenylcyclopropyl)-N-[4-(3-pyridinyl)butyl]-2-propenamide

As in Example 141, a solution of [R-(E)]-3-(2,2-diphenylcyclopropyl)-2-propenoic acid 4-nitrophenyl ester (6.15 g) and 3-pyridinebutanamine (2.43 g) in tetrahydrofuran (50 mL) was stirred at room temperature for 2 hours. The usual work up provided 7.4 g of crude amide that was purified by HPLC (ethyl acetate-hexane-triethylamine; 45:5:1) to provide 3.8 g of [R-(E)]-3-(2,2-diphenylcyclopropyl)-N-[4-(3-pyridinyl)butyl]-2-propenamide as an oil, $[\alpha]_D^{25}$ +130.6° (c, 1.0, MeOH)

Anal. Calculated for $C_{27}H_{28}N_2O$: C, 81.78; H, 7.12; N, 7.06. Found: C, 81.62; H, 7.08; N, 6.76.

EXAMPLE 143

[S-(E)]-3-(2,2-Diphenylcyclopropyl)-N-[4-(3-pyridinyl)butyl]-2-propenamide

As in example 141, a solution of [S-(E)]-3-(2,2-diphenylcyclopropyl)-2-propenoic acid 4-nitrophenyl ester (7.2 g) and 3-pyridinebutanamine (2.85 g) in tetrahydrofuran (140 mL) was stirred at room temperature for 2 hours. After the usual work up, the product was purified by HPLC (ethyl acetate-hexane-triethylamine; 45:5:1) to give 5.1 g of [S-(E)]-3-(2,2-diphenyl-cyclopropyl)-N-[4-(3-pyridinyl)butyl]-2-propenamide as a colorless oil. $[\alpha]_D^{25}$ −129.8° (c, 1.0, MeOH).

Anal. Calculated for $C_{27}H_{28}N_2O$: C, 81.78; H, 7.12; N, 7.06. Found: C, 81.57; H, 7.17; N, 6.93.

EXAMPLE 144

[R,S-(E)]-3-[2,2-bis(3-Fluorophenyl)cyclopropyl]-N-[4-(3-pyridinyl)butyl]-2-propenamide As in Example 141, a solution of [R,S-(E)]-3-[2,2-bis(3-fluorophenyl)cyclopropyl]-2-propenoic acid 4-nitrophenyl ester (2.5 g) and 3-pyridinebutanamine (1.25 g) in tetrahydrofuran (15 mL) was stirred at room temperature for 75 minutes. The crude product was isolated in the usual manner and was purified by HPLC (ethyl acetate). The resulting material was crystallized from ethyl acetate (2×) to furnish 2.4 g of [R,S-(E)]-3-[2,2-bis(3-fluorophenyl)cyclopropyl]-N-[4-(3-pyridinyl)-butyl]-2-propenamide, mp 126°–127° C.

Anal. Calculated for $C_{27}H_{26}F_2N_2O$: C, 74.98; H, 6.06; F, 8.78; N, 6.49. Found: C, 74.94; H, 6.05; F, 8.62; N, 6.84.

EXAMPLE 145

[R-(E)]-3-[2,2-bis(3-Fluorophenyl)(cyclopropyl]-N-[4-(3-pyridinyl)butyl]-2-propenamide As in Example 141, a solution of [R-(E)]-3-[2,2-bis(3-fluorophenyl)cyclopropyl]-2-propenoic acid 4-nitrophenyl ester (2.5 g) and 3-pyridinebutanamine (0.88 g) in tetrahydrofuran (15 mL) was stirred at 25° C. for 75 minutes. After the usual work up, the crude material was purified by HPLC (ethyl acetate) to provide 1.8 g of [R-(E)]-3-[2,2-bis(3-fluorophenyl)cyclopropyl]-N-[4-(3-pyridinyl)butyl]-2-propenamide as an oil, $[\alpha]_D^{25}$ +117.5° (c, 1.0, MeOH).

Anal. Calculated for $C_{27}H_{26}F_2N_2O$: C, 74.98; H, 6.06; F, 8.78; N, 6.48. Found: C, 74.41; H, 6.29; F, 9.28; N, 6.19.

EXAMPLE 146

[S-(E)]-3-[2,2-bis(3-Fluorophenyl)cyclopropyl]-N-[4-(3-pyridinyl)butyl]-2-propenamide As in Example 141, a solution of [S-(E)]-3-[2,2-bis(3-fluorophenyl)cyclopropyl)-2-propenoic acid 4-nitrophenyl ester (4.63 g) and 3-pyridinebutanamine (1.51 g) in tetrahydrofuran (50 mL) was stirred at room temperature for 2 hours. After the usual work up, the crude product was purified by HPLC (ethyl acetate) to furnish 3.4 g of [S-(E)]-3-[2,2-bis(3-fluorophenyl)cyclopropyl]-N-[4-(3-pyridinyl)butyl]-2-propenamide as a colorless oil, $[\alpha]_D^{25}$ −118.3° (c, 1.0, MeOH).

Anal. Calculated for $C_{27}H_{26}F_2N_2O$: C, 74.98; H, 6.06; F, 8.78; N, 6.48. Found: C, 75.35; H, 6.16; F, 9.28; N, 6.49.

EXAMPLE 147

[R-(E)]-3-[2,2-bis(3-Fluorophenyl)-1-methylcyclopropyl)-N-[4-(3-pyridinyl)butyl]-2-propenamide As in Example 141, [R-(E)]-3-[2,2-bis(3-fluorophenyl)-1-methylcyclopropyl]-2-propenoic acid 4-nitrophenyl ester (4.4 g) was reacted with 3-pyridinebutanamine (1.52 g) in tetrahydrofuran (30 mL) at room temperature for 17 hours. After the usual work up, the crude amide was purified by HPLC (ethyl acetate) and then crystallized from ethyl acetate to give 3.55 g [R-(E)]-3-[2,2-bis(3-fluorophenyl)-1-methylcyclopropyl]-N-[4-(3-pyridinyl)butyl]-2-propenamide, mp 154°-155.5° C.; $[\alpha]_D^{25}$ −9.17° (c, 1.0, MeOH).

Anal. Calculated for $C_{28}H_{28}F_2N_2O$: C, 75.32; H, 6.32; F, 8.51; N, 6.27. Found: C, 75.29; H, 6.39; F, 8.26; N, 6.29.

EXAMPLE 148

[S-(E)]-3-[2,2-bis(3-Fluorophenyl)-1-methylcyclopropyl]-N-[4-(3-pyridinyl)butyl]-2-propenamide As in Example 141, [S-(E)]-3-[2,2-bis(3-fluorophenyl)-1-methylcyclopropyl]-2-propenoic acid 4-nitrophenyl ester (3.5 g) was reacted with 3-pyridinebutanamine (1.21 g) in tetrahydrofuran (25 mL) at room temperature for 17 hours. The crude product, obtained from the usual work up, was purified by HPLC (ethyl acetate) and then crystallized from ethyl acetate to provide 3.0 g of [S-(E)]-3-[2,2-bis(3-fluorophenyl)-1-methylcyclopropyl]-N-[4-(3-pyridinyl)butyl]-2-propenamide, mp 154°-155.5° C.; $[\alpha]_D^{25}$ +9.72° (c, 1.0, MeOH).

Anal. Calculated for $C_{28}H_{28}F_2N_2O$: C, 75.32; H, 6.32; F, 8.51; N, 6.27. Found: C, 75.29; H, 6.31; F, 8.51; N, 6.23.

EXAMPLE 149

[S,R*-(E)]-3-[2,2-bis(3-Fluorophenyl)cyclopropyl]-N-[1-methyl-4-(3-pyridinyl)butyl]-2-propenamide 0.3 molar hydrate As in Example 141, [S-(E)]-3-[2,2-bis(3-fluorophenyl)cyclopropyl]-2-propenoic acid 4-nitrophenyl ester (2.8 g) was reacted with (R)-alpha-methyl-3-pyridinebutanamine (1.09 g) in tetrahydrofuran (20 mL) at room temperature for 17 hours. After the usual work up, the crude amide was purified by HPLC (ethyl acetate) and then lyophilized from benzene to provide 2.9 g of [S,R*-(E)]-3-[2,2-bis(3-fluorophenyl)cyclopropyl]-N-[1-methyl-4-(3-pyridinyl)butyl]-2-propenamide as an amorphous solid, $[\alpha]_D^{25}$ −92.7° (c, 1.0, MeOH).

Anal. Calculated for $C_{28}H_{28}F_2N_2O \cdot 0.3H_2O$: C, 74.41; H, 6.38; F, 8.41; N, 6.20; $H_2O$, 1.19. Found: C, 74.53; H, 6.33; F, 8.53; N, 6.20; $H_2O$, 1.13.

EXAMPLE 150

[S-(E)]-3-[2,2-bis(3-Fluorophenyl)cyclopropyl]-N-[1,1-dimethyl-4-(3-pyridinyl)butyl]-2-propenamide As in Example 141, [S-(E)]-3-[2,2-bis(3-fluorophenyl)cyclopropyl]-2-propenoic acid 4-nitrophenyl ester (2.94 g) was reacted with alpha,alpha-dimethyl-3-pyridinebutanamine (1.5 mL) in tetrahydrofuran (30 mL) at 75° C. for 75 hours. The crude product, obtained from the usual work up, was purified by HPLC (ethyl acetate) and then crystallized from ether-hexane to provide 2.3 g of [S-(E)]-3-[2,2-bis(3-fluorophenyl)cyclopropyl]-N-[1,1-dimethyl-4-(3-pyridinyl)butyl]-2-propenamide, mp 74°-75° C.; $[\alpha]_D^{25}$ −124.13° (c, 1.0 MeOH).

Anal. Calculated for $C_{29}H_{30}F_2N_2O$: C, 75.63; H, 6.57; F, 8.25; N, 6.08. Found: C, 75.30; H, 6.60; F, 8.10; N, 6.00.

EXAMPLE 151

[R,S-(E)]-3-[2,2-bis(4-Fluorophenyl)cyclopropyl]-N-(4-(3-pyridinyl)butyl-2-propenamide As in Example 141, a solution of [R,S-(E)]-3-[2,2-bis(4-fluorophenyl)cyclopropyl]-2-propenioc acid 4-nitrophenyl ester (2.4 g) and 3-pyridinebutanamine (0.91 g) in tetrahydrofuran (15 mL) was stirred at room temperature for 75 minutes. The crude amide was isolated in the usual manner and was purified by HPLC (ethyl acetate). The resulting oil was lyophilized from benzene to furnish 1.8 g of [R,S-(E)]-3-[2,2-bis(4-fluorophenyl)-cyclopropyl]-N-[4-(3-pyridinyl)butyl]-2-propenamide as an amorphous solid, mp 60°-80° C.

Anal. Calculated for $C_{27}H_{26}F_2N_2O$: C, 74.98; H, 6.06; F, 8.78; N, 6.48. Found: C, 74.77; H, 6.19; F, 8.57; N, 6.41.

EXAMPLE 152

[R-(E)]-3-[2,2-bis(4-Fluorophenyl)cyclopropyl]-N-[4-(3-pyridinyl)butyl]-2-propenamide As in Example 141, a solution of [R-(E)]-3-[2,2-bis(4-fluorophenyl)cyclopropyl]-2-propenoic acid 4-nitrophenyl ester (4.0 g) and 3-pyridinebutanamine (1.5 g) in tetrahydrofuran (20 mL) was stirred at room temperature for 75 minutes. The crude product obtained from the usual work up was purified by HPLC (ethyl acetate) and then lyophilized from benzene to provide 3.3 g of [R-(E)]-3-[2,2-bis(4-fluorophenyl)cyclopropyl]-N-[4-(3-pyridinyl)butyl]-2-propenamide as an amorphous solid, $[\alpha]_D^{25}$ +122.4° (c, 1.0, MeOH).

Anal. Calculated for $C_{27}H_{26}F_2N_2O$: C, 74.98; H, 6.06; F, 8.78; N, 6.49. Found: C, 74.35; H, 6.14; F, 8.99; N, 6.27.

EXAMPLE 153

[S-(E)]-3-[2,2-bis(4-Fluorophenyl)cyclopropyl]-N-[4-(3-pyridinyl)butyl]-2-propenamide As in Example 141, a solution of [S-(E)]-3-[2,2-bis(4-fluorophenyl)cyclopropyl]-2-propenoic acid 4-nitrophenyl ester (4.0 g) and 3-pyridinebutanamine (1.5 g) in tetrahydrofuran (50 mL) was stirred at room temperature for 2 hours. After the usual work up, the crude amide was purified by HPLC (ethyl acetate) and then lyophilized from benzene to provide 3.4 g of [S-(E)]-3-[2,2-bis(4-fluorophenyl)cyclopropyl]-N-[4-(3-pyridinyl)butyl]-2-propenamide as an amorphous solid, $[\alpha]_D^{25} -118.4°$ (c, 1.0, MeOH).

Anal. Calculated for $C_{27}H_{26}F_2N_2O$: C, 74.98; H, 6.06; F, 8.78; N, 6.48. Found: C, 75.00; H, 6.18; F, 8.86; N, 6.43.

EXAMPLE 154

[R,S-(E)]-3-[2,2-bis(4-Fluorophenyl)-1-methylcyclopropyl]-N-[4-(3-pyridinyl)butyl]-2-propenamide As in Example 141, a solution of [R,S-(E)]-3-[2,2-bis(4-fluorophenyl)-1-methylcyclopropyl]-2-propenoic acid 4-nitropyhenyl ester (3.7 g) and 3-pyridinebutanamine (1.4 g) in tetrahydrofuran (20 mL) was stirred at room temperature for 1.5 hours. The crude amide, isolated in the usual fashion, was purified by HPLC (ethyl acetate). The material was triturated with ether to yield 3.2 g of [R,S-(E)]-3-[2,2-bis(4-fluorophenyl)-1-methylcyclopropyl]-N-[4-(3-pyridinyl)butyl]-2-propenamide, mp 118°–120° C. Crystallization of a portion from ethyl acetate-hexane afforded the analytical sample, mp 120°–122° C.

Anal. Calculated for $C_{28}H_{28}F_2N_2O$: C, 75.32; H, 6.32; F, 8.51; N, 6.27. Found: C, 75.57; H, 6.27; F, 8.74; N, 6.27.

EXAMPLE 155

[R-(E)]-3-[2,2-bis(4-Fluorophenyl)-1-methylcyclopropyl]-N-[4-(3-pyridinyl]-2-propenamide As in Example 141, [R-(E)]-3-[2,2-bis(4-fluorophenyl)-1-methylcyclopropyl]-2-propenoic acid 4-nitrophenyl ester (3.7 g) was reacted with 3-pyridinebutanamine (1.4 g) in tetrahydrofuran (30 mL) at room temperature for 1.5 hours. After the usual work up, the crude amide was purified by HPLC (ethyl acetate) and then crystallized from ether to give 3.1 g of [R-(E)]-3-[2,2-bis(4-fluorophenyl)-1-methylcyclopropyl]-N-[4-(3-pyridinyl)butyl]-2-propenamide, mp 122°–123° C.; $[\alpha]_D^{25} -4.05°$ (c, 1.0, MeOH). Recrystallization of a portion from ethyl acetate-hexane afforded the analytical sample, mp 122.5°–123.5° C.

Anal. Calculated $C_{28}H_{28}F_2N_2O$: C, 75.32; H, 6.32; F, 8.51; N, 6.27. Found: C, 75.23; H, 6.34; F, 8.30; N, 6.29.

EXAMPLE 156

[S-(E)]-3-[2,2-bis(4-Fluorophenyl)-1-methylcyclopropyl]-N-[4-(3-pyridinyl)butyl]-2-propenamide As in Example 141, [S-(E)]-3-[2,2-bis(4-fluorophenyl)-1-methylcyclopropyl]-2-propenoic acid 4-nitrophenyl ester (3.7 g) was reacted with 3-pyridinebutanamine (1.4 g) in tetrahydrofuran (20 mL) at 25° C. for 1.5 hours. The crude amide, isolated through the usual work up, was purified by HPLC (ethyl acetate) and then crystallized from ether to yield 3.0 g of [S-(E)]-3-[2,2-bis(4-fluorophenyl)-1-methylcyclopropyl]-N-[4-(3-pyridinyl)butyl]-2-propenamide, mp 122°–123° C.; $[\alpha]_D^{25} +4.09°$ (c, 1.0, MeOH).

Anal. Calculated for $C_{28}H_{28}F_2N_2O$: C, 75.32; H, 6.32; F, 8.51; N, 6.27. Found: C, 75.32; H, 6.51; F, 8.56; N, 6.33.

EXAMPLE 157

[S,R*-(E)]-3-[2,2-bis(4-Fluorophenyl)cyclopropyl]-N-[1-methyl-4-(3-pyridinyl)butyl]-2-propenamide 0.3 molar hydrate As in Example 141, [S,R*-(E)]-3-[2,2-bis(4-fluorophenyl)cyclopropyl]-2-propenoic acid 4-nitrophenyl ester (2.11 g) was reacted with (R)-alpha-methyl-3-pyridinebutanamine (0.82 g) in tetrahydrofuran (15 mL) at room temperature for 17 hours. The amide, isolated in the normal manner, was purified by HPLC (ethyl acetate) and then lyophilized from benzene to give 2.1 g of [S,R*-(E)]-3-[2,2-bis(4-fluorophenyl)cyclopropyl]-N-[1-methyl-4-(3-pyridinyl)butyl]-2-propenamide 0.3 molar hydrate as an amorphous solid, mp 50°–60° C.; $[\alpha]_D^{25} -49.6°$ (c, 1.0, MeOH).

Anal. Calculated for $C_{28}H_{28}F_2N_2O \cdot 0.3H_2O$: C, 74.41; H, 6.38; F, 8.41; N, 6.20; $H_2O$, 1.19. Found: C, 74.03; H, 6.52; F, 8.23; N, 6.05; $H_2O$, 1.18.

EXAMPLE 158

[R,S-(E)]-3-[2,2-bis(3-Methoxyphenyl)cyclopropyl]-N-[4-(3-pyridinyl)butyl]-2-propenamide As in Example 141, a solution of [R,S-(E)]-3-[2,2-bis(3-methoxyphenyl)cyclopropyl]-2-propenoic acid 4-nitrophenyl ester (4.6 g) and 3-pyridinebutanamine (1.71 g) in tetrahydrofuran (20 mL) was stirred at room temperature for 90 minutes. The crude amide was isolated in the usual fashion and was purified by HPLC (ethyl acetate). The resulting oil was crystallized from ether to furnish 3.4 g of [R,S-(E)]-3-[2,2-bis(3-methoxyphenyl)cyclopropyl]-N-[4-(3-pyridinyl)butyl]-2-propenamide, mp 85°–86° C. A portion was recrystallized from ethyl acetate-hexane to give the analytical sample, mp 85.5°–86.5° C.

Anal. Calculated for $C_{29}H_{32}N_2O_3$: C, 76.29; H, 7.06; N, 6.14. Found: C, 76.31; H, 7.07; N, 6.10.

EXAMPLE 159

[R-(E)]-3-[2,2-bis(3-Methoxyphenyl)cyclopropyl]-N-[4-(3-pyridinyl)butyl]-2-propenamide As in Example 141, a solution of [R-(E)]-3-[2,2-bis(3-methoxyphenyl)cyclopropyl]-2-propenoic acid 4-nitrophenyl ester (4.85 g) and 3-pyridinebutanamine (1.8 g) in tetrahydrofuran (30 mL) was stirred at room temperature for 90 minutes. The crude product obtained from the normal work up was purified by HPLC (ethyl acetate) and lyophilized from benzene to give 4.15 g of [R-(E)]-3-[2,2-bis(3-methoxyphenyl)cyclopropyl]-N-[4-(3-pyridinyl)butyl]-2-propenamide as an amorphous solid, $[\alpha]_D^{25} +128°$ (c, 1.0, MeOH).

Anal. Calculated for $C_{29}H_{34}N_2O_3$: C, 76.29; H, 7.06; N, 6.14. Found: C, 76.46; H, 7.14; N, 5.92.

EXAMPLE 160

[S-(E)]-3-[2,2-bis(3-Methoxyphenyl)cyclopropyl]-N-[4-(3-pyridinyl)butyl]-2-propenamide As in Example 141, a solution of [S-(E)]-3-[2,2-bis(3-methoxyphenyl)cyclopropyl]-2-propenoic acid 4-nitrophenyl ester (6.2 g) and 3-pyridinebutanamine (2.3 g) in tetrahydrofuran (40 mL) was stirred at room temperature for 1 hour. After the usual work up, the crude product was purified by HPLC (ethyl acetate) and then lyophilized from benzene to provide 5.3 g of [S-(E)]-3-[2,2-bis(3-methoxyphenyl)cyclopropyl]-N-[4-(3-pyridinyl)butyl]-2-propenamide as an amorphous solid, $[\alpha]_D^{25} - 129°$ (c, 1.0, MeOH).

Anal. Calculated for $C_{29}H_{34}N_2O_3$: C, 76.57; H, 7.28; N, 5.95. Found: C, 76.58; H, 7.31; N, 5.90.

EXAMPLE 161

[S-(E)]-3-[2,2-bis(3-Methoxyphenyl)cyclopropyl]-N-[1,1-dimethyl-4-(3-pyridinyl)butyl]-2-propenamide As in Example 141, [S-(E)]-3-[2,2-bis(3-methoxyphenyl)cyclopropyl]-2-propenoic acid 4-nitrophenyl ester (1.45 g) was reacted with alpha,alpha-dimethyl-3-pyridinebutanamine (0.55 mL) in tetrahydrofuran (15 mL) at 75° C. for 51 hours. The crude product, isolated in the normal fashion, was purified by HPLC (ethyl acetate-hexane; 4:1) and then lyophilized from benzene to afford 1 g of [S-(E)]-3-[2,2-bis(3-methoxyphenyl)cyclopropyl]-N-[1,1-dimethyl-4-(3-pyridinyl)butyl]-2-propaneamide as an amorphous solid.

Anal. Calculated for $C_{31}H_{36}N_2O_3$: C, 76.83; N, 7.49; N, 5.78. Found: C, 76.85; H, 7.57; N, 5.62.

EXAMPLE 162

[1(R,S),2(R,S)-(E)]-3-[[2-(3-Methoxyphenyl)-2-phenyl]cyclopropyl]-N-[4-(3-pyridinyl)butyl]-2-propenamide As in Example 141, [1(R,S),2(R,S)-(E)]-2-[[2-(3-methoxyphenyl)-2-phenyl]cyclopropyl]-2-propenoic acid 4-nitrophenyl ester (1.6 g) was reacted with 3-pyridinebutanamine (0.64 g) in tetrahydrofuran (15 mL) at ambient temperature for 2 hours. The crude product, isolated in the usual manner, was purified by HPLC (ethyl acetate) and then crystallized from ether to furnish 1.2 g of [1(R,S),2(R,S)-(E)]-3-[[2-(3-methoxyphenyl)-2-phenyl]cyclopropyl]-N-[4-(3-pyridinyl)butyl]-2-propenamide, mp 107°-108° C. Recrystallization from ethyl acetate-hexane did not alter the melting point.

Anal. Calculated for $C_{28}H_{30}N_2O_2$: C, 78.84; H, 7.09; N, 6.57. Found: C, 78.62; H, 7.07; N, 6.32.

EXAMPLE 163

[1(R,S),2(S,R)-(E)]-3-[[2-(3-Methoxyphenyl)-2-phenyl]cyclopropyl]-N-[4-(3-pyridinyl)butyl]-2-propenamide As in Example 141, [1(R,S),2(S,R)-(E)]-3-[[2-(3-methoxyphenyl)-2-phenyl]cyclopropyl]-2-propenoic acid 4-nitrophenyl ester (1.55 g) was reacted with 3-pyridinebutanamine (0.64 g) in tetrahydrofuran (15 mL) at room temperature for 2 hours. The crude product, isolated in the usual manner, was purified by HPLC (ethyl acetate) and then lyophilized from benzene to furnish 1.2 g of [1(R,S),2(S,R)-(E)]-3-[[2-(3-methoxyphenyl)-2-phenylcyclopropyl]-N-[4-(3-pyridinyl)butyl]-2-propenamide, as a thick oil.

Anal. Calculated for $C_{28}H_{30}N_2O_2$: C, 78.84; H, 7.09; N, 6.57. Found: C, 78.97; H, 7.14; N, 6.45.

EXAMPLE 164

[R,S-(E)]-3-[2,2-bis[3-Trifluoromethyl)phenyl]cyclopropyl]-N-[4-(3-pyridinyl)butyl]-2-propenamide As in Example 141, a solution of [R,S-(E)]-3-[2,2-bis[3-(trifluoromethyl)phenyl]cyclopropyl]-2-propenoic acid 4-nitrophenyl ester (2.45 g) and 3-pyridinebutanamine (0.706 g) in tetrahydrofuran (10 mL) was stirred at room temperature for 1.5 hours. The crude amide, isolated in the usual way, was purified by HPLC (ethyl acetate) and then was crystallized from ether-hexane (2×) to yield 1.75 g of [R,S-(E)]-3-[2,2-bis[3-(trifluoromethyl)phenyl]cyclopropyl]-N-[4-(3-pyridinyl)butyl]-2-propenamide, mp 119°-121° C.

Anal. Calculated for $C_{29}H_{26}F_6N_2O$: C, 64.51; H, 4.92; F, 21.41; N, 5.26. Found: C, 64.45; H, 5.08; F, 21.69; N, 5.27.

EXAMPLE 165

[R,S-(Z)]-3-(2,2-Diphenylcyclopropyl)-N-[4-(3-pyridinyl)butyl]-2-propenamide

As in Example 141, a solution of [R,S-(Z)]-3-(2,2-diphenylcyclopropyl)-2-propenoic acid 4-nitrophenyl ester (6.17 g) and 3-pyridinebutanamine (2.5 g) in tetrahydrofuran (50 mL) was stirred at room temperature for 2 hours. The crude amide, isolated in the usual way, was purified by HPLC (ethyl acetate-hexane-triethylamine; 45:5:1) and then was crystallized from ethyl acetate-hexane to yield 3.3 g of (R,S)-(Z)-3-(2,2-diphenylcyclopropyl)-N-[4-(3-pyridinyl)butyl]-2-propenamide, mp 115°-116° C.

Anal. Calculated for $C_{27}H_{28}N_2O$: C, 81.78; H, 7.12; N, 7.06. Found: C, 81.76; H, 7.04; N, 7.00.

EXAMPLE 166

[R-(Z)]-3-(2,2-Diphenylcyclopropyl)-N-[4-(3-pyridinyl)butyl]-2-propenamide

As in Example 141, a solution of [R-(Z)]-3-(2,2-diphenylcyclopropyl)-2-propenoic acid 4-nitrophenyl ester (6.1 g) and 3-pyridinebutanamine (2.5 g) in tetrahydrofuran (50 mL) was stirred at room temperature for 2 hours. The usual work up provided 7 g of crude amide that was purified by HPLC (ethyl acetate) and then crystallized from ethyl acetate-hexane to provide 4.6 g of (R)-(Z)-3-(2,2-diphenylcyclopropyl)-N-[4-(3-pyridinyl)butyl]-2-propenamide, mp 115°-116° C.; $[\alpha]_D^{25} - 149.2°$ (c, 1.0, MeOH).

Anal. Calculated for $C_{27}H_{28}N_2O$: C, 81.78; H, 7.12; N, 7.06. Found: C, 81.70; H, 7.29; N, 6.97.

EXAMPLE 167

[S-(Z)]-3-(2,2-Diphenylcyclopropyl)-N-[4-(3-pyridinyl)butyl]-2-propenamide

As in Example 141, a solution of [S-(Z)]-3-(2,2-diphenylcyclopropyl)-2-propenoic acid 4-nitrophenyl ester (6.8 g) and 3-pyridinebutanamine (2.7 g) in tetrahydrofuran (50 mL) was stirred at room temperature for 2 hours. After the usual work up, the crude product was first purified by HPLC (ethyl acetate) and then crystallized from ethyl acetate-hexane to give 5.4 g of [S-(Z)]-3-(2,2-diphenylcyclopropyl)-N-[4-(3-pyridinyl)butyl]-2-propenamide, mp 115°-116° C.; $[\alpha]_D^{25} + 150.4°$ (c, 1.0, MeOH).

Anal. Calculated for $C_{27}H_{28}N_2O$: C, 81.78; H, 7.12; N, 7.06. Found: C, 81.64; H, 6.78; N, 6.93.

EXAMPLE 168

[R,S-(Z)]-3-[2,2-bis(3-Fluorophenyl)cyclopropyl]-N-[4-(3-pyridinyl)butyl]-2-propenamide As in Example 141, a solution of [R,S-(Z)]-3-[2,2-bis(3-fluorophenyl)cyclopropyl]-2-propenoic acid 4-nitrophenyl ester (2.9 g) and 3-pyridinebutanamine (1.05 g) in tetrahydrofuran (20 mL) was stirred at room temperature for 2 hours. The crude product was isolated in the usual manner and was purified by HPLC (ethyl acetate). The resulting solid was crystallized from ethyl acetate-hexane to afford 2.3 g of [R,S-(Z)]-3-[2,2-bis(3-fluorophenyl)cyclopropyl]-N-[4-(3-pyridinyl)butyl]-2-propenamide, mp 129°–130° C.

Anal. Calculated for $C_{27}H_{26}F_2N_2O$: C, 74.98; H, 6.06; F, 8.78; N, 6.48. Found: C, 74.97; H, 6.14; F, 8.63; N, 6.56.

EXAMPLE 169

[R,S-(Z)]-3-[2,2-bis(4-Fluorophenyl)cyclopropyl]-N-[4-(3-pyridinyl)butyl]-2-propenamide As in Example 141, a solution of [R,S-(Z)]-3-[2,2-bis(4-fluorophenyl)cyclopropyl]-2-propenoic acid 4-nitrophenyl ester (1.26 g) and 3-pyridinebutanamine (0.455 g) in tetrahydrofuran (7 mL) was stirred at room temperature for 75 minutes. The crude product, isolated in the normal fashion, was purified by HPLC (ethyl acetate) and then was crystallized from ether-hexane to furnish 0.887 g of [R,S-(Z)]-3-[2,2-bis(4-fluorophenyl)-cyclopropyl]-N-[4-(3-pyridinyl)butyl]-2-propenamide, mp 89°–91° C. Recrystallization of a portion from ethyl acetate-hexane yielded the pure amide, mp 90°–91.5° C.

Anal. Calculated for $C_{27}H_{26}F_2N_2O$: C, 74.98; H, 6.06; F, 8.78; N, 6.48. Found: C, 74.98; H, 6.13; F, 8.88; N, 6.33.

EXAMPLE 170

[1(R,S),2(R,S)-(Z)]-3-[[2-(3-Methoxyphenyl)-2-phenyl]-cyclopropyl]-N-[4-(3-pyridinyl)butyl]-2-propenamide As in Example 141, [1(R,S),2(R,S)-(Z)]-3-[[2-(3-methoxyphenyl)-2-phenyl]cyclopropyl]-2-propenoic acid 4-nitrophenyl ester (1.3 g) was treated with 3-pyridinebutanamine (0.554 g) in tetrahydrofuran (15 mL) at ambient temperature for 2 hours. The crude amide, isolated in the usual manner, was purified by HPLC (ethyl acetate) to provide 1.1 g of [1(R,S),2(R,S)-(Z)]-3-[[2-(3-methoxyphenyl)-2-phenyl]-cyclopropyl]-N-[4-(3-pyridinyl)butyl]-2-propenamide, mp 116°–117° C. Crystallization of a sample from ethyl acetate-hexane did not affect the melting point.

Anal. Calculated for $C_{28}H_{30}N_2O_2$: C, 78.84; H, 7.09; N, 6.57. Found: C, 78.90; H, 7.00; N, 6.55.

EXAMPLE 171

[1(R,S),2(S,R)-(Z)]-3-[[2-(3-Methoxyphenyl)-2-phenyl]-cyclopropyl]-N-[4-(3-pyridinyl)butyl]-2-propenamide As in Example 141, [1(R,S),2(S,R)-(Z)]-3-[[2-(3-methoxyphenyl)-2-phenyl]cyclopropyl]-2-propenoic acid 4-nitrophenyl ester (1.4 g) was reacted with 3-pyridinebutanamine (0.58 g) in tetrahydrofuran (15 mL) at room temperature for 2 hours. The crude product, isolated in the normal fashion, was purified by HPLC (ethyl acetate). Trituration of the resulting solid with ether-hexane furnished 1.1 g of [1(R,S),2(S,R)-(Z)]-3-[[2-(3-methoxyphenyl)-2-phenyl]cyclopropyl]-N-[4-(3-pyridinyl)butyl]-2-propenamide. Crystallization of a portion from ethyl acetate-hexane afforded the analytical sample, mp 112.5°–113.5° C.

Anal. Calculated for $C_{28}H_{30}N_2O_2$: C, 78.84; H, 7.09; N, 6.57. Found: C, 78.39; H, 7.05; N, 6.54.

EXAMPLE 172

(R,S)-2,2-Diphenyl-N-[4-(3-pyridinyl)butyl]cyclopropanepropanamide

As in Example 141, a solution of (R,S)-2,2-diphenyl-N-[4-(3-pyridinyl)butyl]cyclopropanepropanoic acid 4-nitrophenyl ester (6.2 g) and 3-pyridinebutanamide (2.5 g) in tetrahydrofuran (50 mL) was stirred at room temperature for 2 hours. The crude amide, isolated in the usual way, was purified by HPLC (ethyl acetate-hexane-triethylamine; 45:5:1) and then crystallized from ethyl acetate-hexane to yield 3.8 g of (R,S)-2,2-diphenyl-N-[4-(3-pyridinyl)butyl]cyclopropanepropanamide, mp 96.5°–97.5° C.

Anal. Calculated for $C_{27}H_{30}N_2O$: C, 81.37; H, 7.59; N, 7.03. Found: C, 81.28; H, 7.53; N, 7.03.

EXAMPLE 173

(R)-2,2-Diphenyl-N-[4-(3-pyridinyl)butyl]cyclopropanepropanamide

As in Example 141, (R)-2,2-diphenylcyclopropanepropanoic acid 4-nitrophenyl ester (4.8 g) was treated with 3-pyridinebutanamine (1.88 g) in tetrahydrofuran (110 mL) at 25° C. for 2 hours. The crude product, isolated in the normal manner, was purified by HPLC (ethyl acetate-hexane; 9:1) and lyophilized from benzene to give 4.3 g of (R)-2,2-diphenyl-N-[4-(3-pyridinyl)butyl]cyclopropanepropanamide as an oil, $[\alpha]_D^{25} + 86.4°$ (c, 1.0, MeOH).

Anal. Calculated for $C_{29}H_{30}N_2O$: C, 81.37; H, 7.59; N, 7.03. Found: C, 80.91; H, 7.54; N, 6.79.

EXAMPLE 174

(S,R*)-(E)-3-[2,2-bis(3-Methoxyphenyl)cyclopropyl]-N-[1-methyl-4-(3-pyridinyl)butyl]-2-propenamide As in example 141, (S)-(E)-3-[2,2-bis(3-methoxyphenyl)cyclopropyl]-2-propenoic acid 4-nitrophenyl ester (2.2 g) was reacted with (R)-alpha-methyl-3-pyridinebutanamine (0.81 g) in tetrahydrofuran (15 mL) at ambient temperature overnight. The crude product, isolated in the usual manner, was purified by HPLC (ethyl acetate) and then crystallized from ethyl acetate-hexane to give 1.4 g of (S,R*)-(E)-3-[2,2-bis(3-methoxyphenyl)-cyclopropyl]-N-[1-methyl-4-(4pyridinyl)-butyl]-2-propenamide, mp 104°–106° C.

Anal. Calcd. for $C_{30}H_{34}N_2O_3$: C, 76.576; H, 7.28; N, 5.95. Found: C, 76.58; H, 7.31; N, 5.900.

EXAMPLE 175

(S)-2,2-Diphenyl-N-[4-(3-pyridinyl)butyl]cyclopropanepropanamide

As above (S)-2,2-diphenylcyclopropanepropanoic acid 4-nitrophenyl ester (6.0 g) was reacted with 3-pyridine (2.4 g) in tetrahydrofuran (100 mL) at 25° C. for 2 hours. After the usual work up, the amide was purified by HPLC (ethyl acetate-hexane; 9:1) to yield 5.5 g of (S)-2,2-diphenyl-N-[4-(3-pyridinyl)butyul]cyclopropanepropanamide as an oil, $[\alpha]_D^{25} - 87.3°$ (c, 1.0, MeOH).

Anal. Calcd. for $C_{27}H_{30}N_2O$: C, 81.37; H, 7.59; N, 7.03. Found: C, 81.43; H, 7.71; N, 7.09.

EXAMPLE 176

(R,S)-(E)-3-(Diphenylcyclopropyl)-N-[4-(3-pyridinyl)butyl]-2-propenethioamide a solution of (R,S)-(E)-3-(diphenylcyclopropyl)-N-[4-(3-pyridinyl)butyl]-2-propenamide (0.793 g) and phosphorus pentasulfide (0.445 g) in dry pyridine (37 mL) was refluxed for 2.5 hours. After the solvent was removed in vacuo, the residue was partitioned between dichloromethane (25 mL) and 1N sodium hydroxide solution (25 mL). The separated aqueous phase was reextracted with dichloromethane 915 mL) and the combined extracts were dried (MgSO$_4$) and evaporated to give 0.8 g of crude product. The material was purified by HPLC (ethyl acetate-hexane; 4:1) to furnish 0.4 g of (R,S)-(E)-3-(diphenylcyclopropyl)-N-[4-(3-pyridinyl)butyl]-2-propenethioamide as a foam.

Anal. Calcd. for C$_{27}$H$_{28}$N$_2$S: C, 78.0, H, 6.84; N, 6.79; S, 7.77. Found: C, 78.46; H, 6.88; N, 6.59; S, 7.53.

EXAMPLE 177

| INHALATION AEROSOL FORMULATION (SOLUTION) | | |
|---|---|---|
| Item | Ingredients | % w/w |
| 1. | [S-(E)]-3-]2,2-bis(4-fluorophenyl)cyclopropyl]-N-[4-(3-pyridinyl)butyl]-2-propenamide | 1.0 |
| 2. | Ethyl Alcohol | 30.0 |
| 3. | Ascorbic Acid | 0.5 |
| 4. | Freon 12 | 54.8 |
| 5. | Freon 114 | 13.7 |
| | TOTAL | 100% |

Manufacturing Procedure (1) Dissolve Items 1 and 3 in Item 2.
(2) Fill solution from step 1 into a suitable glass bottle, insert valve and crimp to seal container.
(3) Pressure-fill a 80:20 mixture of Items 4 and 5 into the container.
NOTE: A suitable valve may be used to deliver 25 to 100 microliters in volume.

EXAMPLE 178

| INHALATION AEROSOL FORMULATION (SUSPENSION) | | |
|---|---|---|
| Item | Ingredients | % w/w |
| 1. | [S-(E)]-3-[2,2-bis(4-fluorophenyl)cyclopropyl]-N-[4-(3-pyridinyl)butyl]-2-propenamide | 1.0 |
| 2. | Sorbitan Trioleate | 0.5 |
| 3. | Freon 12 | 64.0 |
| 4. | Freon 11 | 18.5 |
| 5. | Freon 114 | 16.0 |
| | TOTAL | 100% |

Manufacturing Procedure (1) Mix Items 1 and 2 into 4 and homogenize.
(2) Fill the concentrate suspension from Step 1 into a suitable can and place in valve and crimp to seal container.
(3) Pressure-fill a 80:20 mixture of Items 3 and 5.
NOTE: A suitable valve may be used to deliver 25–100 microliters in volume.

EXAMPLE 179

| TABLET FORMULATION (Wet Granulation) | | mg/tablet | |
|---|---|---|---|
| Item | Ingredients | 100 mg | 500 mg |
| 1. | [S-(E)]-3-[2,2-bis(4-fluorophenyl)cyclopropyl]-N-[4-(3-pyridinyl)butyl]-2-propenamide | 100 | 500 |
| 2. | Lactose | 30 | 150 |
| 3. | Pregelatinized Starch | 6 | 30 |
| 4. | Microcrystalline Cellulose | 30 | 150 |
| 5. | Magnesium Stearate | 1 | 6 |
| | TOTAL | 167 | 836 |

Manufacturing Procedure (1) Mix Items 1, 2, 3 and 4 and granulate with water.
(2) Dry the granulation at 50° C.
(3) Pass the granulation through suitable milling equipment.
(4) Add Item 5 and mix for three minutes; compress on a suitable press.

EXAMPLE 180

| CAPSULE FORMULATION | | mg/tablet | |
|---|---|---|---|
| Item | Ingredients | 100 mg | 500 mg |
| 1. | [S-(E)[-3-[2,2-bis(4-Fluorophenyl)cyclopropyl]-N-[4-(3-pyridinyl)butyl]-2-propenamide | 100 | 500 |
| 2. | Corn Starch (Pregelatinized) | 8 | 40 |
| 3. | Modified Starch | 4 | 20 |
| 4. | Talc | 4 | 20 |
| 5. | Magnesium Stearate | 1 | 2 |
| | TOTAL | 117 | 117 |

Manufacturing Procedure (1) Mix Items 1, 2, and 3 and wet granulate with water. Dry at 45° C. overnight.
(2) Mill through suitable screeen using appropriate milling equipment.
(3) Add Items 4 and 5 and mix for five minutes.

EXAMPLE 181

| CAPSULE FORMULATION | | | | | |
|---|---|---|---|---|---|
| Item | Ingredient | mg/capsule | | | |
| 1. | [S-(E)]-3-[2,2-bis(4-Fluorophenyl)cyclopropyl]-N-[4-(3-pyridinyl)butyl]-2-propenamide | 0.01 | 0.5 | 5.0 | 25.0 |
| 2. | Lactose Hydrous | 168.99 | 168.5 | 159.0 | 123.0 |
| 3. | Corn Starch | 20.0 | 20.0 | 25.0 | 35.0 |
| 4. | Talc | 10.0 | 10.0 | 10.0 | 15.0 |
| 5. | Magnesium Stearate | 1.0 | 1.0 | 1.0 | 2.0 |
| | TOTAL | 200.0 | 200.0 | 200.0 | 200.0 |

Manufacturing Procedure (1) Mix Items 1, 2 and 3 in a suitable mixer for 30 minutes.
(2) Add Items 4 and 5 and mix for 3 minutes.
(3) Fill into suitable capsule.

EXAMPLE 182

| WET GRANULATION FORMULATION | | | | |
|---|---|---|---|---|
| Item | Ingredient | | mg/tablet | |
| 1. | [S-(E)]-3-[2,2-bis(4-Fluorophenyl cyclopropyl]-N-[4-(3-pyridinyl)butyl]-2-propenamide | 0.01 0.5 5.0 25.0 | | |
| 2. | Lactose Anhydrous DTG | 106.99 | 106.5 102.0 118.0 | |
| 3. | Avicel PH 102 | 15.0 | 15.0 15.0 25.0 | |
| 4. | Modified Starch | 7.0 | 7.0 7.0 10.0 | |
| 5. | Magnesium Stearate | 1.0 | 1.0 1.0 2.0 | |
| | TOTAL | 130.0 | 130.0 130.0 180.0 | |

Manufacturing Procedure (1) Dissolve Item 1 in a suitable solvent such as alcohol.
(2) Spread the solution in Step 1 over Item 2, dry.
(3) Add Items 3 and 4 and mix for 10 minutes.
(4) Add magnesium stearate and mix for 3 minutes and compress.

EXAMPLE 183

| CREAM 0.5% | | |
|---|---|---|
| Ingredients | g/kg | Reasonable Variations |
| [S-(E)]-3-[2,2-bis(4-Fluorophenyl)cyclopropyl]-N-[4-(3-pyridinyl)butyl]-2-propenamide | 5.150* | — |
| Glyceryl Monostearate S.E.[1] | 100.00 | 80–120 |
| Polysorbate 60[2] | 20.00 | 15–25 |
| Cetyl Alcohol | 50.00 | 40–60 |
| Petrolatum | 70.00 | 50–90 |
| Methylparaben | 1.50 | 1.25–1.75 |
| Propylparaben | 0.50 | 0.4–0.6 |
| Propylene Glycol | 200.00 | 150–250 |
| Purified Water | 568.05 | 475–575 |
| TOTAL | 1,015.20 | |

*3% excess
[1] Arlacel 165
[2] Tween 60

We claim:

1. A compound of the formula

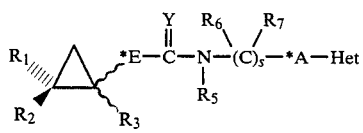

Y is O or S, *A is paraphenylene or *—(CH$_2$)$_n$—(X)$_m$—(CH$_2$)$_r$—, X is O, S or —CH=CH—, n or r, independently, are integers from 0 to 3, s is an integer from 0 to 1, m is an integer from 0 to 1, provided that when m is 1, n+s must be at least 2, R$_1$ and R$_2$, independently, are hydrogen, lower alkyl, cycloalkyl, lower alkenyl, naphthalenyl, phenyl or phenyl or naphthalenyl mono-, di- or trisubstituted by halogen, trifluoromethyl, lower alkyl, phenyl, lower alkoxy or nitro, *E is

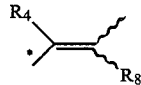

or —(CH$_2$)$_k$— wherein k is an integer from 0 to 4, R$_3$, R$_4$ and R$_8$ are independently hydrogen or lower alkyl, R$_5$ and R$_6$, independently are hydrogen or lower alkyl, R$_7$ is hydrogen, lower alkyl, cycloalkyl, pyrimidinyl lower alkyl, naphthalenyl, phenyl or phenyl or naphthalenyl mono-, di- or trisubstituted by halogen, trifluoromethyl, lower alkyl, phenyl, lower alkoxy or nitro Het is pyrimidinyl which may be substituted by lower alkyl, halogen or phenyl, and the asterisk denotes the point of attachment, or an enantiomer, diastereomers or racemic mixture thereof, as well as when *E is

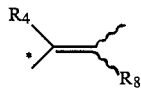

a geometric isomer thereof, or a pharmaceutically acceptable acid addition salt thereof.

2. A compound in accordance with claim 1, wherein R$_1$ and R$_2$, independently, are lower alkyl naphthalenyl, phenyl or phenyl or naphthalenyl mono-, di- or trisubstituted by halogen, trifluoromethyl, lower alkyl, phenyl, lower alkoxy or nitro, R$_3$, R$_4$ and R$_8$, independently, are hydrogen or lower alkyl, R$_5$ and R$_7$ are hydrogen, R$_6$ is hydrogen, lower alkyl or cycloalkyl, *A is *—(CH$_2$)$_n$—(X)$_m$—(CH$_2$)$_r$ wherein n+r=2 to 6, m=0, Het is pyrimidinyl unsubstituted or substituted by lower alkyl, halogen or phenyl, Y is oxygen or sulfur, and s is 1.

3. A compound, in accordance with claim 1, wherein R$_1$ is lower alkyl naphthalenyl, phenyl or phenyl or naphthalenyl mono-, di- or trisubstituted by halogen, trifluoromethyl, lower alkyl, phenyl, lower alkoxy or nitro, R$_2$ is naphthalenyl, phenyl or phenyl or naphthalenyl mono-, di- or trisubstituted by halogen, trifluoromethyl, lower alkyl, phenyl, lower alkoxy or nitro, R$_3$, R$_4$ and R$_8$, independently, are hydrogen or lower alkyl, *A is *—(CH$_2$)$_n$—(X)$_m$—(CH$_2$)$_r$, wherein n+r=3, m=0, Het is pyrimidinyl unsubstituted or substituted with lower alkyl, R$_5$ and R$_7$ are hydrogen, R$_6$ is hydrogen, lower alkyl or cycloalkyl, Y is oxygen, s is 1, *E is

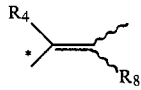

4. A compound, in accordance with claim 1, wherein [S-(E)]-3-(2,2-diphenylcyclopropyl)-N-[4-(5-pyrimidinyl)butyl]-2-propenamide.

5. A compound, in accordance with claim 1, wherein [S,-(E)]-3-[2,2-bis(3-fluorophenyl]cyclopropyl]-N-[4-(5-pyrimidinyl)butyl]-2-propenamide.

6. A compound, in accordance with claim 1, wherein [S,R*-(E)]-3-[2,2-bis(3-fluorophenyl)cyclopropyl]-N-[1-methyl-4-(5-pyrimidinyl)butyl]-2-propenamide.

7. A pharmaceutical composition comprising an effective amount of a compound of the formula

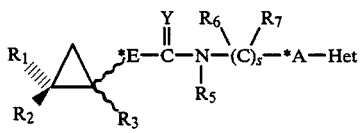

Y is O or S, *A is paraphenylene or —(CH$_2$)$_n$—(X—)$_m$—(CH$_2$)$_r$—, X is O, S or —CH=CH—, n or r, independently, are integers from 0 to 3, s is an integer from 0 to 1, m is an integer from 0 to 1, provided that when m is 1, n+s must be at least 2, R$_1$ and R$_2$, independently, are hydrogen, lower alkyl, cycloalkyl, lower alkenyl, naphthalenyl, phenyl or phenyl or naphthalenyl mono-, di- or trisubstituted by halogen, trifluoromethyl, lower alkyl, phenyl, lower alkoxy or nitro, *E is

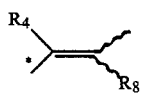

or —(CH$_2$)$_k$— wherein k is an integer from 0 to 4, R$_3$, R$_4$ and R$_8$ are independently hydrogen or lower alkyl, R$_5$ and R$_6$, independently are hydrogen or lower alkyl, R$_7$ is hydrogen, lower alkyl, cycloalkyl, pyrimidinyl lower alkyl, naphthalenyl, phenyl or phenyl or naphthalenyl mono-, di- or trisubstituted by halogen, trifluoromethyl, lower alkyl, phenyl, lower alkoxy or nitro Het is pyrimidinyl which may be substituted by lower alkyl, halogen or phenyl, and the asterisk denotes the point of attachment,
or an enantiomer, diastereomers or racemic mixture thereof, as well as when *E is

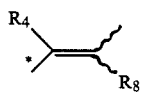

a geometric isomer thereof, or a pharmaceutically acceptable acid addition salt thereof, and an inert carrier.

8. A pharmaceutical composition in accordance with claim 7, wherein R$_1$ and R$_2$, independently, are lower alkyl naphthalenyl, phenyl or phenyl or naphthalenyl mono-, di- or trisubstituted by halogen, trifluoromethyl, lower alkyl, phenyl, lower alkoxy or nitro, R$_3$, R$_4$ and R$_8$, independently, are hydrogen or lower alkyl, R$_5$ and R$_7$ are hydrogen, R$_6$ is hydrogen, lower alkyl or cycloalkyl, *A is *—(CH$_2$)$_n$—(X)$_m$—(CH$_2$)$_r$ wherein n+r=2 to 6, m=0, Het is pyrimidinyl unsubstituted or substituted by lower alkyl, halogen or phenyl, Y is oxygen or sulfur, and s is 1.

9. A pharmaceutical composition, in accordance with claim 7, wherein R$_1$ is lower alkyl naphthalenyl, phenyl or phenyl or naphthalenyl mono-, di- or trisubstituted by halogen, trifluoromethyl, lower alkyl, phenyl, lower alkoxy or nitro, R$_2$ is naphthalenyl, phenyl or phenyl or naphthalenyl mono-, di- or trisubstituted by halogen, trifluoromethyl, lower alkyl, phenyl, lower alkoxy or nitro, R$_3$, R$_4$ and R$_8$, independently, are hydrogen or lower alkyl, *A is *—(CH$_2$)$_n$—(X)$_m$—(CH$_2$)$_r$, wherein n+r=0, m=0, Het is pyrimidinyl unsubstituted or substituted with lower alkyl, R$_5$ and R$_7$ are hydrogen, R$_6$ is hydrogen, lower alkyl or cyclopropyl, Y is oxygen, s is 1, *E is

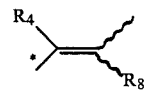

10. A pharmaceutical composition, in accordance with claim 7, wherein the compound is [S-(E)]-3-(2,2-diphenylcyclopropyl)-N-[4-(5-pyrimidinyl)butyl]-2-propenamide.

11. A pharmaceutical composition, in accordance with claim 7, wherein the compound is [S-(+)-(E)]-3-[2,2-bis(3-fluorophenyl)cyclopropyl]-N-[4-(5-pyrimidinyl)butyl]-2-propenamide.

12. A pharmaceutical composition, in accordance with claim 7, wherein the compound is [S,R*-(E)]-3-[2,2-bis(3-fluorophenyl)cyclopropyl]-N-[1-methyl-4-(5-pyrimidinyl)butyl]-2-propenamide.

13. A method of treating a disease state characterized by an excess of platelet activating factor which comprises administration of a compound of the formula

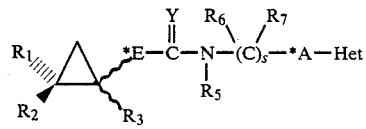

Y is O or S, *A is paraphenylene or *—(CH$_2$)$_n$—(X—)$_m$—(CH$_2$)$_r$—, X is O, S or —CH=CH—, n or r, independently, are integers from 0 to 3, s is an integer from 0 to 1, m is an integer from 0 to 1, provided that when m is 1, n+s must be at least 2, R$_1$ and R$_2$, independently, are hydrogen, lower alkyl, cycloalkyl, lower alkenyl, naphthalenyl, phenyl or phenyl or naphthalenyl mono-, di- or trisubstituted by halogen, trifluoromethyl, lower alkyl, phenyl, lower alkoxy or nitro, *E is

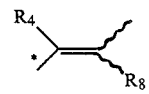

or —(CH$_2$)$_k$— wherein k is an integer from 0 to 4, R$_3$, R$_4$ and R$_8$ are independently hydrogen or lower alkyl, R$_5$ and R$_6$, independently are hydrogen or lower alkyl, R$_7$ is hydrogen, lower alkyl, cycloalkyl, pyrimidinyl lower alkyl, naphthalenyl, phenyl or phenyl or naphthalenyl mono-, di- or trisubstituted by halogen, trifluoromethyl, lower alkyl, phenyl, lower alkoxy or nitro Het is pyrimidinyl which may be substituted by lower alkyl, halogen or phenyl, and the asterisk denotes the point of attachment,
or an enantiomer, diastereomers or racemic mixture thereof, as well as when *E is

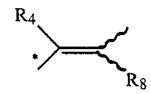

a geometric isomer thereof, or a pharmaceutically acceptable acid addition salt thereof.

14. A method in accordance with claim 13, wherein R$_1$ and R$_2$, independently, are lower alkyl naphthalenyl, phenyl or phenyl or naphthalenyl mono-, di- or trisubstituted by halogen, trifluoromethyl, lower alkyl, phenyl, lower alkoxy or nitro, $R_3$, $R_4$ and $R_8$, independently, are hydrogen or lower alkyl, $R_5$ and $R_7$ are hydrogen, $R_6$ is hydrogen, lower alkyl or cycloalkyl, *A is *—$(CH_2)_n$—$(X)_m$—$(CH_2)_r$ wherein $n+r=2$ to 6, $m=0$, Het is pyrimidinyl unsubstituted or substituted by lower alkyl, halogen or phenyl, Y is oxygen or sulfur, and s is 1.

15. A method, in accordance with claim 13, wherein $R_1$ is lower alkyl naphthalenyl, phenyl or phenyl or naphthalenyl mono, di- or trisubstituted by halogen, trifluoromethyl, lower alkyl, phenyl, lower alkoxy or nitro, $R_2$ is naphthalenyl, phenyl or phenyl or naphthalenyl mono-, di- or trisubstituted by halogen, trifluoromethyl, lower alkyl, phenyl, lower alkoxy or nitro, $R_3$, $R_4$ and $R_8$, independently, are hydrogen or lower alkyl, *A is *—$(CH_2)_n$—$(X)_m$—$(CH_2)_r$, wherein $n+r=0$, $m=0$, Het is pyrimidinyl unsubstituted or substituted with lower alkyl, $R_5$ and $R_7$ are hydrogen, $R_6$ is hydrogen, lower alkyl or cyclopropyl, Y is oxygen, s is 1, *E is

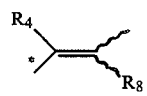

16. A method, in accordance with claim 13, wherein the compound is [S-(E)]-3-(2,2-diphenylcyclopropyl)-N-[4-(5-pyrimidinyl)butyl]-2-propenamide.

17. A method, in accordance with claim 13, wherein the compound is [S-(E)]-3-[2,2-bis(3-fluorophenyl]cyclopropyl]-N-[4-(5-pyrimidinyl)butyl]-2-propenamide.

18. A method, in accordance with claim 13, wherein the compound is [S,R*-(E)]-3-[2,2-bis(3-fluorophenyl)-cyclopropyl]-N-[1-methyl-4-(5-pyrimidinyl)butyl]-2-propenamide.

* * * * *

UNITED STATES PATENT AND TRADEMARK OFFICE
CERTIFICATE OF CORRECTION

PATENT NO. : 4,927,826

DATED : May 22, 1990

INVENTOR(S) : Robert William Guthrie, Richard Wightman Kierstead, Jefferson Wright Tilley It is certified that error appears in the above-identified patent and that said Letters Patent is hereby corrected as shown below:

Claim 9, Column 85, line 65

$n + r = 0$,   should be   $n + r = 3$,

Claim 15, Column 87, line 18, $n + r = 0$,   should be   $n + r = 3$,

Signed and Sealed this

Third Day of September, 1991

*Attest:*

HARRY F. MANBECK, JR.

*Attesting Officer*   *Commissioner of Patents and Trademarks*